(12) United States Patent
Kabadi et al.

(10) Patent No.: US 11,590,083 B2
(45) Date of Patent: *Feb. 28, 2023

(54) TARGETED GASTROINTESTINAL TRACT DELIVERY OF PROBIOTIC ORGANISMS AND/OR THERAPEUTIC AGENTS

(71) Applicant: Therabiome, LLC, Marlboro, NJ (US)

(72) Inventors: Mohan Kabadi, Marlboro, NJ (US); Jerome J. Schentag, Amherst, NJ (US)

(73) Assignee: Therabiome, LLC, Marlboro, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/446,053

(22) Filed: Jun. 19, 2019

(65) Prior Publication Data

US 2020/0138722 A1 May 7, 2020

Related U.S. Application Data

(60) Continuation of application No. 15/874,543, filed on Jan. 18, 2018, now Pat. No. 10,369,111, which is a (Continued)

(51) Int. Cl.
*A61K 9/48* (2006.01)
*A61K 35/741* (2015.01)
(Continued)

(52) U.S. Cl.
CPC .......... *A61K 9/4808* (2013.01); *A61K 9/4816* (2013.01); *A61K 9/4866* (2013.01);
(Continued)

(58) Field of Classification Search
None
See application file for complete search history.

(56) References Cited

U.S. PATENT DOCUMENTS

| 4,193,985 A | 3/1980 | Bechgaard et al. |
| 4,230,687 A | 10/1980 | Sair et al. |

(Continued)

FOREIGN PATENT DOCUMENTS

| CN | 2601094 Y | 1/2004 |
| CN | 1781477 A | 6/2006 |

(Continued)

OTHER PUBLICATIONS

Pharmaaprroach, "Oral Administration of Drugs: Advantages and Disadvantages", 2020, pp. 1-4. (Year: 2020).*

(Continued)

*Primary Examiner* — Kyung S Chang
(74) *Attorney, Agent, or Firm* — David Postolski; Gearhart Law LLC

(57) ABSTRACT

The present invention relates to the development of a targeted delivery system for the oral delivery of probiotics or therapeutic agent for various indications, including and not limited to active and prophylaxis treatment of *Clostridium difficile* infection, antibiotic associated diarrhea, irritable bowel syndrome, Crohn's disease, intestinal flora replacement, supplemental flora treatments for patients taking antibiotics, and for restoration of balance and signaling between the intestinal microbiome and the intestinal cells in patients under treatment of metabolic syndrome manifestations, specifically diabetes, insulin resistance, obesity, hyperlipidemia and hypertension. The present invention restores altered probiotic organism imbalances that are characteristic of said diseases among others as well as defines a platform technology development for site specific delivery of probiotic organisms in the GI tract of a mammal, most specifically the ileum and/or right colon of a human subject.

14 Claims, 18 Drawing Sheets

Related U.S. Application Data division of application No. 14/771,830, filed as application No. PCT/US2014/027228 on Mar. 14, 2014, now Pat. No. 9,907,755.

(60) Provisional application No. 61/897,378, filed on Oct. 30, 2013, provisional application No. 61/781,810, filed on Mar. 14, 2013.

(51) Int. Cl.
*A61K 35/744* (2015.01)
*A61K 35/745* (2015.01)
*A61K 35/747* (2015.01)

(52) U.S. Cl.
CPC .......... *A61K 9/4891* (2013.01); *A61K 35/741* (2013.01); *A61K 35/744* (2013.01); *A61K 35/745* (2013.01); *A61K 35/747* (2013.01)

(56) References Cited

U.S. PATENT DOCUMENTS

| | | |
|---|---|---|
| 4,256,108 A | 3/1981 | Theeuwes |
| 4,572,833 A | 2/1986 | Pedersen et al. |
| 4,579,734 A | 4/1986 | Hata et al. |
| 4,789,724 A | 12/1988 | Domb et al. |
| 4,839,281 A | 6/1989 | Gorbach et al. |
| 4,857,311 A | 8/1989 | Domb et al. |
| 4,888,176 A | 12/1989 | Langer et al. |
| 5,032,399 A | 7/1991 | Gorbach et al. |
| 5,079,164 A | 1/1992 | Kirkovits et al. |
| 5,176,911 A | 1/1993 | Tosi et al. |
| 5,401,512 A | 3/1995 | Rhodes et al. |
| 5,413,785 A | 5/1995 | Nanji |
| 5,525,634 A | 6/1996 | Sintov et al. |
| 5,541,170 A | 7/1996 | Rhodes et al. |
| 5,573,779 A | 11/1996 | Sato et al. |
| 5,599,795 A | 2/1997 | McCann et al. |
| 5,603,953 A | 2/1997 | Herbig et al. |
| 5,622,721 A | 4/1997 | Dansereau et al. |
| 5,650,170 A | 7/1997 | Wright et al. |
| 5,681,584 A | 10/1997 | Savastano et al. |
| 5,686,105 A | 11/1997 | Kelm et al. |
| 5,733,568 A | 3/1998 | Ford |
| 5,811,128 A | 9/1998 | Tice et al. |
| 5,843,479 A | 12/1998 | Kelm et al. |
| 5,885,590 A | 3/1999 | Hunter et al. |
| 5,900,252 A | 5/1999 | Calanchi et al. |
| 5,962,024 A | 10/1999 | Marvola et al. |
| 6,103,227 A | 8/2000 | Wolf et al. |
| 6,132,710 A | 10/2000 | Panigrahi et al. |
| 6,221,350 B1 | 4/2001 | Brown et al. |
| 6,306,422 B1 | 10/2001 | Batich et al. |
| 6,479,051 B1 | 11/2002 | Bruce et al. |
| 6,506,407 B2 | 1/2003 | Watanabe et al. |
| 6,638,534 B1 | 10/2003 | Ishibashi et al. |
| 6,641,808 B1 | 11/2003 | Bojrab |
| 6,696,057 B1 | 2/2004 | Bojrab |
| 6,746,671 B2 | 6/2004 | Steidler et al. |
| 6,811,786 B1 | 11/2004 | Farmer et al. |
| 6,849,256 B1 | 2/2005 | Farmer |
| 6,861,053 B1 | 3/2005 | Lin et al. |
| 7,081,239 B2 | 7/2006 | Lin |
| 7,094,425 B2 | 8/2006 | Scott et al. |
| 7,101,565 B2 | 9/2006 | Monte |
| 7,192,581 B2 | 3/2007 | Park et al. |
| 7,344,867 B2 | 3/2008 | Connolly |
| 7,410,651 B2 | 8/2008 | Villa et al. |
| 7,431,943 B1 | 10/2008 | Villa et al. |
| 7,601,799 B2 | 10/2009 | Steidler |
| 7,670,612 B2 | 3/2010 | Miller |
| 7,670,617 B2 | 3/2010 | Pather et al. |
| 7,670,627 B2 | 3/2010 | Shefer et al. |
| 7,718,171 B2 | 5/2010 | Flambard |
| 7,731,976 B2 | 6/2010 | Cobb et al. |
| 7,749,494 B2 | 7/2010 | Renaud et al. |
| 7,749,509 B2 | 7/2010 | Cobb et al. |
| 7,759,105 B2 | 7/2010 | Cobb et al. |
| 7,780,961 B2 | 8/2010 | Steidler |
| 7,927,584 B2 | 4/2011 | Allende |
| 7,998,474 B2 | 8/2011 | Kelly |
| 8,029,823 B2 | 10/2011 | Villa et al. |
| 8,066,987 B2 | 11/2011 | Moore et al. |
| 8,092,793 B2 | 1/2012 | Cui |
| 8,168,594 B2 | 5/2012 | Paterson et al. |
| 8,192,733 B2 | 6/2012 | Cobb et al. |
| 8,197,805 B2 | 6/2012 | Lin et al. |
| 8,246,989 B2 | 8/2012 | Dansereau et al. |
| 8,263,146 B2 | 9/2012 | Bengtsson-Riveros et al. |
| 8,293,273 B2 | 10/2012 | Villa et al. |
| RE43,799 E | 11/2012 | Villa et al. |
| 8,323,692 B2 | 12/2012 | Frisbee |
| 8,338,162 B2 | 12/2012 | Igimi et al. |
| 8,361,497 B2 | 1/2013 | Miller |
| 8,367,418 B2 | 2/2013 | Monte et al. |
| 8,440,178 B2 | 5/2013 | Darimont et al. |
| 8,454,949 B2 | 6/2013 | Arigoni et al. |
| 8,460,648 B2 | 6/2013 | Borody |
| 8,481,299 B2 | 7/2013 | Gueniche |
| 8,529,887 B2 | 9/2013 | Schiffrin |
| 8,557,560 B2 | 10/2013 | Martin Jimenez et al. |
| 8,784,888 B2 | 7/2014 | Villa et al. |
| 8,906,668 B2 | 12/2014 | Henn et al. |
| 8,999,721 B2 | 4/2015 | Schentag et al. |
| 9,011,834 B1 | 4/2015 | McKenzie et al. |
| 9,028,841 B2 | 5/2015 | Henn et al. |
| 9,180,147 B2 | 11/2015 | McKenzie et al. |
| 9,241,911 B2 | 1/2016 | Miller |
| 9,370,528 B2 | 6/2016 | Schentag et al. |
| 9,443,060 B2 | 9/2016 | Schentag et al. |
| 9,539,216 B2 | 1/2017 | Miller |
| 9,707,207 B2 * | 7/2017 | Finegold .............. A61K 31/397 |
| 9,757,346 B2 | 9/2017 | Fayad |
| 9,907,755 B2 | 3/2018 | Kabadi et al. |
| 10,369,111 B2 | 8/2019 | Kabadi et al. |
| 2003/0092145 A1 | 5/2003 | Jira et al. |
| 2003/0194428 A1 | 10/2003 | Miller et al. |
| 2003/0194429 A1 | 10/2003 | Miller et al. |
| 2003/0194430 A1 | 10/2003 | Miller et al. |
| 2003/0194431 A1 | 10/2003 | Miller et al. |
| 2004/0062757 A1 | 4/2004 | Finegold |
| 2004/0120931 A1 | 6/2004 | Myatt |
| 2006/0093592 A1 | 5/2006 | Cheruvanky et al. |
| 2006/0210631 A1 | 9/2006 | Patel et al. |
| 2007/0141039 A1 | 6/2007 | Collins et al. |
| 2007/0280911 A1 | 12/2007 | Cobb et al. |
| 2008/0020018 A1 | 1/2008 | Moodley et al. |
| 2008/0233184 A1 | 9/2008 | Looney |
| 2008/0261916 A1 | 10/2008 | Jaszberenyi et al. |
| 2008/0286252 A1 | 11/2008 | Sinnott |
| 2008/0311201 A1 | 12/2008 | Der-Yang et al. |
| 2009/0035370 A1 | 2/2009 | Bortz et al. |
| 2009/0162322 A1 | 6/2009 | Rudolph et al. |
| 2010/0209520 A1 | 8/2010 | Kubo |
| 2010/0221321 A1 | 9/2010 | Miller et al. |
| 2010/0233254 A1 | 9/2010 | Miller |
| 2010/0247489 A1 | 9/2010 | Saur-Brosch |
| 2010/0316617 A1 | 12/2010 | Renaud et al. |
| 2011/0092583 A1* | 4/2011 | Murty .................. A61K 9/4858 514/454 |
| 2011/0268795 A1 | 11/2011 | Fayad |
| 2012/0093923 A1 | 4/2012 | Miller et al. |
| 2012/0183513 A1 | 7/2012 | Neu et al. |
| 2012/0247993 A1 | 10/2012 | Palazzi et al. |
| 2012/0276149 A1 | 11/2012 | Littman et al. |
| 2013/0089524 A1 | 4/2013 | Petit et al. |
| 2013/0136791 A1 | 5/2013 | Miller |
| 2013/0149339 A1 | 6/2013 | Honda et al. |
| 2013/0164380 A1 | 6/2013 | Durum et al. |
| 2013/0266539 A1 | 10/2013 | Borody |
| 2014/0328803 A1 | 11/2014 | McKenzie et al. |
| 2015/0071994 A1 | 3/2015 | Schentag et al. |
| 2015/0190435 A1 | 7/2015 | Henn et al. |

(56) References Cited

U.S. PATENT DOCUMENTS

| | | |
|---|---|---|
| 2015/0352189 A1 | 12/2015 | Schentag et al. |
| 2016/0030494 A1 | 2/2016 | Henn et al. |
| 2016/0040215 A1 | 2/2016 | Henn et al. |

FOREIGN PATENT DOCUMENTS

| | | |
|---|---|---|
| EP | 0587220 A1 | 3/1994 |
| GB | 2238243 A | 5/1991 |
| GB | 2365336 A | 2/2002 |
| GB | 2490671 A | 11/2012 |
| RU | 2442572 C1 | 2/2012 |
| WO | WO-89/11269 A1 | 11/1989 |
| WO | WO-1991/016881 A1 | 11/1991 |
| WO | WO-199535100 A1 | 12/1995 |
| WO | WO-2001051008 A2 | 7/2001 |
| WO | WO-2007013794 A1 | 2/2007 |
| WO | WO-2008/122967 A2 | 10/2008 |
| WO | WO-2008122965 A2 | 10/2008 |
| WO | WO-2010/027498 A2 | 3/2010 |
| WO | WO-2012/077038 A1 | 6/2012 |
| WO | WO-2012/118712 A2 | 9/2012 |
| WO | WO-2013037068 A1 | 3/2013 |
| WO | WO-2013050792 A1 | 4/2013 |
| WO | WO-2013/063527 A1 | 5/2013 |
| WO | WO-2013080561 A1 | 6/2013 |
| WO | WO-2013148258 A1 | 10/2013 |
| WO | WO-2014121298 A2 | 8/2014 |
| WO | WO-2014121301 A1 | 8/2014 |
| WO | WO-2014121302 A2 | 8/2014 |
| WO | WO-2014121304 A1 | 8/2014 |
| WO | WO-2014145958 A2 | 9/2014 |
| WO | WO-2014153194 A2 | 9/2014 |
| WO | WO-2015077794 A1 | 5/2015 |
| WO | WO-2015095241 A2 | 6/2015 |

OTHER PUBLICATIONS

2003) "*Staphylococcus aureus* vaccine conjugate—Nabi: Nabi-Staph VAX, Staph VAX." Drugs R. D., 4(6):383-5.

Akers, S.N. et al. (2010) "Regulation of cancer germline antigen gene expression: implications for cancer immunotherapy," Future Oncol., 6(5):717-32.

Ano, G. et al. (2011) "A new oral vaccine candidate based on the microencapsulation by spray-drying of inactivated Vibrio cholerae," Vaccine. 29(34):5758-64.

Barrera, D.A. et al. (1993) "Synthesis and RGD peptide modification of a new biodegradable copolymer: poly(lactic acid-co-lysine)," J. Am. Chem. Soc., 115(23):11010-11011.

Beagley, K.W. et al. (1988) "Recombinant murine IL-5 induces high rate IgA synthesis in cycling IgA-positive Peyer's patch B cells," J Immunol., 141(6):2035-42.

Boussif, O. et al. (1995) "A versatile vector for gene and oligonucleotide transfer into cells in culture and in vivo: polyethylenimine," Proc. Natl. Acad. Sci. U.S.A., 92(16):7297-301.

Carter, K.C. et al. (2006) "Translation of an experimental oral vaccine formulation into a commercial product." Methods., 38(2):65-8.

Cassilly, D. et al. (2008) "Gastric emptying of a non-digestible solid: assessment with simultaneous SmartPill pH and pressure capsule, antroduodenal manometry, gastric emptying scintigraphy," Neurogastroenterol Motil., 20(4):311-9.

Chavarri et al. (2010) "Microencapsulation of a probiotic and prebiotic in alginate-chitosan capsules improves survival in simulated gastro-intestinal conditions," International Journal of Food Microbiology, 142(1):185-189.

Chen, Y.T. et al. (2009) "Cancer/testis antigen CT45: analysis of mRNA and protein expression in human cancer," Int. J. Cancer., 124(12):2893-8.

Chonn et al. (1995) "Recent advances in liposomal drug-delivery systems," Curr. Opin. Biotechnol., 6(6):698-708.

Clark, S. et al. (2008) "Assessment of different formulations of oral *Mycobacterium bovis* Bacille Calmette-Guerin (BCG) vaccine in rodent models for immunogenicity and protection against aerosol challenge with *M. bovis*," Vaccine, 26(46):5791-7.

Conry, S.J. et al. (2012) "Genetically Associated CD16+56—Natural Killer Cell Interferon (IFN)-alphaR Expression Regulates Signaling and Is Implicated in IFN-alpha-Induced Hepatitis C Virus Decline," J. Infect. Dis., 205(7):1131-41.

Crooks, E.T. et al. (2011) "Enzyme digests eliminate nonfunctional Envfrom HIV-1 particle surfaces, leaving native Env trimers intact and viral infectivity unaffected," J. Virol., 85(12):5825-39.

Delgado, A. et al. (1999) "PLG microparticles stabilised using enteric coating polymers as oral vaccine delivery systems," Vaccine, 17(22):2927-38.

Dewhirst, F.E. et al. (1999) "Phylogeny of the Defined Murine Mircobiota: Altered Schaedler Flora." Applied and Environmental Microbiology, 65(8):3287-3292.

Duijvestijn, A. et al. (1989) "Mechanisms and regulation oflymphocyte migration," Immunol. Today, 10(1):23-8.

Eldridge, J.H. et al. (1989) "Biodegradable microspheres: vaccine delivery system for oral immunization," Curr. Top. Microbiol. Immunol., 146:59-66.

Everson, M.P. et al. (1995) "Dendritic cells regulate development of alloantigenic and mitogenic THI versus TH2 responses," Adv. Exp. Med. Biol., 378:347-9.

Everson, M.P. et al. (1996) "Dendritic cells from different tissues induce production of different T cell cytokine profiles," J. Leukoc. Biol., 59(4):494-8.

Everson, M.P. et al. (1998) "Dendritic cells from Peyer's patch and spleen induce different T helper cell responses," J. Interferon Cytokine Res., 18(2):103-15.

Farstad, I.N. et al. (1993) "Do human Peyer's patches contribute to the intestinal intraepithelial gamma/delta T-cell population?," Scand. J. Immunol., 38(5):451-8.

Farstad, I.N. et al. (1994) "Heterogeneity of M-cell-associated Band T cells in human Peyer's patches," Immunology, 83(3):457-64.

Fattom, A. et al. (2004) "Safety and immunogenicity of a booster dose of *Staphylococcus aureus* types 5 and 8 capsular polysaccharide conjugate vaccine (Staph VAX) in hemodialysis patients," Vaccine, 23(5):656-63.

Fattom, A.I. et al. (2004) "Development of Staph VAX, a polysaccharide conjugate vaccine against *S. aureus* infection: from the lab bench to phase III clinical trials," Vaccine, 22(7):880-7.

Faure, G.C. et al. (1992) "Peripheral blood specific antibody-forming cells after oral stimulation with a ribosomal vaccine," Dev. Biol. Stand., 77:175-81.

Friend, D.R. (2005) "New Oral Delivery Systems for Treatment of inflammatory bowel disease," Advanced Drug Delivery Reviews, 2005:57:247-265.

Geuking, M.B. et al. (2011) "Intestinal Bacterial Colonization Induces Mutualistic Regulatory T Cell Responses," Immunity, 34:794-806.

Gliko-Kabir, I. et al. (1998) "Low swelling, crosslinked guar and its potential use as colon-specific drug carrier," Pharm. Res., 15(7):1019-25.

Goldin, B.R. et al. (2008) "Clinical Indications for Probiotics: An Overview," CID, 46:S96-100.

Grafmueller, S. et al. (2012) "Differential Antigen Specificity of Hepatitis C Virus-Specific Interleukin 17- and Interferon gamma-Producing CD8+ T Cells During Chronic Infection," J. Infect. Dis., 205(7):1142-6.

Gupta, V.K. et al. (2001) "A novel pH-and time-based multi-unit potential colonic drug delivery system. I. Development," International Journal of Pharmaceutics, 213(1-2):83-91.

Haensler, J. et al. (1993) "Polyamidoamine cascade polymers mediate efficient transfection of cells in culture," Bioconjug. Chem., 4(5):372-9.

Halliday, J. et al. (2011) "Vaccination for hepatitis C virus: closing in on an evasive target," Expert Rev. Vaccines, 10(5):659-72.

Halstensen, T.S. et al. (1993) "Gluten stimulation of coeliac mucosa in vitro induces activation (CD25) of lamina propria CD4+ T cells and macrophages but no crypt-cell hyperplasia," Scand. J. Immunol., 38(6):581-90.

(56) References Cited

OTHER PUBLICATIONS

Hamann, A. et al. (1989) "Molecules and regulation in lymphocyte migration," Immunol. Rev., 108:19-44.
Hanninen, A. et al. (1992) "Macrophages, T cell receptor usage, and endothelial cell activation in the pancreas at the onset of insulin-dependent diabetes mellitus," J. Clin. Invest., 90(5):1901-10.
Hanson, L.A. et al. (1993) "The discovery of secretory IgA and the mucosal immune system," Immunol. Today, 14(8):416-7.
Hovgaard and Brøndsted (1995) "Dextran hydrogels for colon-specific drug delivery," Journal of Controlled Release (Proceedings of the Third European Symposium on Controlled Drug Delivery), 36: 159-166.
Huh, K.M. et al. (2012) "pH-Sensitive Polymers for Drug Delivery," Macromolecular Research, 20(3):224-233.
Ivanov, I.I. et al. (2010) "Segmented filamentous bacteria take the stage," Mucosal Immunol., 3(3):209-212.
Jones, T. (2002) "Staph VAX (Nabi)," Curr. Opin. Investig. Drugs., 3(1):48-50.
Kabanov, A.V., et al. (1995) "DNA complexes with polycations for the delivery of genetic material into cells," Bioconjug. Chem., 6(1):7-20.
Kantele, J.M. et al. (1996) "Mucosally activated circulating human B cells in diarrhea express homing receptors directing them back to the gut," Gastroenterology, 110(4): 1061-7.
Khan, M.Z. et al. (1999) "A pH-dependent colon targeted oral drug delivery system using methacrylic acid copolymers. I. Manipulation of drug release using Eudragit® LlOO-55 and Eudragit® SlOO combinations," Journal of Controlled Release, 58:215-222.
Khan, M.Z. et al. (2000) "A pH-dependent colon targeted oral drug delivery system using methacrylic acid copolymers. II. Manipulation of drug release using Eudragit® LlOO Eudragit SlOO combinations," Drug Development and Industrial Pharmacy, 26(5):549-554.
Kim, Y.C. et al. (2010) "Enhanced memory responses to seasonal H1N1 influenza vaccination of the skin with the use of vaccine-coated microneedles," J. Infect. Dis., 201(2):190-8.
Kim, Y.H. et al. (2012) "Diet-induced obesity dramatically reduces the efficacy of a 2009 pandemic H1N1 vaccine in a mouse model," J. Infect. Dis., 205(2):244-51.
Kiyono, H. et al. (1982) "Murine Peyer's patch T cell clones. Characterization of antigenspecific helper T cells for immunoglobulin A responses," J. Exp. Med., 156(4):1115-30.
Kopecek et al. (1992) "Polymers for colon-specific drug delivery," J. Control Release, 19:121-130.
Kozbor, D. (2010) "Cancer vaccine with mimotopes of tumor-associated carbohydrate antigens." Immunol. Res., 46(1-3):23-31.
Krishnamachari, Y. et al. (2007) "Development of pH-and time-dependent oral microparticles to optimize budesonide delivery to ileum and colon," International Journal of Pharmaceuticals, 338:238-247.
Kukowska-Latallo, J.F. (1996) "Efficient transfer of genetic material into mammalian cells using Starburst polyamidoamine dendrimers," Proc. Natl. Acad. Sci. U.S.A., 93(10):4897-902.
Kwon et al. (1989) "Pseudopoly(amino acids): a study of the synthesis and characterization of poly(trans-4-hydroxy-N-acyl-L-proline esters)," Macromolecules, 22(8):3250-3255.
Langer, R. et al. (1976) "Polymers for the sustained release of proteins and other macromolecules," Nature, 263(5580):797-800.
Larhed, A. et al. (2004) "Starch microparticles as oral vaccine adjuvant: antigen-dependent uptake in mouse intestinal mucosa," J. Drug Target., 12(5):289-96.
Lehmann et al. (1991) "Methacrylate-Galactomannan Coating for Colon-Specified Drug Delivery," Proc. Int. Symp. Contr. Rel. Bioact. Mater., 8:331-32.
Li, F.Q. et al. (2007) "Oral vaccination and vaccine-entrapped microparticle delivery system," Yao Xue Xue Bao., 42(3):245-51.
Li, J. et al. (2002) "In Vitro Evaluation of Dissolution Behavior of a Colon-Specific Drug Delivery System (CODES™) in Multi-pH Media USign United States Pharmacopeia Apparatus II and III," AAPS PharmSciTech, 3(4):E33.
Li, Q. et al. (2010) "Antigen-induced Erkl/2 activation regulates Ets-1-mediated sensitization of CD8+ T cells for IL-12 responses," J. Leukoc. Biol., 87(2):257-63.
Lim et al. (1999) "A Self-Destroying Polycationic Polymer: Biodegradable Poly(4-hydroxy-l-proline ester)," J. Am. Chem. Soc., 121(24):5633-5639.
Louie, J.K. et al. (2011) "A novel risk factor for a novel virus: obesity and 2009 pandemic influenza A (H1N1)," Clin. Infect. Dis., 52(3):301-12.
Malaspina, A. et al. (2002) "Human immunodeficiency virus type 1 bound to B cells: relationship to virus replicating in CD4+ T cells and circulating in plasma," J. Virol., 76(17):8855-63.
Mhawech-Fauceglia, P. et al. (2008) "Prostate-specific membrane antigen expression is a potential prognostic marker in endometrial adenocarcinoma," Cancer Epidemiol. Biomarkers Prev., 17(3):571-7.
Milojevic et al. (1993) "In Vitro and In Vivo Evaluation of Amylose Coated Pellets for Colon Specific Drug Delivery," Proc. Int. Symp. Contr. Rel. Bioact. Mater., 20:288-89.
Moir, S. et al. (2003) "Perturbations in B cell responsiveness to CD4+ T cell help in HIV infected individuals." Proc. Natl. Acad. Sci. U.S.A., 100(10):6057-62.
Moir, S. et al. (2008) "Evidence for HIV-associated B cell exhaustion in a dysfunctional memory B cell compartment in HIV-infected viremic individuals," J. Exp. Med., 205(8):1797-805.
Moir, S. et al. (2008) "Normalization of B Cell Counts and Subpopulations after Antiretroviral Therapy in Chronic HIV Disease" JID, 197: 572-579.
Moir, S. et al. (2009) "B cells in HIV infection and disease," Nat. Rev. Immunol., 9(4):235-45.
Moir, S. et al. (2011) "Pathogenic mechanisms of HIV disease," Annu. Rev. Pathol., 6:223-48.
Moir, S. et al. (2011) "Prospects for an HIV vaccine: leading B cells down the right path," Nat. Struct. Mol. Biol., 18(12):1317-21.
Muller, F. et al. (1992) "Nonspecific oral immunity in individuals with HIV infection," J. Acquir. Immune. Defic. Syndr., 5(1):46-51.
Na, Kun et al. (2005) "pH-Sensitive Polymers for Drug Delivery," 129-194.
Nilssen, D.E. et al. (1993) "B-cell activation in duodenal mucosa after oral cholera vaccination in IgA deficient subjects with or without IgG subclass deficiency," Scand. J. Immunol., 38(2):201-8.
Nilssen, D.E. et al. (1993) "Duodenal intraepithelial gamma/delta T cells and soluble CD8, neopterin, and beta 2 microglobulin in serum of IgA-deficient subjects with or without IgG subclass deficiency," Clin. Exp Immunol., 94(1):91-8.
Odunsi, K. et al. (2003) "NY-ES0-1 and LAGE-I cancer-testis antigens are potential targets for immunotherapy in epithelial ovarian cancer," Cancer Res., 63(18):6076-83.
Petrof, E.O. et al. (2013) "Stool substitute transplant therapy for the eradication of Clostridium difficile infection: 'RePOOPulating'the gut," Microbiome, 1(3):1-12.
Plummer et al. (2004) "Clostridium difficile pilot study: effects of probiotic supplementation on the incidence of C. difficile diarrhoea," International Microbiology, 7(1): 59-62.
Pniewski, T. et al. (2011) "Low-dose oral immunization with lyophilized tissue of herbicideresistant lettuce expressing hepatitis B surface antigen for prototype plant-derived vaccine tablet formulation." J. Appl. Genet., 52(2):125-36.
Pniewski, T. et al. (2012) "Plant expression, lyophilisation and storage of HBV medium and large surface antigens for a prototype oral vaccine formulation," Plant Cell Rep., 31(3):585-95.
Prabakaran, M. et al. (2010) "Reverse micelle-encapsulated recombinant baculovirus as an oral vaccine against H5N1 infection in mice," Antiviral Res., 86(2):180-7.
Putnam, D. et al. (1999) "Poly(4-hydroxy-L-proline ester): Low-temperature Polycondensation and Plasmid DNA Complexation," Macromolecules, 32:3658-3662.
Qian, F. et al. (2005) "Tumor associated antigen recognition by autologous serum in patients with breast cancer," Int. J. Mol. Med., 15(1):137-44.

(56) References Cited

OTHER PUBLICATIONS

Raghuraman S. et al. (2012) "Spontaneous clearance of chronic hepatits C virus infection is associated with appearance of neutralizing antibodies and reversal of T-cell exhaustion," J. Infect. Dis., 205(5)763-71.
Rahman, F. et al. (2004) "Effects of antiviral therapy on the cellular immune response in acute hepatitis C," Hepatology, 40(1):87-97.
Rajkannan, R. et al. (2006) "Development of hepatitis B oral vaccine using B-cell epitope loaded PLG nanoparticles," Vaccine, 24(24):5149-57.
Rao, S.S. et al. (2009) "Investigation of colonic and whole-gut transit with wireless motility capsule and radiopaque markers in constipation," Clin. Gastroenterol. Hepatol., 2009;7(5):537-44.
Rescia, V.C. et al. (2011) "Dressing liposomal particles with chotsan and poly(cinylic alcohol) for oral vaccine delivery," J. Liposome Res., 21(10):38-45.
Ringel et al. (2012) "Using probiotics in Gastrointestinal disorders," Am. J. Gastroenterol. Suppl., 1:34-40.
Rognum, T.O. et al. (1992) "Development of intestinal mucosal immunity in fetal life and the first postnatal months," Pediatr. Res., 32(2):145-9.
Rubinstein, A. et al. (1992) "Colonic drug delivery: enhanced release of indomethacin from cross-linked chondroitin matrix in rat cecal content," Pharm. Res., 9(2):276-8.
Rubinstein, A. et al. (1993) "In vitro evaluation of calcium pectinate: a potential colon-specific drug delivery carrier," Pharm. Res., 10(2):258-63.
Scott et al. (1993) "The immune system of the gastrointestinal tract," Pediatr. Allergy Immunol., 4(3 Suppl):7-15.
Segal, B.H. et al. (2006) "Heat shock proteins as vaccine adjuvants in infections and cancer," Drug Discov. Today., 11(11-12):534-40.
Shamsuzzaman, S. et al. (2009) "Robust gut associated vaccine-specific antibody-secreting cell responses are detected at the mucosal surface of Bangladeshi subjects after immunization with an oral killed bivalent V. cholerae O1/O139 whole cell cholera vaccine: comparison with other mucosal and systemic responses," Vaccine, 27(9): 1386-92.
Siefke, et al. (1994) "Colon Targeting with β-CD Matrix Films," Eur. J. Pharm. Biopharm., 40(suppl.):33S.
Sovran, L. (2009) "World Vaccine Congress Lyon—Terrapinn's 11th Annual Congress," IDrugs, 12(12)738-41.
Spalding, D.M. et al. (1983) "Accessory cells in murine Peyer's patch. I. Identification and enrichment of a functional dendritic cell," J. Exp. Med., 157(5):1646-59.
Spalding, D.M. et al. (1984) "Peyer's patch dendritic cells: isolation and functional comparison with murine spleen dendritic cells," Immunobiology, 168(3-5):380-90.
Spalding, D.M. et al. (1984) "Preferential induction of polyclonal IgA secretion by murine Peyer's patch dendritic cell-T cell mixtures," J. Exp. Med., 160(3):94I-6.

Strickland, G.T. et al. (2008) "Hepatitis C vaccine: supply and demand," Lancet Infect. Dis., 8(6):379-86.
Tammela, J. et al. (2004) "SCP-I cancer/testis antigen is a prognostic indicator and a candidate target for immunotherapy in epithelial ovarian cancer," Cancer Immun., 4:10.
Tang, M.X. et al. (1996) "In vitro gene delivery by degraded polyamidoamine dendrimers," Bioconjug Chem., 7(6):703-14.
Theilacker, C. et al. (2012) "Protection Against *Staphylococcus aureus* by Antibody to the Polyglycerolphosphate Backbone of Heterologous Lipoteichoic Acid," J. Infect. Dis., 205(7):1076-85.
Tomaras, G.D. et al. (2011) "Polyclonal B cell responses to conserved neutralization epitopes in a subset of HIV-I-infected individuals," J. Virol., 85(21): 11502-19.
Toorisaka, E. et al. (2005) "An enteric-coated dry emulsion formulation for oral insulin delivery," J. Control. Release, 107(10):91-96.
Torii, M. et al. (1981) "Lymphoid cell responses to bacterial cell wall components: polyclonal and immune responses of murine B cells to *Streptococcus mutans* carbohydrate antigens," J. Immunol., 127(5):2106-12.
Tsuji, T. et al. (2011) "Antibody-targeted NY-ESO-1 to mannose receptor or DEC-205 in vitro elicits dual human CD8+ and CD4+ T cell responses with broad antigen specificity," J. Immunol., 186(2):1218-27.
Tsuji, T. et al. (2011) "Split T cell tolerance against a self/tumor antigen: spontaneous CD4+ but not CD8+ T cell responses against p53 in cancer patients and healthy donors," PLoS One, 6(8):e23651.
Ubeda, C. et al. (2013) "Intestinal Microbiota Containing *Barnesiella* Species Cures Vancomycin-Resistant Enterococcus faecium Colonization," Infection and Immunity, 81(3):965-973.
Wang, X.Y. et al. (2001) "Characterization of heat shock protein 110 and glucose-regulated protein 170 as cancer vaccines and the effect of fever-range hyperthermia on vaccine activity," J. Immunol., 166(1):490-7.
Weisman, L.E. (2007) "Antibody for the prevention of neonatal noscocomial *Staphylococcal* infection: a review of the literature," Arch. Pediatr., 14 Suppl I:S31-4.
Woloszynska-Read, A. et al. (2010) "BORIS/CTCFL expression is insufficient for cancer germline antigen gene expression and DNA hypomethylation in ovarian cell lines," Cancer Immun., 10:6.
Woloszynska-Read, A. et al. (2011) "Coordinated cancer germline antigen promoter and global DNA hypomethylation in ovarian cancer: association with the BORIS/CTCF expression ratio and advanced stage," Clin. Cancer Res., 17(8):2170-80.
Zauner, W. et al. (1998) "Polylysine-based transfection systems utilizing receptor-mediated delivery," Adv. Drug Deliv. Rev., 30(1-3):97-113.
Zhou et al. (1990) "Preparation of poly(L-serine ester): a structural analog of conventional poly(L-serine)," Macromolecules, 23(14):3399-3406.
U.S. Appl. No. 14/387,979, Gastrointestinal Site-Specific Oral Vaccination Forumulations Active on the Ileum and Appendix, filed Sep. 25, 2014.

* cited by examiner

TARGETED GASTROINTESTINAL TRACT DELIVERY OF PROBIOTIC ORGANISMS AND/OR THERAPEUTIC AGENTS

CROSS REFERENCE TO RELATED APPLICATIONS

This application is a continuation of U.S. patent application Ser. No. 15/874,543, filed on Jan. 18, 2018, which is a divisional of U.S. patent application Ser. No. 14/771,830, filed on Sep. 1, 2015, now U.S. Pat. No. 9,907,755, which is filed under the provisions of 35 U.S.C § 371 and claims the priority of International Patent Application No. PCT/US2014/027228 filed on Mar. 14, 2014, which in turn claims priority to U.S. Provisional Application No. 61/781,810 filed on Mar. 14, 2013, and U.S. Provisional Application No. 61/897,378 filed on Oct. 30, 2013, the contents of which are incorporated by reference herein for all purposes.

FIELD OF THE INVENTION

The present invention relates to the development of platform technology for targeted, controlled delivery of oral enhanced probiotics for various indications, including for example the active and prophylaxis treatment of *Clostridium difficile* Infection as well as Metabolic syndrome and type 2 diabetes.

BACKGROUND OF THE INVENTION

The following includes information that may be useful in understanding the present inventions. It is not an admission that any of the information provided herein is prior art, or relevant, to the presently described or claimed inventions, or that any publication or document that is specifically or implicitly referenced is prior art.

Recent studies have highlighted the importance of the human microbiome in health and disease. However, for the most part the mechanisms by which the microbiome mediates disease, or protection from it, remain poorly understood. Hajishengallis and colleagues have been developing the Keystone-pathogen hypothesis, which highlights the important interactions between flora normally found in healthy humans, diseases associated with alterations in these flora, and the role of the host inflammatory system in the transition between health and a disease state (1). The keystone-pathogen hypothesis holds that certain low-abundance microbial pathogens can orchestrate inflammatory diseases, by remodeling a normally benign microbiota into a dysbiotic one. Hajishengallis and colleagues critically assess the available literature that supports the keystone hypothesis, which may provide a novel conceptual basis for the development of targeted diagnostics and treatments for complex dysbiotic diseases. This work provides an elementary background understanding for use of specific organisms delivered to specific sites in the Gastro-intestinal tract, which is the subject of the instant invention.

As currently understood, probiotics are live non-toxic microbial food supplements that can beneficially affect a host by improving the host's intestinal microbial balance without causing disease. Because probiotic organisms may be altered by antibiotic treatments or for other reasons, they do not permanently colonize in the body. It is therefore important that they be ingested regularly for their health-promoting effects to persist. After ingestion, probiotics typically adhere to a tissue of the host, such as the wall of the intestine or the vagina. Once attached, the desirable bacteria are capable of multiplying and colonizing, thereby enhancing optimal microflora balance. They are used to promote healthy microflora ('good bacteria "or commensals) balance (good or eubiosis) in the lower GI tract and healthy pH balance (yeast fungus) in the oral cavity, large intestine and vaginal tract and minimize microbial imbalance or dysbiosis. Probiotics characteristics are the following: (1) from human origin; (2) stable and viable, gastric and bile acid resistant; (3) effectively adhere to and colonizing at the site of action; (4) compete with pathogens for adhesion sites; and (5) produce pathogen inhibitory substances, e.g. bacteriocidins and organic acids.

Probiotics provide: (1) normalization of flora (e.g., suppress PPMs, provide for intestinal mucosal integrity, regulation of bowel movement, IBS, etc.); (2) Immunomodulation (e.g., strengthen immunity, alleviate food allergy symptoms, control of IBD, etc.); (3) Metabolic effects (e.g., Production of vitamins to improve digestion, minimize lactose intolerance, lower cholesterol, promote bile acid deconjugates, etc.) and many other benefits. Probiotics are sometimes combined with prebiotics (combination is called Symbiotic) which are range of range of non-digestible dietary supplements, which modify the balance of the intestinal micro flora, stimulating the growth and/or activity of beneficial microorganisms and suppressing potentially deleterious microorganisms. The supplements include oligosaccharides (fructo-oligosaccharides, galacto-oligosaccharides); Inulin, Lactulose, Lactitol and a few select bacterial strains that produce bifidogenic nutrients. In particular, prebiotics promote the proliferation of Bifidobacteria in the colon and also promote the proliferation of Lactobacilli in the small intestine to a certain extent.

There are many nutritional probiotics products currently available and are marketed as dietary supplements with very soft DSHEA type "support health" benefit claims. Probiotic products are marketed in all different types of dosage forms, by way of example liquids, capsules, enteric coated tablets and matrix sustained release formulations for oral administration. They use different mix of bacteria and sometimes are enteric coated and of the type which are conventionally released into duodenal target and would not survive transit to reach the potential target organs, e.g., colon. The normal pH profile of the GI tract changes (up and down) from the stomach to the colon, e.g. the pH of the stomach, duodenum, ileum and colon is in the range of 1-4, 5.5-6, 7.3-8.0 and 5.5-6.5, respectively. In some diseases conditions the pH of the GI tract may be modified, e.g. pH of the ileum in normal is 7.5 to 8.2, while pH of the ileum in Metabolic Syndrome, Type 2 diabetes and Obese subjects is 7.3 to 7.5, as discovered using the SmartPill to examine distal intestinal pH values in health and diseases.

To date it is assumed that there are no published reports of any kind that support any specific US FDA approved clinical efficacy or safety claims, nor delivery to any specific area or specific benefits of the probiotics. All of the current evidence is generated from different systems and has not been utilized for a practical treatment regimen that is directed toward flora replacement strategy prior to our foundation discoveries in Roux-en-Y gastric bypass (RYGB) patients (3). Likewise, no product currently exists that specifically delivers the probiotic organism(s) at the target specific pH of the colon at pH 5.5-6.2. Most of the enteric products release the probiotic to the duodenum at pH 5.5-6.2 and because of degradation in the proximal intestine, organisms released may never actually reach the ileum or the right sided colon. Accordingly, it would be advantageous to develop a platform technology for controlled delivery formulation of oral enhanced probiotics that specifically target to release in the pH environment of the ileum and the colon, for treatment/cure of various diseases (pill in a pill concept). These include the active and prophylaxis treatment for *Clostridium difficile* infection, and possible treatments of metabolic syndrome in diabetes.

SUMMARY OF THE INVENTION

In a first aspect, the invention provides one or more species of microencapsulated live probiotic organisms that have a biphasic release profile in a subject. The one or more species of microencapsulated live probiotic organisms provided herein may be in the form of a formulation (e.g. in the form of a tablet, capsule, or the like), wherein the formulation comprises one, or more than one species of bacteria that are normally present in the intestine of a subject.

In certain preferred embodiments, this biphasic release profile has a release profile in a subject such that living organisms are first released in a subject at pH values between about 7.0 and 8.0, and secondly to the first release, living organisms are subsequently released at pH values of between about 5.5 and 6.0.

In another aspect, the invention provides microencapsulated live probiotic organisms that have a release profile that targets replacement or revision of one or more species of live bacteria at a pre-determined location within the gastrointestinal tract of a mammal. As will be described in greater detail herein below certain embodiments are provided wherein the pre-determined location within the gastrointestinal tract is the ileum or colon and other embodiments wherein the formulations provided have a pH dependent preferential release and site specific release of a probiotic organism in the intestinal tract of a mammal. Said organism replacements may be made specifically to modify the course of metabolic syndrome associated diseases such as obesity, type 2 diabetes, or the like. Said organism replacements may also be made in other preferred embodiments of the invention to repair intestinal dysbiosis associated diseases, such as, Antibiotic associated diarrhea (AAD), *Clostridium difficile* associated diarrhea (CDAD), metabolic syndrome, etc. Each of these conditions will require specific microbiome replacements or restorations as will be disclosed herein.

In one preferred embodiment provided herein, the microencapsulated live probiotic organisms having a release profile in which one or more species of live probiotic organisms is released in the into the ileum of a subject in an area having a pH of from about 7 to 8.

In another aspect, the probiotic organism provided in certain embodiments is a mixture of bacterial genera in the amounts that are reflective of the mixture of strains derived from the ileum of a normal human, in amounts that replace these genera reflective of normal intestinal balance. Typically, the number of said organisms released is more than $10^5$ and less than $10^{12}$, where the probiotic organism is a mixture of bacterial genera that is reflective of the mixture of strains derived from the stool of a normal human, but it is appreciated that these numbers are not limiting and that lower of higher amounts of any live organism that is administered may be lower or higher than these amounts.

In another aspect, compositions and methods are provided to ameliorate the imbalance of *Clostridium difficile* in a subject suffering from such an imbalance. Accordingly, in certain embodiments, one or more species of microencapsulated live probiotic organisms having a biphasic release profile results in a release of these live probiotic organisms into the distal segments of the gastrointestinal tract, including the ileum and colon of a subject, in order to ameliorate the imbalance of *Clostridium difficile* in a subject suffering from such an imbalance.

In another aspect, formulations are provided herein for the protection of the live probiotic organisms from the digestive actions of the stomach, duodenum, and jejunum of the intestine. Accordingly, some embodiments provide one or more species of microencapsulated live probiotic organisms as a formulation that provides protection of the live probiotic organisms from the digestive actions of the stomach, duodenum, and jejunum of the intestine, such that the desired number of organisms is administered to the ileum of a subject.

In some embodiments, formulations provided herein comprise an encapsulated live probiotic from which one or more probiotic bacteria are dispersed, the encapsulated probiotic comprising a coating comprising "polymers". In certain embodiments, a live bacterial suspension including species from one or both of the genus's *Lactobacillus* and *Bifidobacterium* is provided. In alternative embodiments, live bacterial suspensions including species from one or both of the genus's *Lactobacillus* and *Bifidobacterium* and further comprising the organism *Faecalibacterium prausnitzii* are provided. In yet another alternative embodiment, live bacterial suspensions including species from one or both of the genus's *Lactobacillus* and *Bifidobacterium* and further comprising the organism *Bacteroides thetaiotaomicron* are provided.

In yet another aspect, one or more species of microencapsulated live probiotic organisms are provided in which the microencapsulated live probiotic organisms have a three phase release profile. Accordingly, in a fundamental embodiment of this aspect of the invention, one or more species of microencapsulated live probiotic organisms are provided wherein the microencapsulated live probiotic organisms have a three phase release profile in a subject in which living organisms are released in a subject i) at pH values between about 5.5-6.2 such that the live probiotic organisms are released in the duodenum, ii) at pH values between about 7.2-7.5 such that the live probiotic organisms are released in the ileum, and iii) at pH values between about 5.6-6.2 such that the live probiotic organisms are released in the colon.

In certain preferred variations of embodiments provided above, it is further desirable that none of the bacterial organisms are released in the small intestine at pH values below 6.9 or above 8.1. Thus, the area of release will be within the intestinal tract that includes a high level of Peyer's Patches, that being the ileum.

In another variation of the fundamental embodiment provided above, there i) is an outer layer of microencapsulated probiotic organisms with release characteristics between pH values of 7.0 to 8.0, and ii) a protected inner core of microencapsulated probiotic organisms that are released at pH values below pH of 6.9. This will allow the probiotic to be released in the ileum and colon of the subject.

In certain embodiments, one or more species of microencapsulated live probiotic organisms are provided where the organism specifically stimulates L-cell expression of proteins, hormones or biomarkers of L-cell actions therefrom. In additional embodiments, one or more species of microencapsulated live probiotic organisms are provided wherein the probiotic organisms specifically metabolize bile acids in the distal intestine of the mammal, and where the formulation has beneficial actions on cholesterol and triglyceride concentrations in a mammal.

In still another aspect of the invention, methods of treatment of a subject are provided (e.g. a mammal or human).

Accordingly, in certain embodiments a method of treating a *Clostridium difficile* associated intestinal disorder in a subject is provided in which said method comprises administering a formulation claimed or otherwise provided herein in an amount sufficient to alleviate the disorder being treated in a subject. A *Clostridium difficile* associated disorder treated by the formulation and methods provided herein may be associated with one or more of a *Clostridium difficile* infection, an imbalance of *Clostridium difficile* in the ileum or colon of said subject, diarrhea, inflammation, colitis fever, or the like. Administration of the formulations by methods provided herein alleviates one or more of the preceding signs and symptoms of infection with *Clostridium difficile*. It is preferable that such treatment results in the prophylaxis or prevention of a *Clostridium difficile* infection.

In another aspect, kits comprising one or more species of encapsulated microorganisms and formulations of the same are provided herein. Accordingly, some embodiments of the invention are directed to a kit comprising encapsulated microorganisms and formulations claimed or otherwise provided herein in the form of a tablet, pill, capsule or sachet of microgranules in combination with instructions for administration of the formulation to a subject for the treatment of a disorder. Certain preferred embodiments of the kit are designed for the treatment of a *Clostridium difficile* associated disorder in a subject suffering from such a disorder.

In yet another aspect, kits containing one or more species of encapsulated microorganisms and formulations of same are provided with instructions to patients in need of the procedure termed "fecal transplant" wherein the microgranules of the present invention and formulations are provided herein in the form of a tablet, pill, or capsule in combination with instructions for administration of the formulation to a subject in need of a fecal transplant. Certain preferred embodiments of said kit are designed for the treatment of a *Clostridium difficile* associated disorder in a subject suffering from such a disorder.

Microencapsulated live probiotic organisms and formulations thereof are provided herein in various dosage forms, and they can be co-administered with drugs, foods, nutrients, vitamins, other beneficial substances, prebiotics, and other therapeutic agents such as pH encapsulated glucose, lipids or proteins that release in the distal small intestine at pH values between 7.0 and 8.0 in an amount sufficient to alleviate said disorder in a subject. Preferably, at least two coating are used to cover a tablet or capsule like form comprising the probiotic organism, wherein the outside coating is degraded in a pH environment of 5 to 6 and the inside coating is degraded in a pH environment of about 7 thereby dropping the probiotics in the ileum area and in close proximity to the Peyer's Patches.

In certain embodiments, microencapsulated live probiotic organisms and formulations thereof are administered in conjunction with one or more antibiotic. The dosage formulation is designed in these embodiments to completely separate the antibiotic from the bacteria, and testing is conducted to verify complete separation on a long term basis. Suitable antibiotics include, but are not limited to, vancomycin, metronidazole, gentamicin, colistin, fidaxomicin, telavancin, oritavancin, dalbavancin, daptomycin. An exemplary embodiment is directed to one or more species of microencapsulated live probiotic organisms claimed or otherwise provided herein in a dosage of between $10^5$ and $10^{12}$ CFU, wherein the dosage unit of the formulation contains vancomycin at a dose of between about 125 mg to about 4000 mg, wherein the antibiotics released from each dosage unit formulation at between about pH 1.0 to about pH 6.0.

In certain embodiments, microencapsulated live probiotic organisms and formulations thereof are co-administered with vancomycin in an effective amount for the beneficial treatment of *Clostridium difficile* infection or complications thereof.

In still another aspect, the microencapsulated live probiotic organisms claimed or otherwise provided herein are used for the treatment of other disorders. In non-limiting but preferred embodiments described herein, antibiotics are not included in the formulation.

One embodiment is directed to a method of treating an obesity-associated intestinal disorder in a subject, where the method comprises administering a probiotic formulation targeted to the ileum and right colon which is claimed or otherwise provided herein an amount sufficient to alleviate the disorder in said subject. Another embodiment is directed to a method of treating type 2 diabetes associated metabolic syndrome, where the method comprises administering a probiotic formulation targeted to the ileum and right colon which is claimed or otherwise provided herein an amount sufficient to alleviate the disorder in said subject. In a variation of this embodiment, the organism(s) being used are capable of signaling the release of GLP-1, PYY, GLP-2 or other beneficial peptides from the L-cell target site in the intestine, whereby the disease or condition or metabolic syndrome is modified beneficially. An example of this modification is the treatment of type 2 diabetes with said probiotic formulation in combination with an ileal brake hormone releasing substance active at the ileal brake, where both active moieties act to stimulate L-cell hormone release and to revise signaling of hormones. Replacement of numbers and specific species of probiotic organisms in targeted ileum and colon produces homeostatic and beneficial regulation of L-cell hormone release from the ileum and right sided colon. These novel approaches to treatment are disclosed herein in specific examples.

Another preferred embodiment includes treatment with an anti-diabetic drug, an ileal brake hormone releasing substance and a probiotic organism, wherein said probiotic organism replacement or revision is directed to one or more species of microencapsulated live probiotic organisms claimed or otherwise provided herein in a dosage of between $10^5$ and $10^{12}$ CFU, wherein the dosage unit of the formulation contains metformin at a dose of between about 250 mg to about 1000 mg, wherein the metformin released is from each dosage unit formulation at between about pH 1.0 to about pH 6.0. In certain embodiments, microencapsulated live probiotic organisms and formulations thereof are co-administered with metformin in an effective amount and are co-administered with about 5.0 gm to about 10.0 grams of microgranules of dextrose and nutritional substances, as disclosed in US20110268795, said formulation encapsulated for release at intestinal pH between 7.0 and 7.5, said combination disclosed herein known to be beneficial in the treatment of Type 2 diabetes, metabolic syndromes or complications thereof.

Another embodiment is directed to one or more species of microencapsulated live probiotic organisms claimed or otherwise provided herein in a dosage of between $10^5$ and $10^{12}$ CFU, wherein the dosage unit of the formulation contains atorvastatin at a dose of between about 10 mg to about 80 mg, wherein the atorvastatin released is from each dosage unit formulation at between about pH 1.0 to about pH 6.0. In certain embodiments, microencapsulated live probiotic organisms and formulations thereof are co-administered with atorvastatin in an effective amount and are co-administered with about 5.0 grams to about 10.0 grams of microgranules of dextrose and nutritional substances, as disclosed in US20110268795, said formulation encapsulated for release at intestinal pH between 7.0 and 7.5, said combination disclosed herein known to be beneficial in the treatment of Type 2 diabetes, hyperlipidemia, metabolic syndrome or complications thereof.

In certain preferred embodiments, microencapsulated live probiotic organisms and formulations thereof are co-administered with Tumor Necrosis Factor (TNF) antagonist in an effective amount encapsulated for release at intestinal pH between 7.0 and 7.5, said combination disclosed herein known to be beneficial in the treatment of Crohn's disease, Ulcerative colitis, inflammatory bowel disease or the like, or complications thereof.

Another embodiment is directed to a method of treating irritable bowel diseases associated with dysbiosis, where the method comprises administering a probiotic formulation targeted to the ileum and right colon which is claimed or otherwise provided herein an amount sufficient to alleviate the disorder in said subject. In certain embodiments the microencapsulated live probiotic organisms and formulations thereof are co-administered with drug treatments approved for treatment of irritable bowel diseases, such as linaclotide. Non-limiting examples of irritable bowel diseases and treatments thereof are contained within these embodiments.

Yet another aspect of the present invention is an oral delivery system that delivers a probiotic formulation targeted to the ileum and right colon of a subject; the system comprising:
 a core comprising a probiotic formulation; and
 a coating which encapsulates the probiotic formulation, which is substantially insoluble at a pH of less than a range of between about 7.0 to about 8.0 and soluble in the pH range of about 7.0 to about 8.0, and wherein the probiotic formulation is not released until the pH is about 7 and there is essentially no loss of the probiotic formulation through the digestive tract until the delivery systems reaches the ileum.

Preferably, the coating is comprised of one or more compositions selected from the group consisting of poly(dl-lactide-co-glycolide, chitosan (Chi) stabilized with PVA (poly-vinylic alcohol), a lipid, an alginate, carboxymethyl-ethylcellulose (CMEC), cellulose acetate trimellitate (CAT), hydroxypropylmethyl cellulose phthalate (HPMCP), hydroxypropylmethyl cellulose, ethyl cellulose, color con, food glaze and mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, and copolymers of methacrylic acid and ethyl acrylate to which a monomer of methylacrylate has been added during polymerization, In yet another aspect, the present invention provides for an oral delivery system for delivering a probiotic formulation targeted to the ileum and proximal colon of a subject; the system comprising:
 a core comprising a probiotic formulation wherein the probiotic formulation is included in a biodegradable first capsule that is coated with a first enteric coating that encapsulates the first capsule containing the probiotic formulation, and wherein the first enteric coating solubilizes in a pH of about 6.2 to about 6.5; and
 a second capsule sized to include the coated first capsule, wherein the second capsule is fabricated of a biodegradable material and wherein the second capsule is coated with a second enteric coating that solubilizes in a pH of about 7 to 8, wherein the second capsule releases the first capsule in the ileum and once released the first capsule is solubilized in the proximal colon at a pH of about 6.2 to about 6.5 with the release of the desirable bacteria.

Importantly, the second enteric coating is substantially insoluble at a pH of less than a range of between about 7.0 to about 8.0 and soluble in the pH range of about 7.0 to about 8.0. The first and second enteric coatings are comprised of one or more compositions selected from the group consisting of copolymers of methacrylic acid and ethyl acrylate, and copolymers of methacrylic acid and ethyl acrylate to which a monomer of methylacrylate has been added during polymerization. Notably, the second capsule releases the first capsule in the ileum and once released the first capsule is solubilized in the proximal colon at a pH of about 6.2 to about 6.5 with the release of the probiotic formulation.

The probiotic formulation comprises at least one species of bacteria, preferably from 1 to 30, and more preferably from about 10 to 25 different species or strains, that are normally present in a pre-determined location within the gastrointestinal tract of a subject and preferably the pre-determined location is the ileum or colon. The species of bacteria may be different or just include different strains. The probiotic formulation comprises a mixture of bacterial genera that is reflective of the mixture of strains derived from the ileum of a normal human, and the number of said organisms released is more than $10^6$ and less than $10^{12}$. Preferably, the release of the probiotic formulation is in the distal segments of the gastrointestinal tract including the ileum and colon of a subject and to ameliorate the imbalance of *Clostridium difficile* in a subject suffering from such an imbalance. An effective probiotic formulation comprises a live bacterial suspension selected from the genus *Lactobacillus* and *Bifidobacterium*. Such a formulation may further comprise the organism *Faecalibacterium prausnitzii*.

The probiotic formulation can be combined with drugs, acetaminophen, foods, nutrients, vitamins, beneficial substances, prebiotics, pH encapsulated glucose, lipids or proteins that release in combination with the probiotics or in a pH of from about 1 to 6 and before the release of the probiotics. Also the probiotic formulation may also be co-administered with an antibiotic selected from the group consisting of vancomycin, metronidazole, gentamicin, colistin, fidaxomicin, telavancin, oritavancin, dalbavancin and daptomycin. Still further the probiotic formulation may be combined with an ileal brake hormone releasing substance active at the ileal brake to stimulate L-cell hormone release and to revise signaling of hormones.

The probiotic formulation may be used to modify the course of metabolic syndrome associated diseases selected from the group consisting of obesity and type 2 diabetes; or to repair intestinal dysbiosis associated diseases selected from the group consisting of Antibiotic associated diarrhea (AAD), *Clostridium difficile* associated diarrhea (CDAD) and metabolic syndrome.

The probiotic formulation may also be combined with an anti-diabetic drug, such as metformin; a statin, such as atorvastatin; or an anti-inflammatory, such as a Tumor Necrosis Factor (TNF) antagonist.

Another aspect of the present invention provides for a capsule-in-capsule oral delivery system that delivers desirable probiotics or therapeutic agents to the ileum and/or proximal colon, the system comprising:
 a first capsule containing the desirable probiotics or therapeutic agents, wherein the first capsule is fabricated of a biodegradable material and wherein the first capsule is coated with a first enteric coating that solubilizes in a pH of about 6.2 to about 6.5; and a second capsule being of a size that can include within its dimensions the coated first capsule, wherein the second capsule is fabricated of a biodegradable material and wherein the second capsule is coated with a second enteric coating that solubilizes in a pH of about 7 to 8, wherein the second capsule releases the first capsule in the ileum and once released the first capsule is solubilized in the proximal colon at a pH of about 6.2 to about 6.5 with the release of the desirable probiotics or therapeutic agents.

Notably, the second capsule may further comprise desirable probiotics for release in the ileum. Importantly, the desirable probiotics or therapeutic agents within the capsule system are delivered to the ileum and/or proximal colon without leakage of such probiotics or therapeutic agents in the proximal areas of the gastrointestinal tract positioned before the ileum and/or proximal colon. The present system provides for at least 90% of the desirable probiotics or therapeutic agents to reach the ileum and/or right colon, more preferably at least 95%, and most preferably at least 97%.

The first and second enteric coatings of the capsule-in-capsule oral delivery system are preferably selected from the group consisting of copolymers of methacrylic acid and ethyl acrylate, and copolymers of methacrylic acid, methyl acrylate and methyl methacrylate.

The capsule-in-capsule oral delivery system provide for a system wherein the wherein the outside and firstly exposed second capsule releases the first capsule in the ileum and once released the first capsule is solubilized in the proximal colon at a pH of about 6.2 to about 6.5 with the release of the desirable probiotics or therapeutic agents. If the content is desirable probiotics then such probiotics comprise at least one to 30 species of bacteria, more preferably from about 10 to 25 different species or strains of such species that are normally present in a pre-determined location within the gastrointestinal tract of a subject and preferable the pre-determined location is the ileum or colon. The desirable probiotics may comprise a mixture of bacterial genera that is reflective of the mixture of strains derived from the ileum of a normal human, and the number of said organisms released is more than $10^5$ and less than $10^{12}$ and preferably the release is in the distal segments of the gastrointestinal tract including the ileum and colon of a subject and to ameliorate the imbalance of *Clostridium difficile* in a subject suffering from such an imbalance. Such probiotics comprise a live bacterial suspension selected from the genus *Lactobacillus* and *Bifidobacterium* and may further the organism *Faecalibacterium prausnitzii*.

A very effective combination of coating for the capsule-in-capsule oral delivery system comprises a the first capsule is coated (first enteric coating) with about 10 mg/cm$^2$ of EUDRAGIT® EPO and the second capsule is coated (second enteric coating) with about 5 mg/cm$^2$ of EUDRAGIT® L100/S100, 75/25 mix wherein the capsules are fabricated from hydroxypropylmethyl cellulose.

Still another aspect of the present invention provides for a method of treating the onset of a gastrointestinal disorder, the method comprising administering to a subject in need of such treatment in a pharmaceutically effective amount of an oral formulation comprising:

a first capsule containing desirable probiotics having beneficial effects on a gastrointestinal disorder, wherein the first capsule is fabricated of a biodegradable material and wherein the first capsule is coated with a first enteric coating that solubilizes in a pH of about 6.2 to about 6.5; and a second capsule being of a size that can include within its dimensions the coated first capsule, wherein the second capsule is fabricated of a biodegradable material and wherein the second capsule is coated with a second enteric coating that solubilizes in a pH of about 7 to 8, wherein the second capsule releases the first capsule in the ileum and once released the first capsule is solubilized in the proximal colon at a pH of about 6.2 to about 6.5 with the release of the desirable probiotics.

The gastrointestinal disorder includes a *Clostridium difficile* disorder that is associated with one or more of a *Clostridium difficile* infection, an imbalance of *Clostridium difficile* in the ileum or colon of said subject, diarrhea, inflammation, colitis fever, and wherein the oral formulation is in an amount sufficient to alleviate the gastrointestinal disorder in the subject and comprises a live bacterial suspension selected from the genus *Lactobacillus* and *Bifidobacterium*.

In a still further aspect, the present invention provides for the use of an oral formulation for preparing a medicament for the treatment of gastrointestinal disorder wherein the oral formulation comprises:

a first capsule containing a desirable bacteria effective against the gastrointestinal disorder, wherein the first capsule is fabricated of a biodegradable material and wherein the first capsule is coated with an enteric coating that solubilizes in a pH of about 6.2 to about 6.5; and a second capsule being of a size that can include within its dimensions the coated first capsule, wherein the second capsule is fabricated of a biodegradable material and wherein the second capsule is coated with an enteric coating that solubilizes in a pH of about 7 to 8, wherein the second capsule releases the first capsule in the ileum and once released the first capsule is solubilized in the proximal colon at a pH of about 6.2 to about 6.5 with the release of the desirable bacteria.

Another aspect of the present invention provides for an oral delivery system to deliver an oral formulation targeted directly to the ileum and/or colon of a subject with essentially no loss of the oral formulation before reaching at least the ileum, the system comprising:

a core comprising the oral formulation, wherein the oral formulation comprises probiotics or a therapeutic agent;

a first enteric coating encapsulating the core, wherein the first coating dissolves in a dissolution pH of about 6.2 to about 6.5;

a second enteric coating encapsulating the first coating, wherein the second coating dissolves in a dissolution pH of about 7 to 8.

Preferably, this oral delivery system further comprising a first biodegradable film layer positioned between the core and first coating and also a second biodegradable film layer positioned between the first coating and the second coating, wherein the biodegradable film is hydroxypropylmethyl cellulose.

Other features and advantages of the invention will be apparent from the following detailed description, drawings and claims.

DETAILED DESCRIPTION OF THE INVENTION

Figure 1:
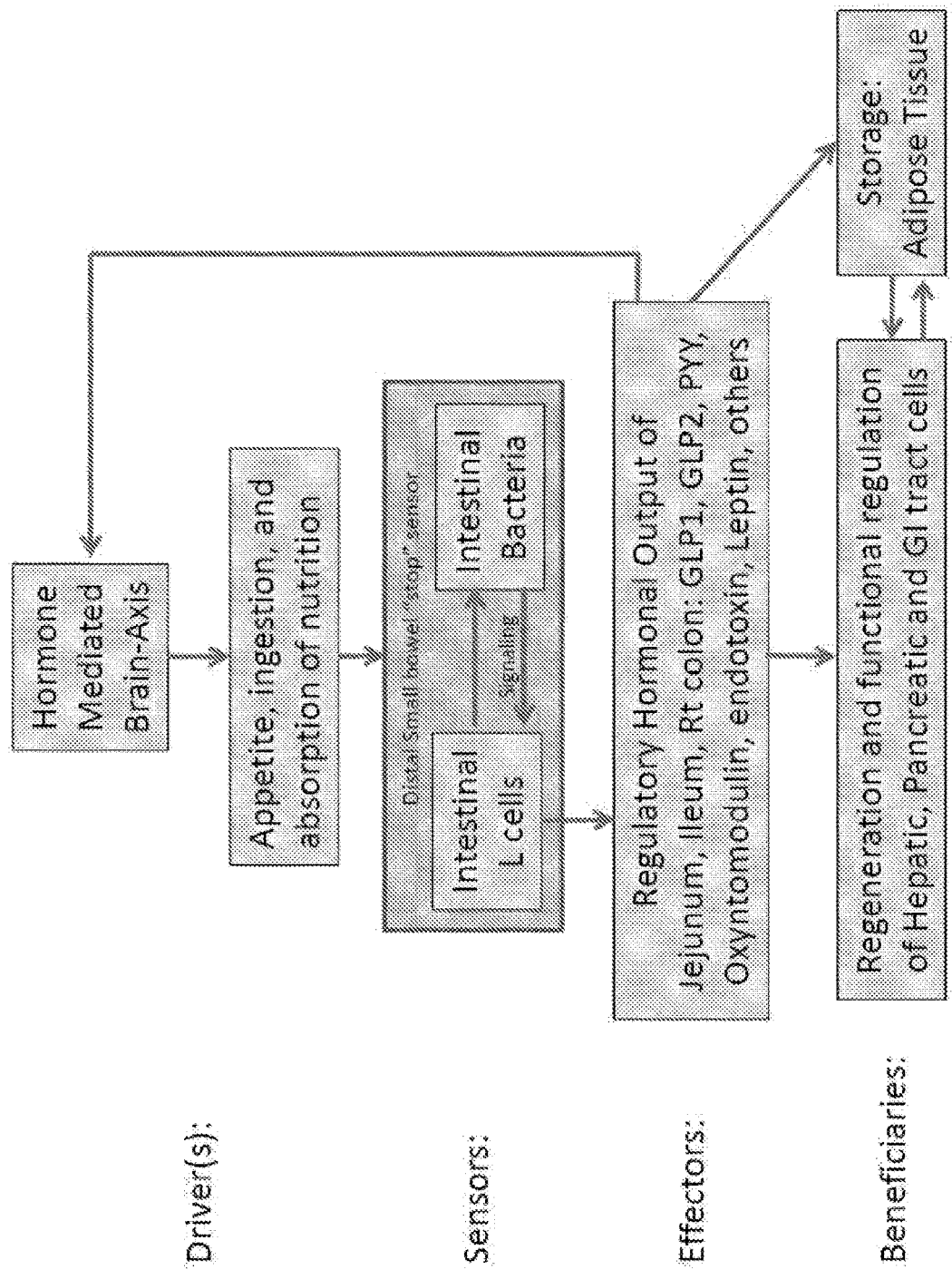
FIG. 1 shows the Distal Intestine Regulatory component of MetaSensor and associated host Metabolomics-Interactions between L-cells and Probiotic bacteria.

The practice of the present invention may employ various conventional techniques of molecular biology (including recombinant techniques), microbiology, cell biology, biochemistry, nucleic acid chemistry, and immunology, which are within the skill of the art. Unless indicated otherwise, the following terms have the following meanings when used herein and in the appended claims. Those terms that are not defined below or elsewhere in the specification shall have their art-recognized meaning.

A "stable" formulation or composition is one in which the biologically active material therein essentially retains its physical stability, chemical stability, and/or biological activity upon storage. Stability can be measured at a selected temperature and humidity conditions for a selected time period. Trend analysis can be used to estimate an expected shelf life before a material has actually been in storage for that time period. For live bacteria, for example, stability may be defined as the time it takes to lose 1 log of CFU/g dry formulation under predefined conditions of temperature, humidity and time period.

"Viability" with regard to bacteria, refers to the ability to form a colony (CFU or Colony Forming Unit) on a nutrient media appropriate for the growth of the bacteria. Viability, with regard to viruses, refers to the ability to infect and reproduce in a suitable host cell, resulting in the formation of a plaque on a lawn of host cells.

By "reduce" or other forms of the word, such as "reducing" or "reduction," may in certain instances refer to lowering of an event or characteristic (e.g., microorganism growth or survival). It is understood that this is typically in relation to some standard or expected value, in other words it is relative, but that it is not always necessary for the standard or relative value to be referred to. For example, "reduces the population of bacteria" in certain instances may refer to lowering the amount of bacteria relative to a standard or a control.

By "treat" or other forms of the word, such as "treated" or "treatment," may, in certain instances mean to administer a composition or to perform a method in order to reduce, prevent, inhibit, break-down, or eliminate a particular characteristic or event (e.g., microorganism growth or survival).

The term "viable cell" may in certain instances mean a microorganism that is alive and capable of regeneration and/or propagation, while in a vegetative, frozen, preserved, or reconstituted state.

The term "viable cell yield" or "viable cell concentration" may, in certain instances refer to the number of viable cells in a liquid culture, concentrated, or preserved state per a unit of measure, such as liter, milliliter, kilogram, gram or milligram.

The term "cell preservation" in certain instances may refer to a process that takes a vegetative cell and preserves it in a metabolically inert state that retains viability over time. As used herein, the term "product" in certain instances may refer to a microbial composition that can be blended with other components and contains specified concentration of viable cells that can be sold and used.

The terms "microorganism" or "microbe" in certain instances may refer to an organism of microscopic size, to a single-celled organism, and/or to any virus particle. The definition of microorganism used herein includes Bacteria, Archaea, single-celled Eukaryotes (protozoa, fungi, and ciliates), and viral agents.

The term "microbial" in certain instances may refer to processes or compositions of microorganisms, thus a "microbial-based product" is a composition that includes microorganisms, cellular components of the microorganisms, and/or metabolites produced by the microorganisms. Microorganisms can exist in various states and occur in vegetative, dormant, or spore states. Microorganisms can also occur as either motile or non-motile, and may be found as planktonic cells (unattached), substrate affixed cells, cells within colonies, or cells within a biofilm.

The term "prebiotic" in certain instances may refer to food ingredients or bacterial producing ingredients that are not readily digestible by endogenous host enzymes and confer beneficial effects on an organism that consumes them by selectively stimulating the growth and/or activity of a limited range of beneficial microorganisms that are associated with the intestinal tract. Also the term includes one or more live microorganisms that confer beneficial effects on a host organism. Benefits derived from the establishment of probiotic microorganisms within the digestive tract include reduction of pathogen load, improved microbial fermentation patterns, improved nutrient absorption, improved immune function, improved intestinal hormonal signaling and metabolic regulation, aided digestion and relief of symptoms of irritable bowel disease and colitis.

The term "Symbiotic" in certain instances may refer to a composition that contains both probiotics and prebiotics. Symbiotic compositions are those in which the prebiotic compound selectively favors the probiotic microorganism.

The term "gastrointestinal tract" in certain instances may refer to the complete system of organs and regions that are involved with ingestion, digestion, and excretion of food and liquids. This system generally consists of, but not limited to, the mouth, esophagus, stomach and or rumen, intestines (both small and large), cecum (plural ceca), fermentation sacs, and the anus.

The term "pathogen" in certain instances may refer to any microorganism that produces a harmful effect and/or disease state in a human or animal host.

The pharmaceutical formulations provided herein may further include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0. Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinylpyrrolidone, etc. The pharmaceutical preparations can be mixed with auxiliary agents, e.g., lubricants, stabilizers, wetting agents, emulsifiers, salts for influencing osmotic pressure, buffers, coloring, and/or aromatic substances and the like which do not deleteriously react with the active compounds. They can also be combined where desired with other active substances, e.g., ileal brake hormone regulatory substances to improve metabolism and ameliorate metabolic syndromes.

Compounds provided herein may be formulated in a pharmaceutical composition, which may include pharmaceutically acceptable carriers, thickeners, diluents, buffers, surface active agents, neutral or cationic lipids, lipid complexes, liposomes, penetration enhancers, carrier compounds and other pharmaceutically acceptable carriers or excipients and the like in addition to the compound.

Pharmaceutical compositions may also include one or more active ingredients such as, anti-inflammatory agents, anesthetics, and the like. Formulations for oral or intravaginal administration may include buffers, liposomes, diluents and other suitable additives. The compositions provided herein may additionally contain other adjunct components conventionally found in pharmaceutical compositions, at their art-established usage levels. Thus, for example, the compositions may contain additional compatible pharmaceutically-active materials such as, e.g., statins, linaclotide, ileal brake hormone releasing substances, anti-inflammatory agents, or may contain additional materials useful in physically formulating various dosage forms of the composition of present invention, such as dyes, flavoring agents, antioxidants, opacifiers, thickening agents and stabilizers. Depending on the particular active ingredients, the formulations may be administered in the same pill or tablet or as a distinct pill or tablet as part of a co-administration protocol. However, such materials, when added, should not unduly interfere with the biological activities of the components of the compositions provided herein.

Regardless of the method by which compounds are introduced into a patient, colloidal dispersion systems may be used as delivery vehicles to enhance the in vivo stability of the compounds and/or to target the compounds to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:compound complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 6, 698-708 (1995)). Likewise, microparticulate or nanoparticulate polymeric bead dosage forms may be used in composition provided herein. Compounds provided herein may be used in combination with one or more additional active agent and encapsulated in a particulate dosage form. In this manner, certain compounds provided here, alone or in combination with other active agents, are released at that site over time to provide a sustained therapeutic benefit. Release of the active agent from the particulate dosage forms of the present invention can occur as a result of both diffusion and particulate matrix erosion. Biodegradation rate directly impacts active agent release kinetics.

In preferred embodiments, the pharmaceutical composition of the invention is administered orally. Dosing can be dependent on a number of factors, including severity and responsiveness of the disease state to be treated, and with the course of treatment lasting from several days to several months, or until a cure is effected or a diminution of the disease state is achieved. Toxicity and therapeutic efficacy of compounds provided herein can be determined by standard pharmaceutical procedures in cell cultures or experimental animals. For example, for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from in vitro and in vivo assays and animal studies can be used in formulating a range of dosage for use in humans. The dosage of such compounds lies preferably within a range of exposure concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a local exposure ranges that includes the cell derived $IC_{50}$ (i.e., the concentration of the test compound which achieves a half-maximal inhibition of symptoms) as determined in cell culture. Such information can be used to more accurately determine useful doses in humans. Levels in plasma are expected to be unmeasurably low. Dosing schedules can be calculated from measurements of drug accumulation in the intestinal tract and feces of the patient. Not relevant, organisms are not absorbed.

Suitable dosage amounts for probiotic organisms may, for example, vary from about $10^5$ to $10^{12}$ organisms, typically about $10^6$ based on the numbers of organisms found in the ileum of said patient. Similarly, delivery of compounds provided herein will be specific to particular cells, conditions, and locations, such as ileum. In general, dosage is from tablets, capsules, granules and microgranules, powders, liquids and alike, and which may be given once or more daily, weekly, monthly or yearly, or even less frequently. In the treatment or prevention of certain conditions, an appropriate dosage level will generally be as above per day which can be administered in single or multiple doses. Live microorganisms or therapeutic compounds according to the invention (e.g. live organisms) may be formulated into pharmaceutical compositions for administration according to known methodologies, including for example using immediate-release, as well as pulsatile-release, and delayed-release technologies. Pharmaceutical compositions may, for example, comprise one or more constructs, in combination with a pharmaceutically acceptable carrier, excipient or diluent. Such carriers will be nontoxic to recipients at the dosages employed. A suitable dosage may be from about as above, per species at least $10^5$ to $10^{12}$ oral and various ranges within these amounts being still more typical for administration. It will be evident to those skilled in the art that the number and frequency of administration will be dependent upon the response of the host. "Pharmaceutically acceptable carriers" for therapeutic use are well known in the pharmaceutical art, and are described, for example, in *Remington's Pharmaceutical Sciences*, Mack Publishing Co. (A. R. Gennaro edit. 1985). For example, saline and phosphate-buffered saline at physiological pH may be used. Stabilizers, dyes and even flavoring agents may be provided in the pharmaceutical composition.

"Pharmaceutically acceptable salt" refers to salts of the compounds of the present invention derived from the combination of such compounds and an organic or inorganic acid (acid addition salts) or an organic or inorganic base (base addition salts). The compounds of the present invention may be used in either the free base or salt forms, with both forms being considered as being within the scope of the present invention.

However, pharmaceutical compositions provided herein may be in any form which allows for the composition to be administered to a patient by the oral route and less commonly by intravaginal or rectal routes. The pharmaceutical composition is formulated so as to allow the active ingredients contained therein to be bioavailable at the site targeted upon administration of the composition to a patient. Compositions that will be administered to a patient take the form of one or more dosage units, where for example, a tablet may be a single dosage unit, and a container of one or more compounds of the invention in oral form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed, applying common membranes used for microencapsulation and suitable for the microencapsulation of live probiotic organisms include biodegradable synthetic "polymers" such as polylactide, polyglycolic acid, and polyanhydride. Established "polymers" for live encapsulation and enzyme encapsulation include alginate-polylysine-alginate (APA), alginate-polymethylene-co-guanidine-alginate (A-PMCG-A), hydroymethylacrylate-methyl methacrylate (HEMA-MMA), Multi-layered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD$_5$/PDMS), poly N,N-dimethyl acrylamide (PD-MAAm), Siliceous encapsulates and cellulose sulphate/sodium alginate/polymethylene-co-guanidine (CS/A/PMCG). Other materials that are useful include, without limitation, cellulose acetate phthalate, calcium alginate and k-carrageenan-Locust bean gum gel beads, gellan-xanthan beads, poly(lactide-co-glycolides), carrageenan, starch polyanhydrides, starch polymethacrylates, polyamino acids, enteric coating polymers.

A liquid pharmaceutical composition as used herein, whether in the form of a solution, suspension or other like form, may include one or more of the following adjuvants: diluents such as water, preferably fixed oils such as synthetic mono or diglycerides which may serve as the solvent or suspending medium, polyethylene glycols, glycerin, propylene glycol or other solvents; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Compounds described herein can be used in diagnostics, therapeutics, prophylaxis, and as research reagents and in kits. Provision of means for detecting compounds of the invention can routinely be accomplished. Such provision may include enzyme conjugation, radiolabelling or any other suitable detection systems. Kits for detecting the presence or absence of compounds of the invention may also be prepared.

The compounds of the invention may also be used for research purposes. Thus, the specific activities or modalities exhibited by the compounds may be used for assays, purifications, cellular product preparations and in other methodologies which may be appreciated by persons of ordinary skill in the art.

Using the Smart Pill to study pH of the intestinal tract and thereby define the pH of the target sites of ileum and colon for release of specific probiotic organisms. Recently, the SmartPill, a wireless pH/pressure recording capsule, has been utilized to measure the whole gut transit time. Wireless capsule motility, using the SmartPill GI monitoring system, samples and transmits intraluminal pH, pressure, and temperature data from a capsule at regular intervals as it traverses through the gastrointestinal tract; from these, gastric emptying and whole gastrointestinal tract transit can be assessed. In addition, there are a few studies on the small bowel pH. The aim of this study was to investigate the relationship between small bowel disease and the small bowel pH, using the SmartPill to non-invasively record sequential images and the pH. Volunteers swallowed the SmartPill with 240 mL of water. The SmartPill transmitted the acquired images and the pH to the recorder unit located outside the body for about ten hours while the subject was fasting. SmartPill capsule shows promise as a useful diagnostic test to evaluate patients for GI transit disorders and to study the effects of diseases of the gastrointestinal tract on pH and GI transit (8). The intragastric pH was low and after gastric emptying the pH in the whole small intestine rose from 6.0 to as high as 8.1 in the ileum, then after passing the ileocecal valve, the pH of the right colon was once again 5.5 to 6.5. The pH value increased from the duodenum to the terminal ileum ($p<0.0001$) in all patients, but diabetic subjects and obese patients did not rise as high as normal subjects. These findings were unexpected, and indicate that the release target is different for formulated probiotic organisms in the ileum and right colon of diabetics and obese patients, compared to normal subjects. Clearly, effective practice of site specific delivery in the human intestinal tract requires adjustment for the differing conditions of the local ileum micro-environment, surprisingly a feature of disease associated changes in the microbiome as taught by experiments using SmartPill. Thus the concept of targeted probiotic replacements and making changes in signaling processes to treat disease is advanced to practice. Probiotic formulations and dosages and compositions must be completely changed to deal with these new discoveries.

Methods

Metabolic Syndrome and Obesity

There were two organisms that were found in intestinal flora in minor numbers, but which represented major regulatory balance organisms in the development of obesity and associated metabolic abnormalities, *Methanobrevibacter smithii* which promotes adiposity and *Bacteroides theataiotaomicron*, which down regulates metabolic syndrome associated inflammation and thereby removes the associated risk to the cardiovascular integrity of the host (1). Another organism found by others to be important is *Faecalobacterium prausnitzii*, the absence of which appears to correlate with worsening of obesity and Type 2 diabetes (2). In the practice of the instant invention, this organism is a target for replacement via targeted delivery to the ileum as in the present invention.

Resident host microflora condition and prime the immune system in the preferred practice of the invention are disclosed herein. However, systemic and mucosal immune responses to bacteria may be divergent. Several workers have examined the relationships between the immune system and the microbiome components in the gastrointestinal tract. For example, our work with patients having RYGB surgery showed elevated endotoxin and high levels of inflammation prior to surgery, followed after surgery by remediation and a lowering of inflammatory processes.(3). It is important to understand that current viewpoints show the ileum and the ileal brake hormone pathways to be the beneficial site of action of RYGB surgery, which is an effective treatment for obesity and in fact the only known means of curing metabolic syndrome associated type 2 diabetes. It is shown herein that the actions are mediated at the level of the ileum and the ileal brake, and the novel discovery was a lowering of chronic inflammation, presumed a cause of revised microbiome and revised signaling at the level of the intestinal L-cells. Additional novel discovery was the level of close interaction between the intestinal L-cells, the intestinal bacteria, and the systemic host inflammation, which is responsible for the various diseases that are considered part of overall metabolic syndrome in humans(3). O'Mahony and colleagues examined the inflammatory signaling processes involved in this pathway. Their aim was to compare, in vitro, cytokine production by human mononuclear and dendritic cells (DCs) from mesenteric lymph nodes (MLNs) and peripheral blood mononuclear cells (PBMCs) to defined microbial stimuli. Mononuclear cells and DCs isolated from the MLN (n=10) and peripheral blood (n=12) of patients with active colitis were incubated in vitro with the probiotic bacteria *Lactobacillus salivarius* UCC118 or *Bifidobacterium infantis* 35624 or the pathogenic organism *Salmonella typhimurium* UK1. Interleukin (IL)-12, tumor necrosis factor (TNF)-alpha, transforming growth factor (TGF)-beta, and 1-10 cytokine levels were quantified by ELISA. PBMCs and PBMC-derived DCs secreted TNF-alpha in response to the *Lactobacillus*, Bifidobacteria, and *Salmonella* strains, whereas MLN cells and MLN-derived DCs secreted TNF-alpha only in response to *Salmonella* challenge. Cells from the systemic compartment secreted IL-12 after co-incubation with *Salmonella* or Lactobacilli, whereas MLN-derived cells produced IL-12 only in response to *Salmonella*. PBMCs secreted IL-10 in response to the *Bifidobacterium* strain but not in response to the *Lactobacillus* or *Salmonella* strain. However, MLN cells secreted IL-10 in response to Bifidobacteria and Lactobacilli but not in response to *Salmonella*. In conclusion, commensal bacteria induced regulatory cytokine production by MLN cells, whereas pathogenic bacteria induce T cell helper 1-polarizing cytokines. Commensal-pathogen divergence in cytokine responses is more marked in cells isolated from the mucosal immune system compared with PBMCs(4). This work indicates that the endogenous cellular signaling pathways at work in the distal gastrointestinal tract can discriminate their responses as the flora in the microbiome change between commensals and pathogens.

Immunoregulatory Pathways

Leukocyte recruitment is a central immune process. Multiple factors have been described to promote leukocyte infiltration into inflamed tissues, but only recently has evidence for endogenous negative modulators of this inflammatory process emerged. The discovery of several locally produced modulators has emerged into a new field of endogenous inhibitors of leukocyte extravasation. Recent findings from several inflammatory disease models show that tissues can self-regulate the recruitment of inflammatory cells, suggesting that local tissues may have a greater 'regulatory say' over the immune response than previously appreciated(5). Organisms targeted for replacement in obese or diabetic patients could be delivered as components of an oral site specific delivery formulation designed to assist in the management of metabolic syndrome and prevent or control associated inflammatory manifestations such as obesity and type 2 diabetes. This novel therapeutic approach, based on changing local signaling at the level of intestinal L-cells and dendritic cells, is proposed based on the observation that locally produced modulators of leukocyte recruitment may represent local homeostatic mechanisms that tissues and organs may have evolved for protection against the destructive potential of the immune system (5). The involvement of the local microbiome flora as a protective factor, beneficial to the host, is a novel aspect in the practice of the invention, since this would explain why use of certain antibiotics used for treatment of infection may cause more problems from dysbiosis than are solved by eradicating pathogens.

Larsen and colleagues have studied the link between metabolic diseases and bacterial populations in the gut. The aim of their studies was to assess the differences between the compositions of the intestinal microbiota in humans with type 2 diabetes and compare to controls who were non-diabetic persons. The study population included 36 male adults with a broad range of age and body-mass indices (BMIs), among which 18 subjects were diagnosed with diabetes type 2. The fecal bacterial composition was investigated by real-time quantitative PCR (qPCR) and in a subgroup of subjects (N=20) by tag-encoded amplicon pyrosequencing of the V4 region of the 16S rRNA gene. The proportions of phylum Firmicutes and class Clostridia were significantly reduced in the diabetic group compared to the control group (P=0.03). Furthermore, the ratios of Bacteroidetes to Firmicutes as well as the ratios of *Bacteroides-Prevotella* group to *C. coccoides-E. rectale* group correlated positively and significantly with plasma glucose concentration (P=0.04) but not with BMIs. Similarly, class Betaproteobacteria was highly enriched in diabetic compared to non-diabetic persons (P=0.02) and positively correlated with plasma glucose (P=0.04). The results of this study indicated that type 2 diabetes in humans is associated with compositional changes in intestinal microbiota. The level of glucose tolerance should be considered when linking microbiota with metabolic diseases such as obesity and developing strategies to control metabolic diseases by modifying the gut microbiota(6).

Recent studies have focused additional attention on intestinal microbiota as environmental factors that increase energy yield from diet, regulate peripheral metabolism and thereby increase body weight. Obesity is associated with substantial changes in composition and metabolic function of gut microbiota, but the pathophysiological processes driving this bidirectional relationship have not been fully elucidated. Clearly there are important relationships between the composition of gut microbiota, energy extracted from diet, synthesis of gut hormones involved in energy homeostasis, production of butyrate and the regulation of fat storage (7). The most important discoveries of this work are from our own studies examining the release of hormones from the distal intestines in response to stimulating factors such as foods and probiotic organisms (3).

Figure 2:
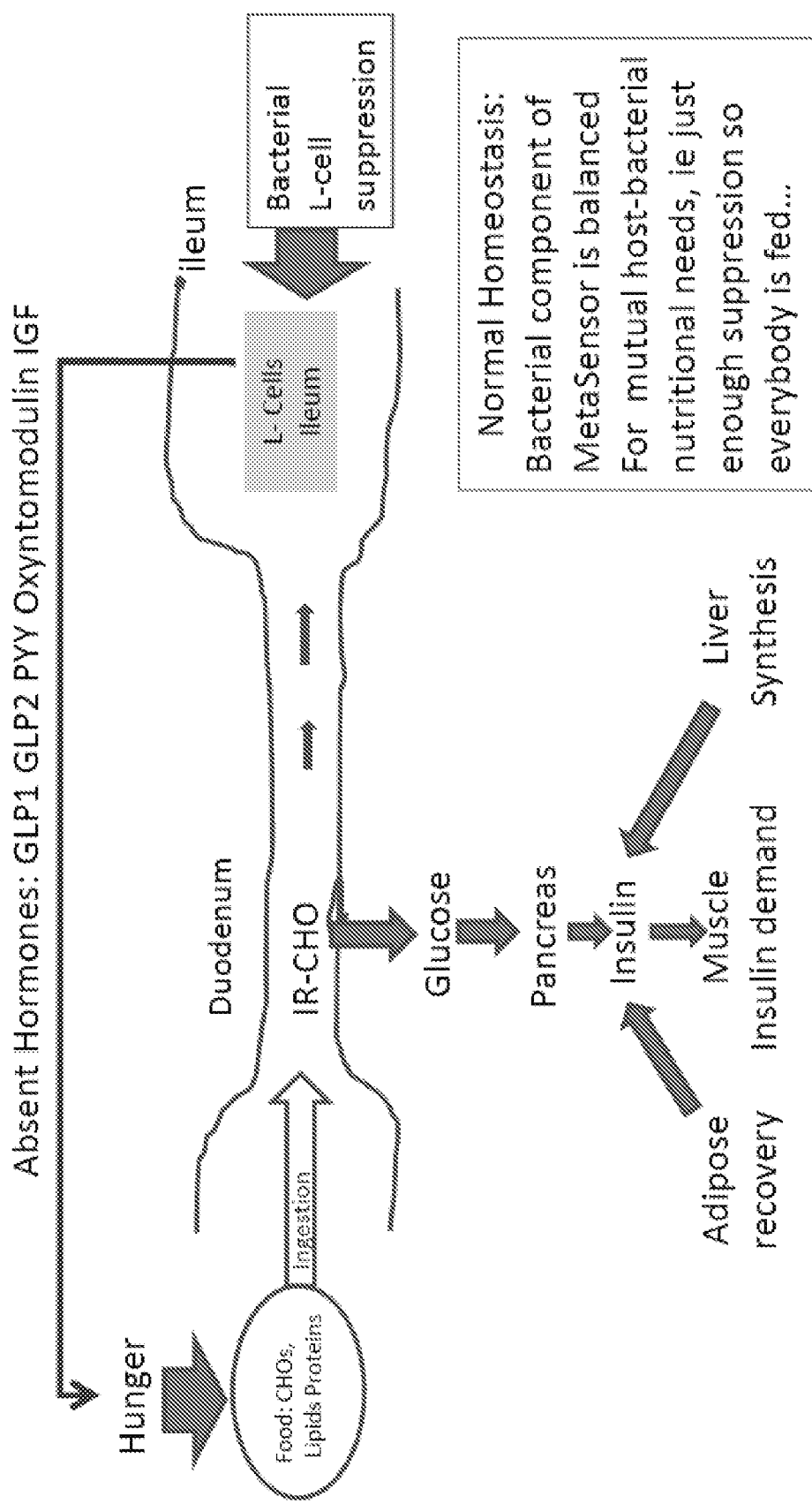
FIG. 2 shows normal operations of the MetaSensor via stop signals GLP-1, PYY and other L-cell derived regulatory hormones.
Figure 3:
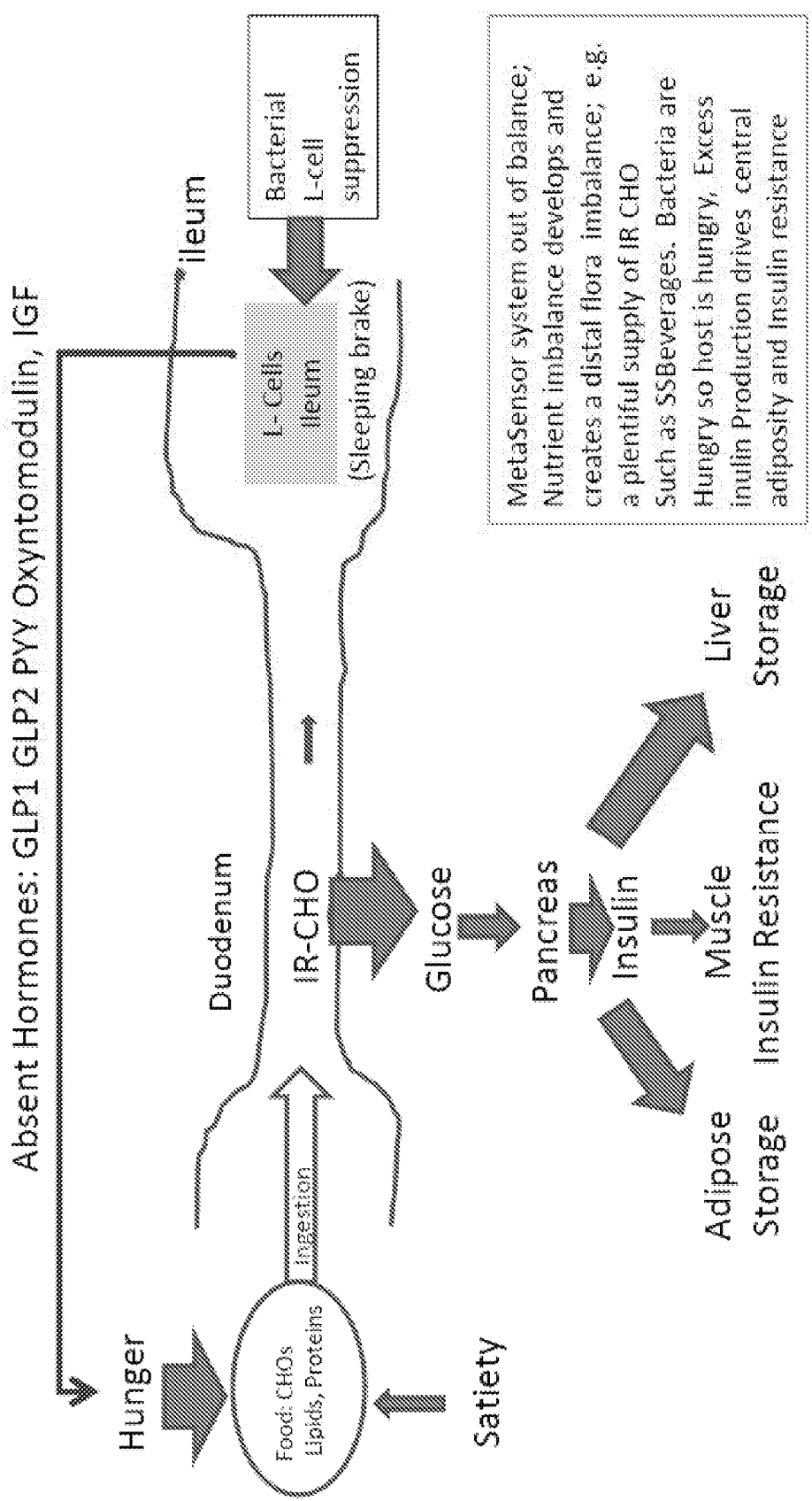
FIG. 3 shows the situation when a diabetogenic food, such as sugar sweetened beverage alters the microbiome and thus the hormonal operation of the MetaSensor.
Figure 4:
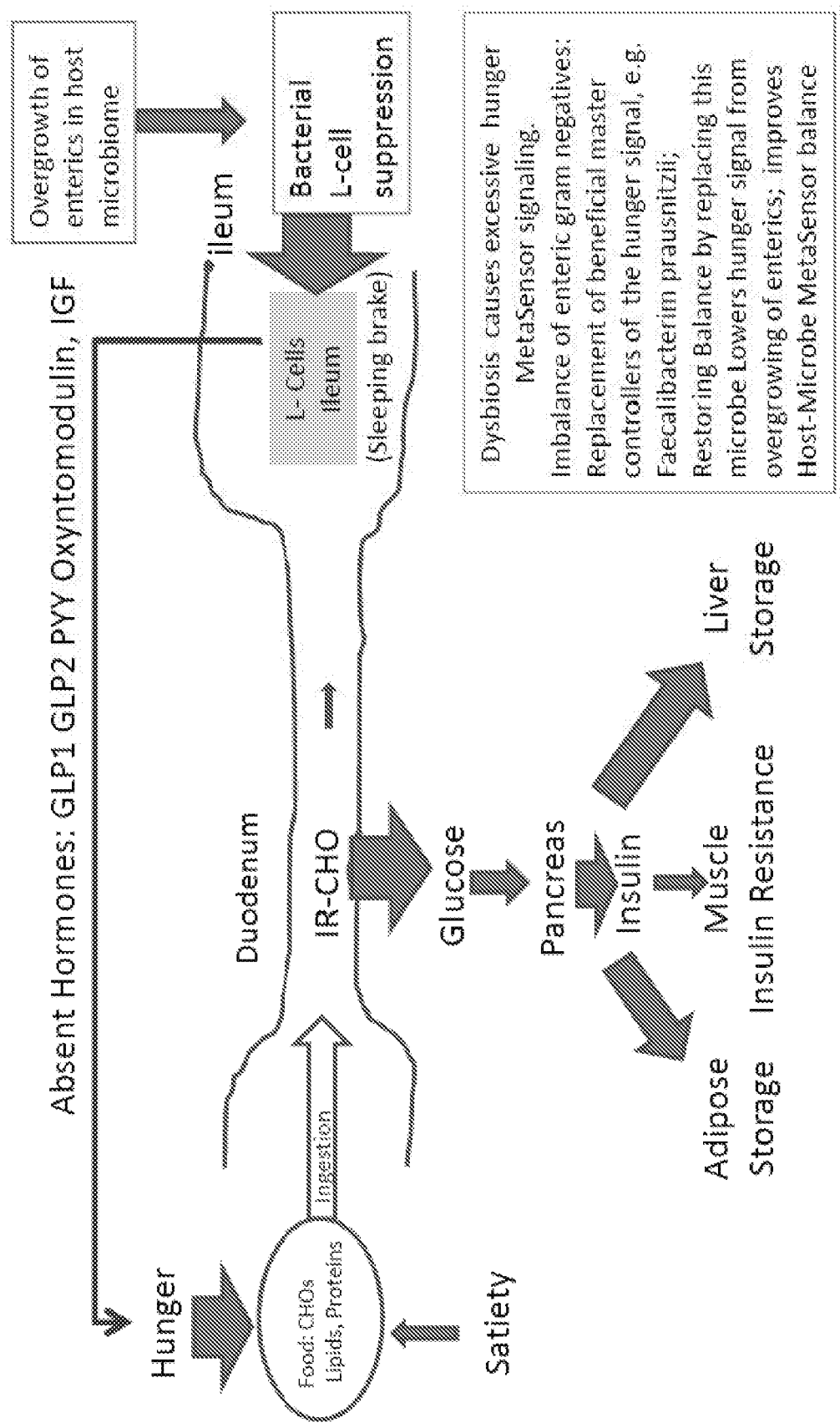
FIG. 4 shows the situation when there is a Microbiome dysbiosis that produces abnormal regulatory control of the MetaSensor via its action on the L-cells.
Figure 5:
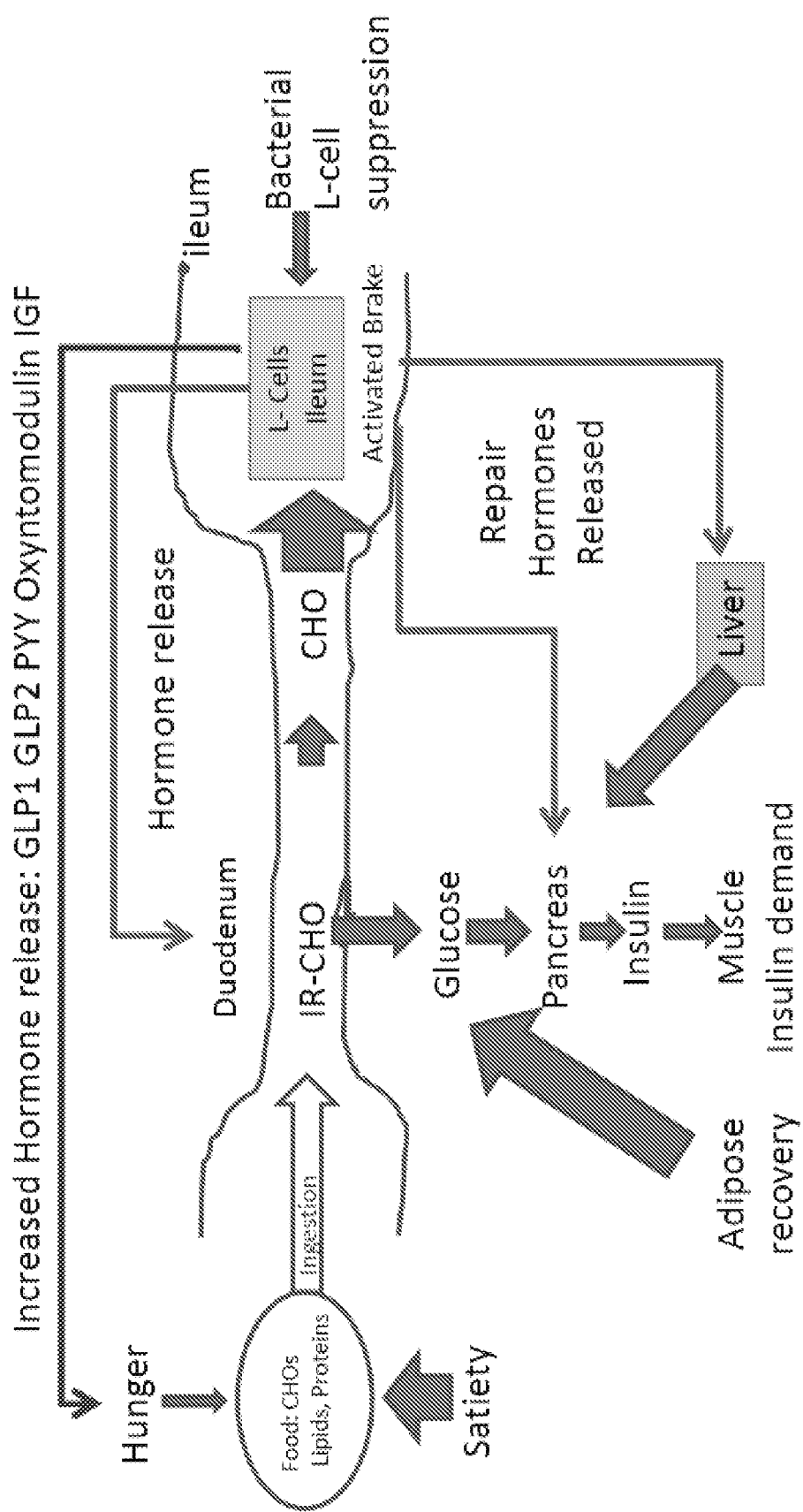
FIG. 5 shows the impact of Roux-en-Y gastric bypass (RYGB) surgery on the MetaSensor.
Figure 6:
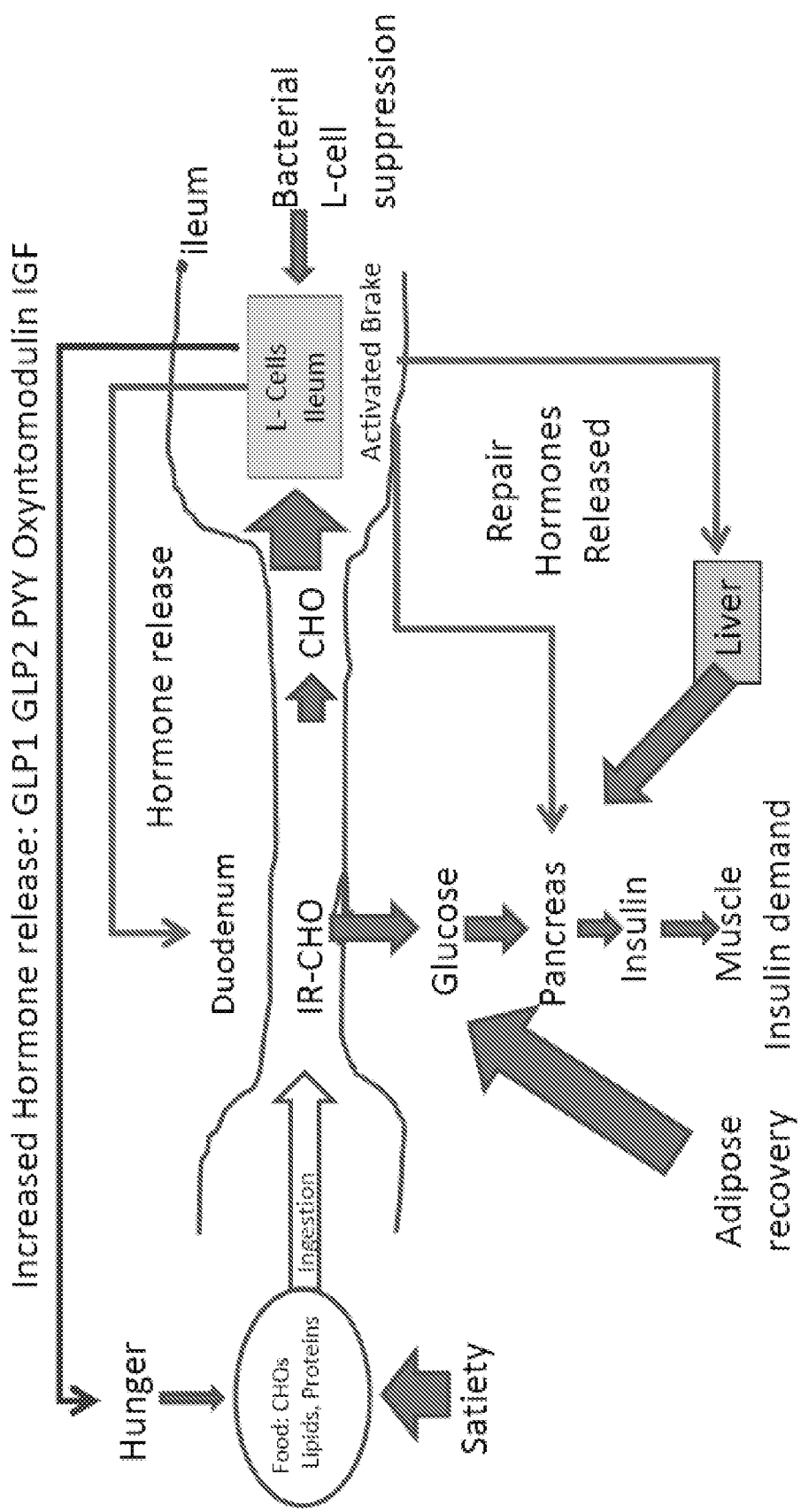
FIG. 6 shows the impact of an oral mimetic of RYGB, an ileal brake hormone releasing substance called Brake, on the MetaSensor.
Figure 7:
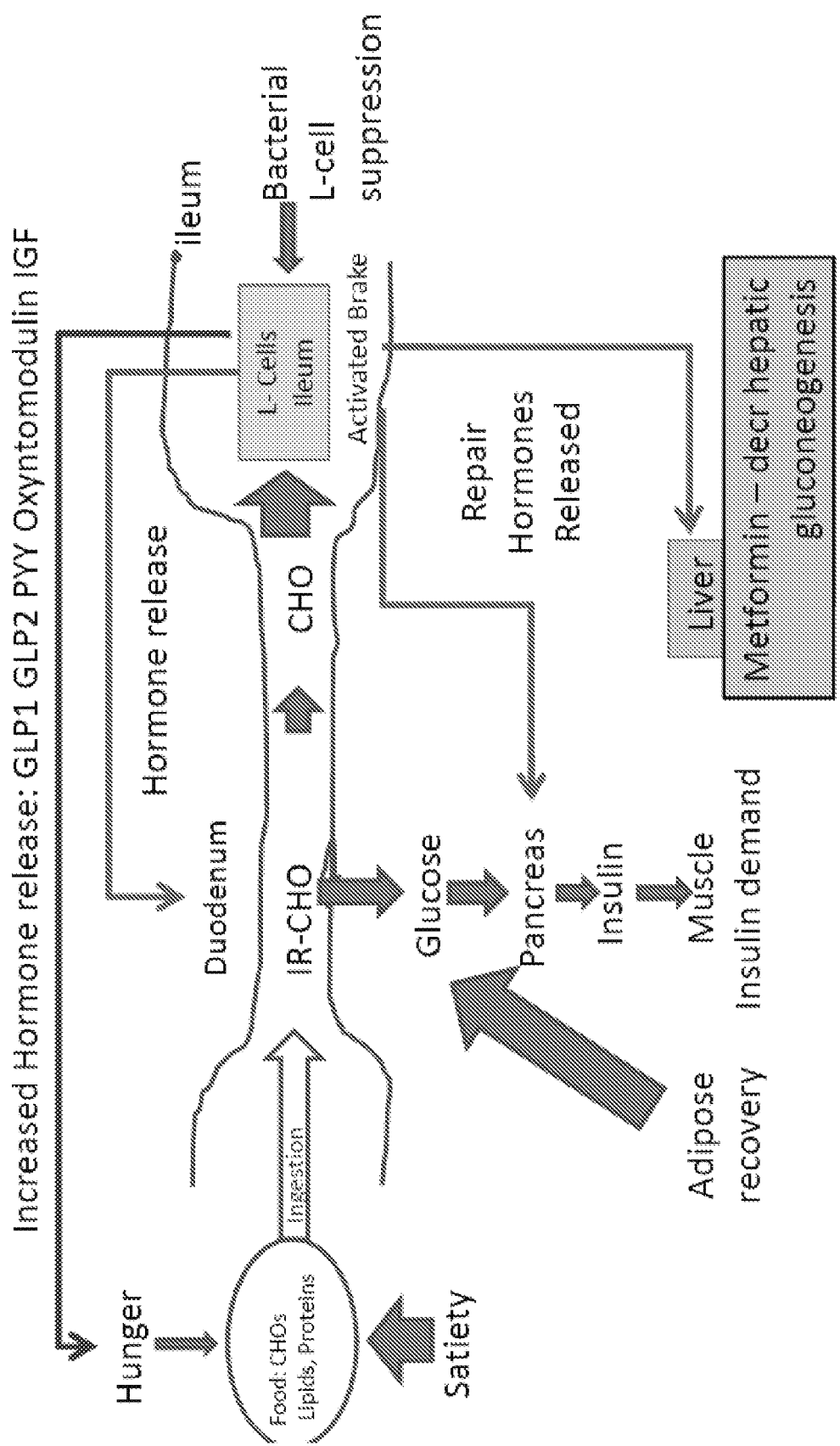
FIG. 7 considers the impact of a common diabetes drug, metformin, in combined with Brake, on the operations of the MetaSensory process, illustrating synergistic interactions between a drug and a mimetic of RYGB surgery.

Regulation of the Host Metabolome and the Invention of the Metabolomic MetaSensor The distal intestine's responsiveness to molecules presented to it via diet is important in regulating the upstream sensory drivers of ingestion such as hunger, taste, smell, and appetite. Together the interaction between ingestion, selective absorption and feedback regulatory control of appetite ensure that the organism is properly nourished and its energy needs are properly balanced by intake of food as fuel, and the current term used to describe the steps in these processes is Metabolomics. It is important to consider the "organism" in this case to be the combination of all cells, including bacteria, viruses, fungi and human cells, together a MetaOrganism, which in terms of cell numbers is more than 90% non-human cells. The biosensors effecting these complex processes are interactive between the non-human cells and the human cells, together a MetaSensor, and it is expected that most Metabolomic processes will be controlled by MetaSensory signaling, i.e. interactiveness between non-human and human cells. Likewise, it is theorized that host immunity and thus conditions like food allergy are controlled by these same distal intestinal MetaSensors. Considering the central role of the master regulatory MetaSensor in host metabolomics at homeostasis, it is clear that food intake is regulated by the combined sensor signals defining input (brain programmed appetite interacting with taste and smell), counterbalanced precisely by the distal intestinal sensor signals such as the ileal brake and associated hormonal regulatory "stop input" signals that are received when ingestion exceeds the ability of the organism to absorb upstream in the duodenum and jejunum. In normal operations, host demand for energy dominates, and ingestion of nutrients proceeds unimpeded by stop signals. When energy intake exceeds demand, there is both short term and long term storage of excess. Short term storage includes abdominal adipose and liver, and long term storage is peripheral adipose, both of which interact with the MetaSensory signaling processes to balance supply and demand for energy. There is good understanding of the balance created between ingestion and storage, driven largely by appetite and the combined sensory input from taste and smell. However, it is novel to identify the ileal brake and its associated regulatory MetaSensor component as a stop signal on the ingestion process, and our work in this area with the pathways operative in RYGB patients is illustrative (see WO2012-118712, hereby incorporated in its entirety), wherein we have shown that ileal delivery of food substances creates a stop signal because the MetaSensor detects malabsorption and uses the hormones released from the L-cells of the ileum (GLP-1, PYY and many others) to shut down ingestion and appetite via brain stimulatory feedback. In a breakthrough discovery, we are now advancing a plausible means of operating the ileal brake component of the intestinal MetaSensor, and its integral controllers. In an individual of normal weight and in nutritional balance the ileal brake component of the MetaSensor, (the controller of the stop signal) is comprised of host L-cells interacting with beneficial intestinal organisms. The intestinal bacteria are an essential component of MetaOrganism Metabolomics, and it is logical for them to have a major regulatory role in the operation of the stop signal from the ileum. Intestinal microbes lack the ability to signal the host brain directly, so they use host signaling pathways to make their needs known. The combined MetaSensor operates in the distal intestine, via interaction with the L-cells to regulate the stop signal to mutual benefit. Described simply, certain intestinal bacteria can suppress the stop on the appetite signal from the brain. They do this when they are hungry for a nutrient, food or even a specific molecule. When microbes deep in the intestinal tract are hungry, the host is hungry because the stop signal of the MetaSensor is inactivated. FIGS. 1 to 7 diagram the MetaSensor in detail, and show how it is comprised overall in FIG. 1, and in FIGS. 2-7 describe its operations in the ileum that control metabolomics and immunity. The MetaSensor in the ileum produces regulatory hormonal output from the combined actions of the enteral L-cells, and the intestinal bacteria. FIG. 2 shows normal operations of the MetaSensor via stop signals GLP-1, PYY and other L-cell derived regulatory hormones. Notably the system is in balance when diet is balanced and thus some excess reaches the distal intestine. However, when the patient ingests only IR-CHOs, the bacteria in the ileum are not achieving nutrition. They react by Suppression of L-cell output and hunger ensues. If on the other hand the patient is having a balance diet with portions reaching the bacteria, they have no reason to suppress the L-cell output and normal eating produces satiety. FIG. 3 shows the situation when a diabetogenic food, such as sugar sweetened beverage alters the microbiome and thus the hormonal operation of the MetaSensor. FIG. 4 shows the situation when there is a Microbiome dysbiosis that produces abnormal regulatory control of the MetaSensor via its action on the L-cells. With reference to our previous work with the ileal brake operations in health and disease, FIG. 5 shows the impact of RYGB surgery on the MetaSensor. Notably, RYGB surgery mechanically diverts ingested contents past the absorptive (but non-signaling) area, and bombards the signaling areas further downstream in late jejunum and ileum. The arrival of massive nutrients at the ileum in such a large quantity creates a "malabsorptive emergency" and initiates the satiety signal by shutting down the hormonal release from the L-cells to regenerate signaling to a certain extent with the same or less amount of food needed, therefore restoring maintenance and regeneration. And because it is not individualized, RYGB surgery will trigger more regeneration than signaling to the point that about 4 years down the line, the jejunum will evolve to restore absorption to a baseline levels. FIG. 6 shows the impact of an oral mimetic of RYGB, an ileal brake hormone releasing substance called Brake, on the MetaSensor. Brake acts the distally in the same way as RYGB surgery. There is the same activation of L-cells, the output of which produce regeneration and make hunger disappear into satiety. The strength of the ileal signal is not as potent as RYGB, but it can be more prolonged because of the delayed release formulation. Thus with Brake, the intensity of the stimulation will be more moderate and closer to physiological and therefore regeneration proceeds in Liver, pancreas, GI enterocytes in a much more natural and physiological way compared to surgery. Of no great surprise, weight loss is more rapid with RYGB, since RYGB surgery also physically decreases the size of stomach, limiting ingestion in a second, profound manner over the ileal brake pathway alone. Finally, FIG. 7 considers the impact of a common diabetes drug, metformin, in combined with Brake, on the operations of the MetaSensory process, illustrating synergistic interactions between a drug and a mimetic of RYGB surgery, this example is illustrative, and there are many more of these with other drugs used in the treatment of metabolic syndrome manifestations such as type 2 diabetes.

Briefly, the MetaSensor gives the stop signal to the brain via ileal brake hormones in response to its detection of perceived malabsorption. In total, the novel aspect of the invention, shown by this discussion and these figures, is the nature of this MetaSensors action on the host metabolome, that effect being the combined action of L-cell output from detection of food delivery and the actions of probiotic organisms on the L-cells to modify the signal in response to nutritional demands communicated by bacteria. It is remarkable how effectively the probiotic organisms control our appetite and selection of nutrients and foods to suit their own purposes. We are together with our probiotic symbionts, a balanced ecosystem, a true MetaOrganism. In homeostasis, all parties are successfully meeting their needs. Diseases, all loosely described as components of Metabolic Syndrome, are the results of imbalances, which may be bacterial in origin, or arise from the cells of the host. Regardless, both components of the MetaSensor must receive therapeutic attention if homeostasis is to be restored, and the current submission provides detailed means of re-balancing the MetaSensory output to restore homeostasis and remove diseases. All of the therapeutic advances described herein, and those to follow ongoing research, are transformational steps mediated by treatments changing the input-output properties of the MetaSensor described herein.

There are some other useful aspects to the MetaSensor in the distal ileum. Specifically, the MetaSensor provides a quick immune system mediated response when a foreign invader is detected in the GI tract lumen, and the rapid improvement of intestinal dysbiosis such as infection with *C. difficile* can be remediated by replacement of *C. difficile* with more beneficial organisms delivered by formulation to the ileum and colon via the oral formulations described herein. Furthermore, there are preferred enablements as distal ileum vaccines that are orally active. Specific examples are found in PCT/US13/31483, the entirety of which is herein incorporated by reference.

In parallel with the stimulation of the MetaSensor with a foreign organism, it is now clearly apparent that the MetaSensor is responsive to chemical substances that act on the probiotic bacteria, each of which has a specific molecule that excites a response which is then communicated to the human host via the L-cells, lymphoid tissue in Peyer's Patches, or in all possibility any enterocyte found in the lumen. When the host or the integrated intestinal organisms of the MetaOrganism encounters a deficiency of any nutritional component or essential substance, the signal for this deficiency comes to the brain from the MetaSensor in the intestine (if communicated by the host microbiome), and perhaps from the brain or tongue or nose if communicated by the host cells. The actions of the host to obtain that missing substance are perceived as "cravings" and after satisfied the MetaSensor stops the search. Thus, when the Microbiome organisms are hungry for something specific, we as the MetaOrganism are instructed to obtain that specific substance. This novel discovery immediately opens opportunities to regulate ingestion of potentially harmful substances like refined sugar, via therapeutic strategies focused on the MetaSensor itself, and explains the ability of ileum delivered glucose to regulate diabetes and other diseases called metabolic syndrome (see WO 2010-027498 and WO 2013-063527 A1, herein incorporated by reference). While these inventions focus on the needs of the host via regulatory MetaSensor action, it can readily be seen that regulating the Microbiome via targeted replacement will also impact the diseases of the host in a beneficial way. Replacement of organisms missing in association with metabolic diseases such as obesity, for example *Faecalibacterium prausnitzii*, is now possible with the ability disclosed herein to provide targeted oral delivery of live organisms to the site of the MetaSensor in the ileum.

The following Examples are offered by way of illustration and not by way of limitation.

Example 1

Example 1 is directed toward the making and testing of a formulation according to the invention for the treatment of a *Clostridium difficile* infection.

Biological Assays

Standard therapies for antibiotic-associated diarrhea (AAD) and *Clostridium difficile*-associated diarrhea (CDAD) have limited efficacy. Probiotic prophylaxis is a promising alternative for reduction of AAD and CDAD incidence. The preferred embodiment is microgranules administered to said patient with *Clostridium difficile* infection is about $10^5$ to $10^{12}$ cfu of one or more species of probiotic organisms, targeted to ileum and ascending colon. Preferred embodiments would be a mixture of probiotic organisms reflective of the balance and components of the microbiome of a normal human subject, preferably a patient free of antibiotic exposure in the past and not infected with *C. difficile* organisms. The clinical protocol for testing the efficacy of said formulation would administer said formulation of probiotic organisms to patients in the manner followed by others who have tested the effectiveness of probiotics or fecal transplantation for infections with *Clostridium difficile* in human patients. By way of example, a single-center, randomized, double-blind, placebo-controlled dose-ranging study, is conducted for one of these probiotics in adult inpatients allocated to one of three groups: two probiotic capsules per day, one probiotic capsule and one placebo capsule per day, or two placebo capsules per day. In the design using un-protected formulations of each probiotic organism, each probiotic capsule contained 50 billion c.f.u. of live organisms. Probiotic prophylaxis or treatment began within 36 h of initial antibiotic administration, continued for 5 days after the last antibiotic dose, and patients were followed for an additional 21 days. In this study, Pro-2 (15.5%) had a lower antibiotic associated diarrhea (AAD) incidence vs. Pro-1 (28.2%). Each probiotic group had a lower AAD incidence vs. placebo (44.1%). In patients who acquired AAD, Pro-2 (2.8 days) and Pro-1 (4.1 days) had shorter symptom duration vs. placebo (6.4 days). Similarly, Pro-2 (1.2%) had a lower *Clostridium difficile* associated diarrhea (CDAD) incidence vs. Pro-1 (9.4%). Each treatment group had a lower CDAD incidence vs. placebo (23.8%). Gastrointestinal symptoms were less common in the treatment groups vs. placebo and in Pro-2 vs. Pro-1. The proprietary probiotic blend used in this study was well tolerated and effective for reducing risk of AAD and, in particular, *Clostridium difficile* associated diarrheal infections in hospitalized patients on antibiotics. A dose-ranging effect was shown with 100 billion c.f.u., yielding superior outcomes and fewer gastrointestinal events compared to 50 billion c.f.u. (9). Clearly, a protective formulation would allow the targeted delivery of smaller numbers of these organisms, lowering the costs of production of the organisms for the product.

In follow up to the study design above, Johnson and colleagues conducted a literature search for randomized, placebo-controlled efficacy studies of probiotic use among adults receiving antibiotics, in which *Clostridium difficile* infection (CDI) was one of the outcomes measured. In addition, they conducted meta-analyses of probiotics that were included in more than one randomized trial. Eleven studies were identified; most were seriously underpowered to determine the efficacy of probiotics in the prevention of CDI. Two showed significantly lower rates of CDI among the probiotic recipients. A meta-analysis of three studies that used the probiotic combination *Lactobacillus acidophilus* CL1285 and *Lactobacillus casei* LBC80R and a combined analysis of those studies with four studies that used *Saccharomyces boulardii*, showed lower CDI rates in recipients of probiotics compared with recipients of placebo (risk ratio=0.39; 95% confidence interval 0.19-0.79). Thus, while potential flaws in study design were identified, a review of the available literature suggested that the primary prevention of CDI with specific probiotic agents may be achievable. Additional studies of sufficient size and with rigorous design are needed to confirm these findings.(10) By way of commentary, the studies reviewed did not target the probiotic organisms, and thus the present invention is far more effective than those unprotected formulations used thus far.

Materials and Methods:

Described below are formulations that are being made and tested for the target delivery for testing in biological assays, the formulation having an antibiotic (Vancomycin 250 mg) (millimeter range) for release at pH 1.0-6.0 in stomach, duodenum and ileum and symbiotic (prebiotic: L-Leucine; probiotic: species of: *Lactobacillus* and *Bifidobacterium*) for release at pH 5.5-6.2 in right colon every 6 hours.

Active Pharmaceutical Ingredient (API):
Antibiotic—Vancomcyin hydrochloride (micronized) supplied by local generic US/non-US suppliers, e.g., LGM Pharma, USA, etc.
Prebiotics—proteins (casein, hydrolyzed protein, etc.), peptides, amino acids (L-Leucine), carbohydrates glucose, lactose, starches, inulin, etc. and certain bacterial strains: provided by Denisco, CHR Hansen, Institu Risell-Lallemand and other high quality global suppliers of prebiotics.
Live probiotics Species of: *Lactobacillus* and *Bifidobacterium* provided by Denisco, CHR Hansen, Institu Risell-Lallemand and other high quality global suppliers.
Inactive Ingredients (Excipients):
Microcrystalline, starch, HPMC or equivalent "polymers", hard gelatin capsules, and other fillers, etc.— purchased from local US supplier such as FMC, Capsugel, Colorcon, etc.
Intermediate Formulation/Manufacturing Process (at Local CMO):
"Uncoated Antibiotic Granules/Pellets" (millimeter range):

| Ingredients | Amount (%) |
| --- | --- |
| Vancomcyin | 50% |
| Excipients (Microcrystalline cellulose - filler, polyvinyl-pyrrolidone - binder, pregelatinized starch - disintegrant, silicon dioxide - flow aid, magnesium stearate - lubricant) | 50% |
| Water as required | 0% |

Prepare a dry granulation with antibiotic and excipients in a low or high shear mixer and/or perform wet granulations with water and further pelletize using extruder/spheronizer and then drying to remove excess water using optimized conditions "pH 5.0 to 6.0 Enteric Coated (EC) Antibiotic Granules/Pellets" (millimeter range):

| Ingredients | Amount (%) |
| --- | --- |
| Uncoated Antibiotic Granules/Pellets | 95% |
| HPMC or equivalent "polymers" (Barrier and Seal coats) | 1% |
| "Polymers" (pH 5.0 to 6.0 sensitive coating) | 4% |
| Water/Solvents as required | 0% |

The Uncoated Antibiotic Granules/Pellets are coated (the barrier coat) with aqueous or solvent coating solution of HPMC or equivalent "polymers" to coat in a coating pan or fluid bed drier/coater using optimized conditions. The barrier coated micropellets or granules are further coated with aqueous or solvent coating solution of pH 5.0 to 6.0, sensitive coating "Polymers" in a coating pan or fluid bed drier/coater using optimized conditions. The above pH 5.0 to 6.0, sensitive coated micropellets or granules are seal coated with aqueous or solvent coating solution of HPMC or equivalent "polymers" in a coating pan or fluid bed drier/coater using optimized conditions.

"pH 5.5 to 6.2 Enteric Coated (EC) Symbiotic Granules/Pellets" (100 micron).

| Ingredients | Amount (%) |
|---|---|
| L. Leucine (prebiotic) | 5% |
| Freeze dried bacterial(species of *lactobacillus* and *bifidobacterium*) probiotic) | 1% |
| Excipients (Microcrystalline cellulose - filler, polyvinyl-pyrrolidone - binder, pregelatinized starch - disintegrant, silicon dioxaide - flow aid, magnesium stearate - lubricant) | 82% |
| HPMC or equivalent "polymers" (Barrier and Seal coats) | 2% |
| "Polymers" (pH 5.5 to 6.2 sensitive coating) | 10% |
| Water/Solvents as required | 0% |

Prepared by dry granulating pre-/probiotic with excipients and/or wet granulations with water solvents in high or low shear mixer and further pelletizing using extruder/spheronizer and then drying to remove water using optimized conditions. The above micropellets or granules are further coated (barrier coat) with aqueous or solvent coating solution of HPMC or equivalent "polymers" in a coating pan or fluid bed drier/coater using optimized conditions. The above barrier coated micropellets or granules are further coated with aqueous or solvent coating solution of "Polymers" (pH 5.5 to 6.2 sensitive coating) in a coating pan or fluid bed drier/coater using optimized conditions. The above pH 5.5 to 6.2 sensitive coated micropellets or granules are seal coated with aqueous or solvent coating solution of HPMC or equivalent "polymers" in a coating pan or fluid bed drier/coater using optimized conditions.

"pH 7.2 to 7.5 Enteric Coated (EC) Symbiotic Granules/Pellets" (100 micron).

| Ingredients | Amount (%) |
|---|---|
| pH 5.5 to 6.2 Enteric Coated (EC) Symbiotic Granules/Pellets | 88% |
| HPMC or equivalent "polymers" (Seal coats) | 2% |
| "Polymers" (pH 7.2 to 7.5 sensitive coating) | 10% |
| Water/Solvents as required | 0% |

The above pH 5.5 to 6.2 Enteric Coated (EC) Symbiotic Granules/Pellets are coated with aqueous or solvent coating solution of "Polymers" (pH 7.2 to 7.5 sensitive coating) in a coating pan or fluid bed drier/coater using optimized conditions. The above micropellets or granules are further coated with aqueous or solvent coating solution of HPMC or equivalent "polymers" (seal coat) in a coating pan or fluid bed drier/coater using optimized conditions.

Example: Final Product—Sachet—Formulation/Manufacturing Process (at local CMO, controlled room and humidity conditions throughout the process):

| Ingredients | Amount (%) |
|---|---|
| Uncoated Antibiotic Granules/Pellets | 50% |
| pH 5.0 to 6.0 Enteric Coated (EC) Antibiotic Granules/Pellets | 25% |
| pH 7.2 to 7.5 Enteric Coated (EC) Symbiotic Granules/Pellets | 15% |
| Excipients (Mannitol - filler, Silicon dioxide - glidant/flow aid) | 10% |

The above Uncoated Antibiotic Granules/Pellets, pH 5.0 to 6.0 Enteric Coated (EC) Antibiotic Granules/Pellets and pH 7.2 to 7.5 Enteric Coated (EC) Symbiotic Granules/Pellets intermediate formulations are blended in desired portions in V-type or similar blender with excipients using optimized conditions. The blended powders are filling into sachets using powder filling equipment.

Example: Final Product—Capsules (Hard gelatin/HPMC)—Formulation/Manufacturing Process (at local CMO, controlled room and humidity conditions throughout the process):

| Ingredients | Amount (%) |
|---|---|
| Uncoated Antibiotic Granules/Pellets | 45% |
| pH 5.0 to 6.0 Enteric Coated (EC) Antibiotic Granules/Pellets | 20% |
| pH 7.2 to 7.5 Enteric Coated (EC) Symbiotic Granules/Pellets | 12% |
| Excipients (Microcrystalline cellulose - filler, Silicon dioxide - glidant/flow aid) | 13% |
| Hard Gelatin/HPMC Capsules | 10% |

The above Uncoated Antibiotic Granules/Pellets, pH 5.0 to 6.0 Enteric Coated (EC) Antibiotic Granules/Pellets and pH 7.2 to 7.5 Enteric Coated (EC) Symbiotic Granules/Pellets intermediate formulations are blended in desired portions in V-type or similar blender with excipients. The blended powders are filled into capsules using encapsulating equipment.

Example: Final Product—Capsules (Liquid Filled Hard or Soft Gelatin)—Formulation/Manufacturing Process (at local CMO, controlled room and humidity conditions throughout the process):

| Ingredients | Amount (%) |
|---|---|
| Uncoated Antibiotic Granules/Pellets | 35% |
| pH 5.0 to 6.0 Enteric Coated (EC) Antibiotic Granules/Pellets | 10% |
| pH 7.2 to 7.5 Enteric Coated (EC) Symbiotic Granules/Pellets | 10% |
| Vegetable oil (immiscible liquid) | 40% |
| Gelatin as powder and Hard Gelatin Capsules | 5% |

The above Uncoated Antibiotic Granules/Pellets, pH 5.0 to 6.0 Enteric Coated (EC) Antibiotic Granules/Pellets and pH 7.2 to 7.5 Enteric Coated (EC) Symbiotic Granules/Pellets intermediate formulations are blended in desired portions with immiscible liquid in a blender. Filled into capsules using soft or hard gelatin encapsulating equipment using optimized conditions.

Example: Final Product—Capsule-in-Capsule (Hard gelatin) (1)—Formulation/Manufacturing Process (at local CMO, controlled room and humidity conditions throughout the process):

| Ingredients | Amount (%) |
|---|---|
| pH 7.2 to 7.5 Enteric Coated (EC) Symbiotic Granules/Pellets | 12% |
| Uncoated Antibiotic Granules/Pellets | 45% |
| pH 5.0 to 6.0 Enteric Coated (EC) Antibiotic Granules/Pellets | 25% |
| Excipients (Microcrystalline cellulose - filler, Silicon dioxide - glidant/flow aid) | 10% |
| Small and Large Hard Gelatin/HPMC Capsules | 8% |

The pH 7.2 to 7.5 Enteric Coated (EC) Symbiotic Granules/Pellets intermediate formulation is blended in with portion of excipients in V-type or similar blender and the blend. The blend is filled into smaller capsules using encapsulating equipment and optimized conditions. The above Uncoated Antibiotic Granules/Pellets and pH 5.0 to 6.0 Enteric Coated (EC) Antibiotic Granules/Pellets intermediate formulations are blended together in desired portions in V-type or similar blender with excipients. The blended intermediate formulations along with the smaller filled capsules are further filled into larger capsules using specialized capsule filling equipment and optimized conditions.

Example: Final Product—Capsule-in-Capsule (Hard gelatin) (2)—Formulation/Manufacturing Process (at local CMO, controlled room and humidity conditions throughout the process):

| Ingredients | Amount (%) |
|---|---|
| pH 5.5 to 6.2 Enteric Coated (EC) Symbiotic Granules/Pellets | 15% |
| "Polymers" (pH 7.2 to 7.5 sensitive coating) | 10% |
| Uncoated Antibiotic Granules/Pellets | 45% |
| Excipients (Microcrystalline cellulose - filler, Silicon dioxide - glidant/flow aid) | 10% |
| pH 5.0 to 6.0 Enteric Coated (EC) Antibiotic Granules/Pellets | 10% |
| Small and Large Hard Gelatin/HPMC Capsules | 10% |
| Water/Solvents as required | 0% |

The pH 5.5 to 6.2 Enteric Coated (EC) Symbiotic Granules/Pellets intermediate formulation is blended in desired portions in V-type or similar blender with excipients. The blend is filled into smaller capsules using encapsulating equipment. The smaller filled capsules are further coated with pH 7.2 to 7.5 sensitive coating using aqueous or solvent coating solution of "Polymers" in a coating pan or fluid bed drier/coater with optimized conditions. The above Uncoated Antibiotic Granules/Pellets and pH 5.0 to 6.0 Enteric Coated (EC) Antibiotic Granules/Pellets intermediate formulations are blended in desired portions in V-type or similar blender with excipients. The smaller pH 7.2 to 7.5 coated capsules and the blends are further filled into larger capsules using specialized capsule filling equipment and optimized conditions.

Example: Final Product—Tablets/Microtablets—Formulation/Manufacturing Process (at local CMO, controlled room and humidity conditions throughout the process):

| Ingredients | Amount (%) |
|---|---|
| Uncoated Antibiotic Granules/Pellets | 45% |
| pH 5.0 to 6.0 Enteric Coated (EC) Antibiotic Granules/Pellets | 12% |
| pH 7.2 to 7.5 Enteric Coated (EC) Symbiotic Granules/Pellets | 12% |
| Excipients (Microcrystalline cellulose - filler, polyvinylpyrrolidone - binder, pregelatinized starch - disintegrant and silicon dioxide - flow aid, magnesium stearate - lubricant) | 30% |
| HPMC or equivalent "polymers" (Film coat) | 1% |
| Water/Solvents as required | 0% |

The Uncoated Antibiotic Granules/Pellets, pH 5.0 to 6.0 Enteric Coated (EC) Antibiotic Granules/Pellets and pH 7.2 to 7.5 Enteric Coated (EC) Symbiotic Granules/Pellets intermediate formulations are blended in desired portions in V-type or similar blender with excipients to aid in flow, disintegration and lubrication (for tableting machine). The blended powders are compressed into Tablets/Microtablets using tableting equipment. The tablets are further film coated using aqueous or solvent coating solution in a coating pan or fluid bed dryer using HPMC or equivalent "polymers" (Film coat).

Example: Final Product—Orally disintegrating Tablets (ODT)—Formulation/Manufacturing Process (at local CMO, controlled room and humidity conditions throughout the process):

| Ingredients | Amount (%) |
|---|---|
| Uncoated Antibiotic Granules/Pellets | 45% |
| pH 5.0 to 6.0 Enteric Coated (EC) Antibiotic Granules/Pellets | 12% |
| pH 7.2 to 7.5 Enteric Coated (EC) Symbiotic Granules/Pellets | 12% |
| Excipients (Mannitol - filler, polyvinylpyrrolidone - binder, pregelatinized starch - disintegrant and silicon dioxide - flow aid, magnesium stearate - lubricant) | 31% |

The Uncoated Antibiotic Granules/Pellets, pH 5.0 to 6.0 Enteric Coated (EC) Antibiotic Granules/Pellets and pH 7.2 to 7.5 Enteric Coated (EC) Symbiotic Granules/Pellets intermediate formulations are blended in desired portions in V-type or similar blender with excipients. The blended powders are compressed into soft tablets using tableting equipment.

Example: Final Product—Tablet-in-Tablet (1)—Formulation/Manufacturing Process (at local CMO, controlled room and humidity conditions throughout the process):

| Ingredients | Amount (%) |
|---|---|
| Uncoated Antibiotic Granules/Pellets | 45% |
| pH 5.0 to 6.0 Enteric Coated (EC) Antibiotic Granules/Pellets | 12% |
| pH 7.2 to 7.5 Enteric Coated (EC) Symbiotic Granules/Pellets | 12% |
| Excipients (Microcrystalline cellulose - filler, polyvinylpyrrolidone - binder, pregelatinized starch - disintegrant and silicon dioxide - flow aid, magnesium stearate - lubricant) | 30% |
| HPMC or equivalent "polymers" (Film coat) | 1% |
| Water/Solvents as required | 0% |

The pH 7.2 to 7.5 Enteric Coated (EC) Symbiotic Granules/Pellets intermediate formulation is blended in desired portions in V-type or similar blender with excipients to aid in flow, disintegration and lubrication (for tableting machine). The blended powders are compressed into small tablets/Microtablets using tableting equipment. The above Uncoated Antibiotic Granules/Pellets, and pH 5.0 to 6.0 Enteric Coated (EC) Antibiotic Granules/Pellets intermediate formulations are blended in desired portions in V-type or similar blender with excipients to aid in flow, disintegration and lubrication (for tableting machine). The blended powder is compress coated over the small tablets/Microtablets using compress coat tableting machine. The tablets are further film coated using aqueous or solvent coating solution in a coating pan or fluid bed dryer using HPMC or equivalent "polymers" (Film coat).

Final Product—Tablet-in-Tablet (2)—Formulation/Manufacturing Process (at local CMO, controlled room and humidity conditions throughout the process):

| Ingredients | Amount (%) |
|---|---|
| Uncoated Antibiotic Granules/Pellets | 45% |
| pH 5.0 to 6.0 Enteric Coated (EC) Antibiotic Granules/Pellets | 12% |
| pH 5.5 to 6.2 Enteric Coated (EC) Symbiotic Granules/Pellets | 12% |

| Ingredients | Amount (%) |
| --- | --- |
| Excipients (Microcrystalline cellulose-filler, polyvinyl-pyrrolidone-binder, pregelatinized starch-disintegrant and silicon dioxide-flow aid, magnesium stearate-lubricant) | 25% |
| "Polymers" (pH 7.2 to 7.5 sensitive coating) | 5% |
| HPMC or equivalent "polymers" (Film coat) | 1% |
| Water/Solvents as needed | 0% |

The pH 5.5 to 6.2 Enteric Coated (EC) Symbiotic Granules/Pellets intermediate formulation is blended in desired portions in V-type or similar blender with excipients to aid in flow, disintegration and lubrication (for tableting machine). The blended powders are compressed into small tablets/Microtablets using tableting equipment. The compressed tablets are coated with pH 7.2 to 7.5 sensitive coating using aqueous or solvent coating solution of "Polymers" in a coating pan or fluid bed drier/coater with optimized conditions ("EC tablets"). The above Uncoated Antibiotic Granules/Pellets, and pH 5.0 to 6.0 Enteric Coated (EC) Antibiotic Granules/Pellets intermediate formulations are blended in desired portions in V-type or similar blender with additional excipients to aid in flow, disintegration and lubrication (for tableting machine). The blended powder is compress coated over the small EC tablets/Microtablets using compress coat tableting machine. The tablets are further film coated using aqueous or solvent coating solution in a coating pan or fluid bed dryer using HPMC or equivalent "polymers" (Film coat).

Example: Final Product—Tablet-in-Capsule (Hard gelatin) (1)—Formulation/Manufacturing Process (at local CMO, controlled room and humidity conditions throughout the process):

| Ingredients | Amount (%) |
| --- | --- |
| Uncoated Antibiotic Granules/Pellets | 45% |
| pH 5.0 to 6.0 Enteric Coated (EC) Antibiotic Granules/Pellets | 13% |
| pH 7.2 to 7.5 Enteric Coated (EC) Symbiotic Granules/Pellets | 13% |
| Excipients (Microcrystalline cellulose-filler, polyvinyl-pyrrolidone-binder, pregelatinized starch-disintegrant and silicon dioxide-flow aid, magnesium stearate-lubricant) | 24% |
| Hard Gelatin/HPMC Capsules | 5% |

The Uncoated Antibiotic Granules/Pellets, pH 5.0 to 6.0 Enteric Coated (EC) Antibiotic Granules/Pellets and pH 7.2 to 7.5 Enteric Coated (EC) Symbiotic Granules/Pellets intermediate formulations are blended in desired portions in V-type or similar blender with excipients to aid in flow, disintegration and lubrication (for tableting machine). The blended powders are compressed into Tablets/Microtablets using tableting equipment. The excipients and the tablets filled into hard gelatin capsules using specialized encapsulating equipment.

Example: Final Product—Tablet-in-Capsule (Hard gelatin) (2)—Formulation/Manufacturing Process (at local CMO, controlled room and humidity conditions throughout the process):

| Ingredients | Amount (%) |
| --- | --- |
| Uncoated Antibiotic Granules/Pellets | 45% |
| pH 5.0 to 6.0 Enteric Coated (EC) Antibiotic Granules/Pellets | 13% |
| pH 7.2 to 7.5 Enteric Coated (EC) Symbiotic Granules/Pellets | 13% |
| Excipients (Microcrystalline cellulose-filler, polyvinyl-pyrrolidone-binder, pregelatinized starch-disintegrant and silicon dioxide-flow aid, magnesium stearate-lubricant) | 24% |
| Hard Gelatin/HPMC Capsules | 5% |

The pH 7.2 to 7.5 Enteric Coated (EC) Symbiotic Granules/Pellets intermediate formulations are blended in desired portions in V-type or similar blender with excipients to aid in flow, disintegration and lubrication (for tableting machine). The blended powders are compressed into small tablets/Microtablets using tableting equipment. The above Uncoated Antibiotic Granules/Pellets, and pH 5.0 to 6.0 Enteric Coated (EC) Antibiotic Granules/Pellets intermediate formulations are blended in desired portions in V-type or similar blender with additional excipients to aid in flow, disintegration and lubrication (for tableting machine). The blended powder and tablets are filled into large Hard Gelatin Capsules using encapsulating equipment.

Example: Final Product—Tablet-in-Capsule (Hard gelatin) (3)—Formulation/Manufacturing Process (at local CMO, controlled room and humidity conditions throughout the process):

| Ingredients | Amount (%) |
| --- | --- |
| Uncoated Antibiotic Granules/Pellets | 45% |
| pH 5.0 to 6.0 Enteric Coated (EC) Antibiotic Granules/Pellets | 13% |
| pH 5.5 to 6.2 Enteric Coated (EC) Symbiotic Granules/Pellets | 13% |
| Excipients (Microcrystalline cellulose-filler, polyvinyl-pyrrolidone-binder, pregelatinized starch-disintegrant and silicon dioxide-flow aid, magnesium stearate-lubricant) | 20% |
| "Polymers" (pH 7.2 to 7.5 sensitive coating) | 4% |
| Hard Gelatin/HPMC Capsules | 5% |
| Water/Solvents as required | 0% |

The pH 5.5 to 6.2 Enteric Coated (EC) Symbiotic Granules/Pellets intermediate formulations are blended in desired portions in V-type or similar blender with excipients to aid in flow, disintegration and lubrication (for tableting machine). The blended powders are compressed into small tablets/Microtablets using tableting equipment. The compressed tablets are coated with pH 7.2 to 7.5 sensitive coating using aqueous or solvent coating solution of "Polymers" in a coating pan or fluid bed drier/coater with optimized conditions ("EC tablets"). The above Uncoated Antibiotic Granules/Pellets, and pH 5.0 to 6.0 Enteric Coated (EC) Antibiotic Granules/Pellets intermediate formulations are blended in desired portions in V-type or similar blender with excipients to aid in flow, disintegration and lubrication (for tableting machine). The blended powder and the EC tablets are filled into a larger capsule using encapsulating equipment.

Example: Final Product—Bi-Layer Tablets—Formulation/Manufacturing Process (at local CMO, controlled room and humidity conditions throughout the process):

| Ingredients | Amount (%) |
|---|---|
| Uncoated Antibiotic Granules/Pellets | 45% |
| pH 5.0 to 6.0 Enteric Coated (EC) Antibiotic Granules/Pellets | 13% |
| Excipients (Microcrystalline cellulose-filler, polyvinyl-pyrrolidone-binder, pregelatinized starch-disintegrant and silicon dioxide-flow aid, magnesium stearate-lubricant) | 28% |
| pH 7.2 to 7.5 Enteric Coated (EC) Symbiotic Granules/Pellets | 13% |
| HPMC or equivalent "polymers" (Film coat) | 1% |
| Water/Solvents as required | 0% |

The above Uncoated Antibiotic Granules/Pellets, and pH 5.0 to 6.0 Enteric Coated (EC) Antibiotic Granules/Pellets intermediate formulations are blended in desired portions in V-type or similar blender with excipients to aid in flow, disintegration and lubrication (for tableting machine). The blended powders are compressed into tablets using bi-layer tableting equipment ("EC Tablets"). The pH 7.2 to 7.5 Enteric Coated (EC) Symbiotic Granules/Pellets intermediate formulations are blended in desired portions in V-type or similar blender with excipients to aid in flow, disintegration and lubrication (for tableting machine). The blended powder is compressed over the EC tablets using bilayer tableting machine. The tablets are further film coated using aqueous or solvent coating solution in a coating pan or fluid bed dryer using HPMC or equivalent "polymers" (Film coat).

Example: Final Product—Tri-Layer Tablets—Formulation/Manufacturing Process (at local CMO, controlled room and humidity conditions throughout the process):

| Ingredients | Amount (%) |
|---|---|
| Uncoated Antibiotic Granules/Pellets | 45% |
| Excipients (Microcrystalline cellulose-filler, polyvinyl-pyrrolidone-binder, pregelatinized starch-disintegrant and silicon dioxide-flow aid, magnesium stearate-lubricant) | 28% |
| pH 5.0 to 6.0 Enteric Coated (EC) Antibiotic Granules/Pellets | 13% |
| pH 7.2 to 7.5 Enteric Coated (EC) Symbiotic Granules/Pellets | 13% |
| HPMC or equivalent "polymers" (Film coat) | 1% |
| Water/Solvents as required | 0% |

The above Uncoated Antibiotic Granules/Pellets intermediate formulations is blended in desired portions in V-type or similar blender with excipients to aid in flow, disintegration and lubrication (for tableting machine). The blended powders are compressed into tablets using tri-layer tableting equipment ("EC Tablets-1"). The above pH 5.0 to 6.0 Enteric Coated (EC) Antibiotic Granules/Pellets intermediate formulation is blended in desired portions in V-type or similar blender with additional excipients to aid in flow, disintegration and lubrication (for tableting machine). The blend is compressed over the first layer of tablets (EC Tablets-1) using tri-layer tableting equipment ("EC Tablets-2"). The pH 7.2 to 7.5 Enteric Coated (EC) Symbiotic Granules/Pellets intermediate formulations are blended in desired portions in V-type or similar blender with additional excipients to aid in flow, disintegration and lubrication (for tableting machine). The blended powder is compressed over the second layer of tablets (EC tablets-2) using tri-layer tableting machine. The tablets are further film coated using aqueous or solvent coating solution in a coating pan or fluid bed dryer using HPMC or equivalent "polymers" (Film coat).

Final Product Packaging (at local CMO, dry low humidity and low oxygen (N2 purging) conditions throughout the process):

The above granules are packaged in sachet, and the coated tablets, capsules are packaged into bottles with induction sealing or blistered at low humidity (at or below 40% RH) and controlled room temperature conditions (at 20 to 25 degrees C.).

Quality Control Release Testing (Active Pharmaceutical Ingredient (API) and Final Drug Product) Symbiotic—

| Test | Methods and Assessment |
|---|---|
| Description | Granules, pellets, tablets, capsules in blisters or bottles or sachets |
| Appearance | Visual inspection for color, shape, etc. |
| Identification | Genes, species, strains. Morphological appearance via Microscopic evaluation and/or multiplex PCR as well as other tests including biochemical methods such as fermentation profile or genotypic methods, e.g. ribotyping, restriction fragment length polymorphism (RFLP), or both. In addition, develop a specific identity assay for critical biological activity. Others test may include: DNA-DNA hybridization to specify strains in species; DNA sequence coding per WHO; Strain typing include Pulsed Field Gel electrophoresis (PFGE), etc. |
| Potency - Viable organisms | Microscopic testing, or Opacity to measure viable cells per unit or dose, i.e. colony forming units (CFU) |
| Potency Assay | Assessment of CFU (on solid medium) and tests to correlating with activity. M-viability plating. |
| Purity | Endotoxin content, residual antibiotics, and/or the quantification of residual toxic components or contaminants introduced during manufacture by Elisa or amino acid profile |
| Microbial bioburden or contaminants and limits | Extraneous materials including pathogens by using Elisa or amino acid profile or SDS page or ion exchange chromatography, etc. Microbial limits by US Pharmacopeia (USP 31 <61>). |
| Percent viable cells | Micro testing after regrown in appropriate media and test, e.g., Dead/live assay by ATP. Also determination of non-viable units per g i.e., by electro-zone count of non- fluorescent cells (SDS PAGE) |
| Particulate matter | USP 31 <788> |
| Pyrogens | TBD |
| pH Testing | pH meter |
| Residual moisture | Water content, USP 31 <921> |
| Content Uniformity | TBD |
| Package Integrity | Leaker test by vacuum |
| Stability | Potency, viable cell determination, microbial contamination, pH an residual moisture |

Antibiotic(s)

| Test | Methods and Assessment |
|---|---|
| Identification | HPLC and other |
| Assay | HPLC and other |
| Impurities and Related sub | HPLC and other |
| Content uniformity | HPLC and other |

Symbiotic and Antibiotic

| Test | Methods and Assessment |
|---|---|
| In-vitro release testing (via dissolution testing equipment): USP paddle or basket | Medium: pH 1 buffer (simulated gastric), pH 6 buffer, pH 7.2 to 7.5 buffer (simulated intestinal fluid), followed by pH 5.5-6.2 buffer (simulated colonic fluid). Sample Times: pH 1 buffer-1 hour pH 6 buffer-1 hour |

| Test | Methods and Assessment |
|---|---|
| | pH 7.2 to 7.5-1, 2, 3 and 4 hours |
| | pH 5.5 to 6.2-1, 2, 4 and 8 hours |
| | Symbiotic Assay: |
| | Microbiology testing for count (cfu/gram) for |
| | Antibiotic Assay: |
| | HPLC |
| Stability testing (0, 6, | Symbiotic: |
| 12, 18 and 24 months): | Identification, Potency, viable cell determination, microbial contamination, pH and residual moisture, etc. |
| | Antibiotic: |
| | Identification, Assay, Impurities, Related Substances, microbial contamination, pH and residual moisture, etc. |

Fecal Microbiota Transplantation (MET).

Materials and Methods:

Described below are formulations that are being made and tested for the target delivery for testing in biological assays, the formulation having an Healthy human bacterial fecal flora for release at pH 5.5-6.2 in right colon every 24 hours.

Active Pharmaceutical Ingredient (API):

Human bacterial fecal flora donated by health human volunteers, screened for safety.

Osmotic agents: proteins (casein, hydrolyzed protein, etc.), peptides, amino acids (L-Leucine), carbohydrates glucose, lactose, starches, inulin, sodium chloride, phosphate buffers, etc. Lallemand and other high quality global suppliers.

Inactive Ingredients (Excipients):

Fillers and carriers: Microcrystalline, starch, HPMC or equivalent "polymers", hard HPMC capsules, soft gelatin and other materials, etc.—purchased from local US supplier such as FMC, Capsugel, Colorcon, as well as pregelatinized starch—disintegrant, silicon dioxide—flow aid, magnesium stearate—lubricant) from various reputable excipient suppliers.

Intermediate Formulation/Manufacturing Process (at local CMO): "Dried Healthy Human Bacterial Fecal Flora":

| Ingredients | Amount (%) |
|---|---|
| Healthy human donor's bacterial fecal flora | 40% |
| Inactive ingredients-L. Leucine, sodium chloride, and/or dextrose, etc. | 40% |
| Inactive ingredients-phosphate buffer, tylexopol, and/or sodium glutamate, etc. | 20% |
| Water as required | 0% |

Dissolve the phosphate buffer, sodium chloride, and/or dextrose, etc. in water. Add the healthy human donor's bacterial fecal flora material to the mix and stir in a mixer. Pass the suspension through a large mesh filter to remove insoluble material (flora mix). Dissolve the phosphate buffer, tylexopol, and/or sodium glutamate, etc. in water and the dilute the flora mix. Fill into vials and freeze dry the mix or pass through sprayer drier or foam drier to remove moisture and produce fine powder.

"Dried Human Bacterial Fecal Flora Granules" (75-100 micron range):

| Ingredients | Amount (%) |
|---|---|
| Dried Human Bacterial Fecal Flora | 25% |
| Excipients (Microcrystalline cellulose-filler, pregelatinized starch-disintegrant, silicon dioxide-flow aid, magnesium stearate-lubricant) | 75% |

Prepare a dry granulation with Dried Human Bacterial Fecal Flora and excipients in a low shear mixer.

Example: Final Product—Capsules (HPMC)—Formulation/Manufacturing Process (at local CMO, controlled room temperature, humidity and oxygen conditions throughout the process):

| Ingredients | Amount (%) |
|---|---|
| Dried Human Bacterial Fecal Flora | 15% |
| Polymers" (pH 5.5 to 6.2 sensitive coating) | 25% |
| Polymers" (pH 7.2 to 7.5 sensitive coating) | 25% |
| HPMC or equivalent "polymers" (Barrier and Seal coats) | 5% |
| HPMC Capsules | 30% |

The above Dried Human Bacterial Fecal Flora is filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Capsules (HPMC)—Formulation/Manufacturing Process (at local CMO, controlled room temperature, humidity and oxygen conditions throughout the process):

| Ingredients | Amount (%) |
|---|---|
| Dried Human Bacterial Fecal Flora Granules | 68% |
| Polymers" (pH 5.5 to 6.2 sensitive coating) | 10% |
| Polymers" (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora Granules are filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Liquid Filled Soft Gelatin/Veggie Gel Capsules—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 15% |
| Vegetable oil (immiscible liquid) and/or other no-aqueous ingredients (paste) | 53% |
| Polymers" (pH 5.5 to 6.2 sensitive coating) | 10% |
| Polymers" (pH 7.2 to 7.5 sensitive coating) | 10% |
| HPMC or equivalent "polymers" (Barrier and Seal coats) | 2% |
| Vegetable gel mix or gelatin for producing veggie or soft gelatin capsules | 10% |

The above Dried Human Bacterial Fecal Flora is mixed with Vegetable oil (immiscible liquid) and/or other no-aqueous ingredients (paste) in a blender using optimum conditions. The mixture is filled with vegetable gel mix or gelatin in an encapsulation equipment for producing veggie or soft gelatin capsules. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Liquid Filled Hard Capsules (e.g. HPMC)—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 15% |
| Vegetable oil (immiscible liquid) and/or other no-aqueous ingredients (paste) | 53% |
| Polymers" (pH 5.5 to 6.2 sensitive coating) | 10% |
| Polymers" (pH 7.2 to 7.5 sensitive coating) | 10% |
| HPMC or equivalent "polymers" (Barrier and Seal coats) | 2% |
| Hard Gelatin/HPMC capsules | 10% |

The above Dried Human Bacterial Fecal Flora is mixed with Vegetable oil (immiscible liquid) and/or other no-aqueous ingredients (paste) in a blender using optimum conditions. The mixture is filled into hard HPMC capsules using an encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Capsule-in-Capsule (HPMC) (1)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 35% |
| Excipients (Microcrystalline cellulose ? filler, pregelatinized starch-disintegrant, silicon dioxide-flow aid, magnesium stearate-lubricant) | 33% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora Granules are filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The above Excipients along with the smaller filled capsules are further filled into larger capsules using specialized capsule filling equipment and optimized conditions. The larger capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Softgel Capsule-in-Capsule (e.g. soft gelatin) (2)—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 15% |
| Vegetable oil (immiscible liquid) and/or other no-aqueous ingredients (paste) | 53% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| Vegetable gel mix or gelatin for producing veggie or soft gelatin capsules | 10% |

The above Dried Human Bacterial Fecal Flora is filled with vegetable gel mix or gelatin in encapsulation equipment for producing veggie or soft gelatin capsules using optimum conditions. The veggie or soft gelatin capsules along with vegetable oil are together encapsulated using another encapsulation equipment for producing larger veggie or soft gelatin capsules. The larger capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Tablet-in-Capsule (Liquid Filled Soft Gelatin/Veggie Gel)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 35% |
| Vegetable oil (immiscible liquid) and/or other no-aqueous ingredients (paste) | 33% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| Vegetable gel mix or gelatin for producing veggie or soft gelatin capsules | 10% | coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Tablet-in-Capsule (HPMC)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 68% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora Granules are compressed into soft microtablets using compression machine and optimum conditions. The microtablets are then filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent The above Dried Human Bacterial Fecal Flora Granules are compressed into soft microtablets using compression machine and optimum conditions. The microtablets and the vegetable oil mix are filled with vegetable gel mix or gelatin in an encapsulation equipment for producing veggie or soft gelatin capsules. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Final Product Packaging (at local CMO, dry low humidity and low oxygen (N2 purging) conditions throughout the process). The above granules are packaged in sachet, and the coated tablets, capsules are packaged into bottles with induction sealing or blistered at low humidity (at or below 40% RH) and controlled room temperature conditions (at 20 to 25 degrees C.).

Quality Control Release Testing (Active Pharmaceutical Ingredient (API) and Final Drug Product)
Human Bacterial Fecal Flora

| Test | Methods and Assessment |
|---|---|
| Description | Powder, Granules, capsules in blisters or bottles or sachets |
| Appearance | Visual inspection for color, shape, etc. |
| Identification | Genes, species, strains. Morphological appearance via Microscopic evaluation and/or multiplex PCR as well as other tests including biochemical methods such as fermentation profile or genotypic methods, e.g. ribotyping, restriction fragment length polymorphism (RFLP), or both. In addition, develop a specific identity assay for critical biological activity. Others test may include: DNA-DNA hybridization to specify strains in species; DNA sequence coding per WHO; Strain typing include Pulsed Field Gel electrophoresis (PFGE), etc. |
| Potency-Viable organisms | Microscopic testing, or Opacity to measure viable cells per unit or dose, i.e. colony forming units (CFU) |
| Potency Assay | Assessment of CFU (on solid medium) and tests to correlating with activity. M-viability plating. Elisa or amino acid profile. |
| Purity/Related substances | Endotoxin content, antibiotic residue and/or the quantification of residual toxic components or contaminants introduced during manufacture by Elisa or amino acid profile; SDS page and or amino acid profile. |
| Microbial bioburden or contaminants and limits (related substances) | Extraneous materials including pathogens by using Elisa or amino acid profile or SDS page or ion exchange chromatography, etc. Microbial limits by US Pharmacopeia (USP 31 <61>). |
| Percent viable cells | Micro testing after regrown in appropriate media and test, e.g., Dead/live assay by ATP. Also determination of non-viable units per g i.e., by electro-zone count of non-fluorescent cells (SDS PAGE) |
| Particulate matter | USP 31 <788> |
| Pyrogens | TBD |
| pH Testing | pH meter |
| Residual moisture | Water content, USP 31 <921> |
| Content Uniformity | ATP |
| Live/Dead Assay | ATP |
| Heavy metals | Inductively Coupled Plasma-Atomic Emission Spectrophotometry (ICP-AES); Inductively Coupled Plasma-Mass Spectroscopy (ICP-MS); Atomic Emission Spectrophotometry (AES); or Atomic Absorption Spectrophotometry (AAS). |
| Water content | Karl Fischer |
| Package Integrity | Leaker test by vacuum |
| Stability | Potency, viable cell determination, microbial contamination, pH an residual moisture |
| In-vitro release testing (via dissolution testing equipment): | USP paddle or basket Medium: pH 1 buffer (simulated gastric), pH 6 buffer, pH 7.2 to 7.5 buffer (simulated intestinal fluid), followed by pH 5.5-6.2 buffer (simulated colonic fluid). Sample Times: pH 1 buffer-1 hour pH 5.5-6.2 buffer-1,2,3 and 4 hours pH 7.2 to 7.5-1, 2, 3 and 4 hours pH 5.5 to 6.2 -1, 2, 4 and 8 hours Human Bacterial Fecal Flora-Assay: Microbiology testing for count (cfu/gram) |
| Stability testing (0, 6, 12, 18 and 24 months): | Identification, Appearance, Potency, viable cell determination, microbial contamination, pH and residual moisture, related substance, water content, Live/dead Assay,etc. |

Fecal Microbiota Transplantation (MET) with *C. difficile* Anti-Toxin (CDAT)

Materials and Methods:

Described below are formulations that are being made and tested for the target delivery for testing in biological assays, the formulation having an Healthy human bacterial fecal flora for release at pH 5.5-6.2 in right colon every 24 hours.

Active Pharmaceutical Ingredient (API):

Human bacterial fecal flora donated by health human volunteers, screened for safety.

*C. difficile* anti-toxin (CDAT) provided from specialty supplier

Osmotic agents: proteins (casein, hydrolyzed protein, etc.), peptides, amino acids (L-Leucine), carbohydrates glucose, lactose, starches, inulin, sodium chloride, phosphate buffers, etc. Lallemand and other high quality global suppliers.

Inactive Ingredients (Excipients):

Fillers and carriers: Microcrystalline, starch, HPMC or equivalent "polymers", hard HPMC capsules, soft gelatin and other materials, etc.—purchased from local US supplier such as FMC, Capsugel, Colorcon, as well as pregelatinized starch—disintegrant, silicon dioxide—flow aid, magnesium stearate—lubricant) from various reputable excipient suppliers.

Intermediate Formulation/Manufacturing Process (at Local CMO): "Dried Healthy Human Bacterial Fecal Flora":

| Ingredients | Amount (%) |
| --- | --- |
| Healthy human donor's bacterial fecal flora | 40% |
| Inactive ingredients-L. Leucine, sodium chloride, and/or dextrose, etc. | 40% |
| Inactive ingredients-phosphate buffer, tylexopol, and/or sodium glutamate, etc. | 20% |
| Water as required | 0% |

Dissolve the phosphate buffer, sodium chloride, and/or dextrose, etc. in water. Add the healthy human donor's bacterial fecal flora material to the mix and stir in a mixer. Pass the suspension through a large mesh filter to remove insoluble material (flora mix). Dissolve the phosphate buffer, tylexopol, and/or sodium glutamate, etc. in water and the dilute the flora mix. Fill into vials and freeze dry the mix or pass through sprayer drier or foam drier to remove moisture and produce fine powder.

"Dried Human Bacterial Fecal Flora Granules" (75-100 micron range):

| Ingredients | Amount (%) |
| --- | --- |
| Dried Human Bacterial Fecal Flora | 25% |
| Excipients (Microcrystalline cellulose-filler, pregelatinized starch-disintegrant, silicon dioxide-flow aid, magnesium stearate-lubricant) | 75% |

Prepare a dry granulation with Dried Human Bacterial Fecal Flora and excipients in a low shear mixer. "CDAT Granules" (75-100 micron range):

| Ingredients | Amount (%) |
| --- | --- |
| CDAT | 25% |
| Excipients (Microcrystalline cellulose-filler, pregelatinized starch-disintegrant, silicon dioxide-flow aid, magnesium stearate-lubricant) | 75% |

Prepare a dry granulation with CDAT and excipients in a low shear mixer.

Example: Final Product—Capsules (HPMC)—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 10% |
| CDAT | 5% |
| Polymers (pH 5.5 to 6.2 sensitive coating) | 25% |
| Polymers (pH 7.2 to 7.5 sensitive coating) | 25% |
| HPMC or equivalent "polymers" (Barrier and Seal coats) | 5% |
| HPMC Capsules | 30% |

The above Dried Human Bacterial Fecal Flora and the CDAT is filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Capsules (HPMC)—Formulation/Manufacturing Process (at local CMO, controlled room temperature, humidity and oxygen conditions throughout the process):

| | |
| --- | --- |
| CDAT Granules | 34% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora and CDAT Granules are filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Liquid Filled Soft Gelatin/Veggie Gel Capsules—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 10% |
| CDAT | 5% |
| Vegetable oil (immiscible liquid) and/or other no-aqueous ingredients (paste) | 53% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| Vegetable gel mix or gelatin for producing veggie or soft gelatin capsules | 10% |

The above Dried Human Bacterial Fecal Flora and CDAT are mixed with Vegetable oil (immiscible liquid) and/or other no-aqueous ingredients (paste) in a blender using optimum conditions. The mixture is filled with vegetable gel mix or gelatin in encapsulation equipment for producing veggie or soft gelatin capsules. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Liquid Filled Hard Capsules (e.g. HPMC)—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 10% |
| CDAT | 5% |
| Vegetable oil (immiscible liquid) and/or other no-aqueous ingredients (paste) | 53% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| Hard Gelatin/HPMC capsules | 10% |

The above Dried Human Bacterial Fecal Flora and CDAT are mixed with Vegetable oil (immiscible liquid) and/or other no-aqueous ingredients (paste) in a blender using optimum conditions. The mixture is filled into hard HPMC capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Capsule-in-Capsule (HPMC) (1)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 23% |
| CDAT Granules | 12% |
| Excipients (Microcrystalline cellulose-filler, pregelatinized starch-disintegrant, silicon dioxide ? flow aid, magnesium stearate-lubricant) | 33% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora and CDAT Granules are filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The above Excipients along with the smaller filled capsules are further filled into larger capsules using specialized capsule filling equipment and optimized conditions. The larger capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Capsule-in-Capsule (HPMC) (2)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 23% |
| CDAT Granules | 12% |
| Excipients (Microcrystalline cellulose-filler, pregelatinized starch-disintegrant, silicon dioxide-flow aid, magnesium stearate-lubricant) | 33% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora are filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The above Excipients along with the, CDAT and smaller filled capsules are further filled into larger capsules using specialized capsule filling equipment and optimized conditions. The larger capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Softgel Capsule-in-Capsule (e.g. soft gelatin) (3)—Formulation/Manufacturing Process (at local CMO, controlled room temperature, humidity and oxygen conditions throughout the process):

| Ingredients | Amount (%) |
| --- | --- |
| Dried Human Bacterial Fecal Flora | 10% |
| CDAT | 5% |
| Vegetable oil (immiscible liquid) and/or other no-aqueous ingredients (paste) | 53% |
| Polymers (pH 5.5 to 6.2 sensitive coating) | 10% |
| Polymers (pH 7.2 to 7.5 sensitive coating) | 10% |
| HPMC or equivalent "polymers" (Barrier and Seal coats) | 2% |
| Vegetable gel mix or gelatin for producing veggie or soft gelatin capsules | 10% |

The above Dried Human Bacterial Fecal Flora is filled with vegetable gel mix or gelatin in encapsulation equipment for producing veggie or soft gelatin capsules using optimum conditions. The veggie or soft gelatin capsules along with vegetable oil are together encapsulated using another encapsulation equipment for producing larger veggie or soft gelatin capsules. The larger capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Tablet-in-Capsule (HPMC)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 45.3% |
| CDAT Granules | 22.7% |
| Polymers" (pH 5.5 to 6.2 sensitive coating) | 10% |
| Polymers" (pH 7.2 to 7.5 sensitive coating) | 10% |
| HPMC or equivalent "polymers" (Barrier and Seal coats) | 2% |
| HPMC Capsules | 10% |

The above Dried Human Bacterial Fecal Flora Granules are compressed into soft microtablets using compression machine and optimum conditions. The microtablets and the CDAT Granules are then filled into small capsules using encapsulation equipment. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Example: Final Product—Tablet-in-Capsule (Liquid Filled Soft Gelatin/Veggie Gel)—Formulation/Manufacturing Process (at local CMO, controlled room temperature, humidity and oxygen conditions throughout the process):

| Ingredients | Amount (%) |
| --- | --- |
| Dried Human Bacterial Fecal Flora Granules | 23% |
| CDAT | 12% |
| Vegetable oil (immiscible liquid) and/or other no-aqueous ingredients (paste) | 33% |
| Polymers" (pH 5.5 to 6.2 sensitive coating) | 10% |
| Polymers" (pH 7.2 to 7.5 sensitive coating) | 10% |
| HPMC or equivalent "polymers" (Barrier and Seal coats) | 2% |
| Vegetable gel mix or gelatin for producing veggie or soft gelatin capsules | 10% |

The above Dried Human Bacterial Fecal Flora Granules are compressed into soft microtablets using compression machine and optimum conditions. The microtablets, CDAT and the vegetable oil mix are filled with vegetable gel mix or gelatin in encapsulation equipment for producing veggie or soft gelatin capsules. The capsules are coated with pH 5.5 to 6.2 sensitive coating using aqueous or solvent coating solution of "Polymers" in a coating pan or fluid bed drier/coater using optimized conditions. The coated capsules are barrier coated with aqueous or solvent coating solution of HPMC or equivalent "polymers" in a coating pan or fluid bed drier/coater using optimized conditions. The film-coated capsules are further coated with pH 7.2 to 7.5 sensitive coating using aqueous or solvent coating solution of "Polymers" in a coating pan or fluid bed drier/coater using optimized conditions. The coated capsules are finally seal coated with aqueous or solvent coating solution of HPMC or equivalent "polymers" in a coating pan or fluid bed drier/coater using optimized conditions.

Final Product Packaging (at local CMO, dry low humidity and low oxygen (N2 purging) conditions throughout the process). The above granules are packaged in sachet, and the coated tablets, capsules are packaged into bottles with induction sealing or blistered at low humidity (at or below 40% RH) and controlled room temperature conditions (at 20 to 25 degrees C.).

Quality Control Release Testing (Active Pharmaceutical Ingredient (API) and Final Drug Product). Human Bacterial Fecal Flora—

| Test | Methods and Assessment |
| --- | --- |
| Description | Bacterial flora and CDAT: Powder, Granules, capsules in blisters or bottles or sachets |
| Appearance | Bacterial flora and CDAT: Visual inspection for color, shape, etc. |
| Identification | Bacterial flora: Genes, species, strains. Morphological appearance via Microscopic evaluation and/or multiplex PCR as well as other tests including biochemical methods such as fermentation profile or genotypic methods, e.g. ribotyping, restriction fragment length polymorphism (RFLP), or both. In addition, develop a specific identity assay for critical biological activity. Others test may include: DNA-DNA hybridization to specify strains in species; DNA sequence coding per WHO; Strain typing include Pulsed Field Gel electrophoresis (PFGE), etc. CDAT: Amino acid profile |
| Potency | Bacterial flora (Viable organisms): Microscopic testing, or Opacity to measure viable cells per unit or dose, i.e. colony forming units (CFU) CDAT: Elisa and amino acid profile |
| Potency Assay | Bacterial flora: Assessment of CFU (on solid medium) and tests to correlating with activity. M-viability plating. Elisa or amino acid profile. CDAT: Elisa and amino acid profile |
| Purity/Related substances | Bacterial flora: Endotoxin content, antibiotic residue and/or the quantification of residual toxic components or contaminants introduced during manufacture by Elisa or amino acid profile; SDS page and or amino acid profile. CDAT: Elisa or amino acid profile; SDS page and or amino acid profile. |
| Microbial bioburden or contaminants and limits (related substances) | Bacterial flora and CDAT: Extraneous materials including pathogens by using Elisa or amino acid profile or SDS page or ion exchange chromatography, etc. Microbial limits by US Pharmacopeia (USP 31 <61>). |
| Percent viable cells | Bacterial flora: Micro testing after regrown in appropriate media and test, e.g., Dead/live assay by ATP. Also determination of non-viable units per g i.e., by electro-zone count of non-fluorescent cells (SDS PAGE) |
| Particulate matter | Bacterial flora and CDAT: USP 31 <788> |
| Pyrogens | Bacterial flora and CDAT: TBD |
| pH Testing | Bacterial flora and CDAT: pH meter |
| Residual moisture | Bacterial flora and CDAT: Water content, USP 31 <921> |
| Content Uniformity | Bacterial flora: ATP CDAT: Elisa or amino acid profile |
| Live/Dead Assay | Bacterial flora: ATP |
| Heavy metals | Bacterial flora and CDAT: Inductively Coupled Plasma-Atomic Emission Spectrophotometry (ICP-AES); Inductively Coupled Plasma-Mass Spectroscopy (ICP-MS); Atomic Emission Spectrophotometry (AES); or Atomic Absorption Spectrophotometry (AAS). |
| Water content | Bacterial flora and CDAT: Karl Fischer |
| Package Integrity | Bacterial flora and CDAT: Leaker test by vacuum |
| Stability | Bacterial flora: Potency, viable cell determination, microbial contamination, pH an residual moisture CDAT: Potency, pH an residual moisture |
| In-vitro release testing (via dissolution testing equipment) : | Bacterial flora: USP paddle or basket Medium: pH 1 buffer (simulated gastric), pH 6 buffer, pH 7.2 to 7.5 buffer (simulated intestinal fluid), followed by pH 5.5-6.2 buffer (simulated colonic fluid). Sample Times: pH 1 buffer-1 hour pH 5.5-6.2 buffer-1, 2, 3 and 4 hours pH 7.2 to 7.5-1, 2, 3 and 4 hours pH 5.5 to 6.2-1, 2, 4 and 8 hours Human Bacterial Fecal Flora-Assay: Microbiology testing for count (cfu/gram) ; CDAT: Assay |
| Stability testing (0, 6, 12, 18 and 24 months): | Bacterial flora: Identification, Appearance, Potency, viable cell determination, microbial contamination, pH and residual moisture, related substance, water content, Live/dead Assay, etc. CDAT: Identification, Appearance, Potency, pH and residual moisture, related substance, water content, etc. |

Example 2: Obesity, Metabolic Syndrome and Type 2 Diabetes

Obesity results from alterations in the body's regulation of energy intake, expenditure, and storage. Animal and human data demonstrate that phylogenic changes occur in the microbiota composition in obese individuals. Furthermore, evidence from animal models suggest that the alterations of the gut microbiota with obesity results in increased energy extraction and lipid deposition, altered release of entero-hormones, increased intestinal permeability and metabolic endotoxemia. Treatment with pre- and probiotics may reverse many of metabolic effects linked with the altered microbiota in obese patients. The gut microbiota is, therefore, a potential nutritional and pharmacological target for the management of obesity and obesity-related disorders (12).

Materials and Methods:

Described below are methods and materials toward the making and testing of a formulation according to the invention for the treatment of Metabolic Syndrome, Obesity and type 2 diabetes.

Target Delivery: Target Delivery: Symbiotic (prebiotic: L-Leucine probiotic: live species of *Lactobacillus, Bifidobacterium* and *Faecalibacterium prausnitzii*) for release at 7.2-7.5 in ileum every 24 hours.

Active Pharmaceutical Ingredient (API): Prebiotics—proteins (casein, hydrolyzed protein, etc.), peptides, amino acids (L-Leucine), carbohydrates glucose, lactose, starches, dextrose monohydrate, inulin, etc.: provided by Roquette, etc. and certain bacterial strains: provided by Denisco, CHR Hansen, Institu Risell-Lallemand and other high quality global suppliers of prebiotics. Live probiotics Species of: *Lactobacillus, Bifidobacterium* and *Faecalibacterium prausnitzii* are provided by Denisco, CHR Hansen, Institu Risell-Lallemand and other high quality global suppliers.

Inactive Ingredients (Excipients): Microcrystalline, pregelatinized starch, polyvinylpyrrolidone, silicon dioxide, HPMC or equivalent "polymers", hard gelatin capsules, and other fillers, etc.—purchased from local US supplier such as FMC, Capsugel, Colorcon, Evonik, etc. Intermediate Formulation/Manufacturing Process (at local CMO, controlled room and humidity conditions throughout the process):

"Uncoated Symbiotic Granules/Pellets" (100 micron)

| Ingredients | Amount (%) |
| --- | --- |
| Freeze dried bacteria (species of *lactobacillus, bifidobacterium* and *faecalibacterium prausnitzii*) (probiotic) | 0.90% |
| L-Leucine | 0.1% |
| Excipients (Microcrystalline cellulose-filler, polyvinylpyrrolidone-binder, pregelatinized starch-disintegrant, silicon dioxide-flow aid, magnesium stearate-lubricant) | 99% |
| Water as required | 0% |

Prepared by mixing l-leucine, suspension or freeze dried bacteria (species of *Lactobacillus, Bifidobacterium* and *Faecalibacterium prausnitzii*) with water and further spray/freeze dried to remove water using optimized conditions. The probiotic powder is mixed with excipients in V-blender or similar blender.

"pH 7.2 to 7.5 Enteric Coated Symbiotic Granules/Pellets" (100 micron)

| Ingredients | Amount (%) |
| --- | --- |
| Uncoated Symbiotic Granules/Pellets | 95% |
| HPMC or equivalent "polymers" (Barrier and Seal coats) | 1% |
| "Polymers" (pH 7.2 to 7.5 sensitive coating) | 4% |
| Water/Solvents as required | 0% |

The Uncoated Symbiotic Granules/Pellets are coated (the barrier coat) with aqueous or solvent coating solution of HPMC or equivalent "polymers" to coat in a coating pan or fluid bed drier/coater using optimized conditions. The barrier coated micropellets or granules are further coated with aqueous or solvent coating solution of pH 7.2 to 7.5, sensitive coating "Polymers" in a coating pan or fluid bed drier/coater using optimized conditions. The above pH 7.2 to 7.5 sensitive coated micropellets or granules are seal coated with aqueous or solvent coating solution of HPMC or equivalent "polymers" in a coating pan or fluid bed drier/coater using optimized conditions.

"Uncoated Dextrose Monohydrate Pellets/Granules"

| Ingredients | Amount (%) |
| --- | --- |
| Dextrose monohydrate | 80% |
| Excipients (Microcrystalline cellulose-filler, polyvinylpyrrolidone-binder, pregelatinized starch-disintegrant, silicon dioxide-flow aid, magnesium stearate-lubricant) | 20% |
| Water as required | 0% |

Prepared by dry and/or wet granulating dextrose monohydrate, with excipients in high or low shear mixer and further pelletizing using extruder/spheronizer and then drying to remove water using optimized conditions.

"pH 7.2 to 7.5 Enteric Coated Dextrose Monohydrate Granules/Pellets" (100 micron)

| Ingredients | Amount (%) |
| --- | --- |
| Uncoated Dextrose Monohydrate Granules/Pellets | 95% |
| HPMC or equivalent "polymers" (Barrier and Seal coats) | 1% |
| "Polymers" (pH 7.2 to 7.5 sensitive coating) | 4% |
| Water/Solvents as required | 0% |

The Uncoated Dextrose Monohydrate Granules/Pellets are further coated (barrier coat) with aqueous or solvent coating solution of HPMC or equivalent "polymers" in a coating pan or fluid bed drier/coater using optimized conditions. The above micropellets or granules are further coated with aqueous or solvent coating solution of "Polymers" (pH 7.2 to 7.5 sensitive coating) in a coating pan or fluid bed drier/coater using optimized conditions. The above micropellets or granules are seal coated with aqueous or solvent coating solution of HPMC or equivalent "polymers" in a coating pan or fluid bed drier/coater using optimized conditions.

Example: Final Product—Sachet—Formulation/Manufacturing Process (at local CMO, controlled room and humidity conditions throughout the process):

| Intermediate Formulation | Amount (%) |
| --- | --- |
| pH 7.2 to 7.5 Enteric Coated (EC) Symbiotic Granules/Pellets | 5% |
| pH 7.2 to 7.5 Enteric Coated (EC) Dextrose Monohydrate Granules/Pellets | 90% |
| Excipients (Mannitol-filler, Silicon dioxide-glidant/flow aid) | 5% |

The above pH 7.2 to 7.5 Enteric Coated (EC) Symbiotic and Dextrose Monohydrate Granules/Pellets intermediate formulations are blended in desired portions in V-type or similar blender with excipients to aid in flow. The blended powders are filled into sachets using powder filling equipment.

Example: Final Product—Capsules (Hard gelatin/HPMC)—Formulation/Manufacturing Process (at local CMO, controlled room and humidity conditions throughout the process):

| Ingredients | Amount (%) |
| --- | --- |
| Uncoated Symbiotic Granules/Pellets | 1% |
| Uncoated Dextrose Monohydrate Granules/Pellets | 83% |
| Excipients (Microcrystalline cellulose-filler, Silicon dioxide-glidant/flow aid) | 7% |
| HardGelatin/HPMC Capsules | 7% |
| "Polymers" (pH 7.2 to 7.5 sensitive coating) | 2% |
| Water/Solvents as required | 0% |

The above Uncoated Symbiotic and Dextrose Monohydrate Granules/Pellets intermediate formulations are blended in desired portions in V-type or similar blender with excipients to aid in flow. The blended powders are filled into capsules using encapsulating equipment. The filled capsules are further coated with pH 7.2 to 7.5 sensitive coating using aqueous or solvent coating solution of "Polymers" in a coating pan or fluid bed drier/coater with optimized conditions.

Example: Final Product—Capsules (Hard gelatin/HPMC)—Formulation/Manufacturing Process (at local CMO, controlled room and humidity conditions throughout the process):

| Ingredients | Amount (%) |
| --- | --- |
| pH 7.2 to 7.5 Enteric Coated (EC) Symbiotic Granules/Pellets | 1% |
| pH 7.2 to 7.5 Enteric Coated (EC) Dextrose Monohydrate Granules/Pellets | 85% |
| Excipients (Microcrystalline cellulose-filler, Silicon dioxide-glidant/flow aid) | 7% |
| Hard Gelatin/HPMC Capsules | 7% |

The above pH 7.2 to 7.5 Enteric Coated (EC) Symbiotic and Dextrose Monohydrate Granules/Pellets intermediate formulations are blended in desired portions in V-type or similar blender with excipients to aid in flow. The blended powders are filled into capsules using encapsulating equipment Example: Final Product—Capsules (Hard gelatin/HPMC) (2)—Formulation/Manufacturing Process (at local CMO, controlled room and humidity conditions throughout the process):

| Ingredients | Amount (%) |
| --- | --- |
| Uncoated Symbiotic Granules/Pellets | 1% |
| Uncoated Dextrose Monohydrate Granules/Pellets | 81% |
| Excipients (Microcrystalline cellulose-filler, Silicon dioxide-glidant/flow aid) | 7% |
| Hard Gelatin/HPMC Capsules | 7% |
| "Polymers" (pH 7.2 to 7.5 sensitive coating) | 4% |
| Water/Solvents as required | 0% |

The above Uncoated Symbiotic and Dextrose Monohydrate Granules/Pellets intermediate formulations are blended in desired portions in V-type or similar blender with excipients to aid in flow. The blended powders are filled into capsules using encapsulating equipment. The filled capsules are enteric coated using aqueous or solvent coating solution of Polymers" (pH 7.2 to 7.5 sensitive coating) in coating pan or fluid bed coating equipment using optimized conditions.

Example: Final Product—Capsules Co-pack (2) (Hard Gelatin/HPMC capsules)—Formulation/Manufacturing Process (at local CMO, controlled room and humidity conditions throughout the process):

| Ingredients | Amount (%) |
| --- | --- |
| Uncoated Symbiotic Granules/Pellets | 1% |
| Uncoated Dextrose Monohydrate Granules/Pellets | 81% |
| Excipients (Microcrystalline cellulose-filler, Silicon dioxide-glidant/flow aid) | 7% |
| Hard Gelatin/HPMC Capsules | 7% |
| "Polymers" (pH 7.2 to 7.5 sensitive coating) | 4% |
| Water/Solvents as required | 0% |

The above Uncoated Symbiotic Granules/Pellets intermediate formulation is blended in desired portions in V-type or similar blender with excipients. The blended powders are filled into smaller capsules using encapsulating equipment. The filled capsules are enteric coated using aqueous or solvent coating solution of Polymers" (pH 7.2 to 7.5 sensitive coating) in coating pan or fluid bed coating equipment using optimized conditions. The above Uncoated Dextrose Monohydrate Granules/Pellets intermediate formulation is blended in desired portions in V-type or similar blender with excipients to aid in flow. The blended powders are filled into capsules using encapsulating equipment. The filled capsules are enteric coated using aqueous or solvent coating solution of Polymers" (pH 7.2 to 7.5 sensitive coating) in coating pan or fluid bed coating equipment using optimized conditions. The Two capsules products are co-packed Example: Final Product—Capsules-Capsules Co-pack (2) (Liquid Filled Hard or Soft Gelatin/Hard Gelatin/HPMC capsules)—Formulation/Manufacturing Process (at local CMO, controlled room and humidity conditions throughout the process):

| Ingredients | Amount (%) |
| --- | --- |
| Uncoated Coated (EC) Symbiotic Granules/Pellets | 1% |
| Vegetable oil (immiscible liquid) | 8.5% |
| Gelatin as powder and Hard Gelatin Capsules | 0.5% |
| Uncoated Dextrose Monohydrate Granules/Pellets | 76% |
| Excipients (Microcrystalline cellulose-filler, Silicon dioxide-glidant/flow aid) | 6% |
| Hard Gelatin/HPMC Capsules | 6% |
| "Polymers" (pH 7.2 to 7.5 sensitive coating) | 2% |
| Water/Solvents as required | 0% |

The above Uncoated Symbiotic Granules/Pellets intermediate formulation is blended in desired portions with Vegetable oil (immiscible liquid) in a blender. Filled into capsules using soft or hard gelatin encapsulating equipment. The filled capsules are enteric coated using aqueous or solvent coating solution of Polymers" (pH 7.2 to 7.5 sensitive coating) in coating pan or fluid bed coating equipment using optimized conditions.

The above Uncoated Dextrose Monohydrate Granules/Pellets is blended in desired portion with excipients in V-type or similar. The blender is filled into capsules using encapsulating equipment. The filled capsules are further coated with pH 7.2 to 7.5 sensitive coating using aqueous or solvent coating solution of "Polymers" in a coating pan or fluid bed drier/coater with optimized conditions.

Example: Final Product—Tablets/Microtablets—Formulation/Manufacturing Process (at local CMO, controlled room and humidity conditions throughout the process):

| Ingredients | Amount (%) |
|---|---|
| Uncoated Symbiotic Granules/Pellets | 1% |
| Uncoated Dextrose Monohydrate Granules/Pellets | 81% |
| Excipients (Microcrystalline cellulose-filler, polyvinylpyrrolidone, pregelatinized starch-disintegrant and silicon dioxide-flow aid, magnesium stearate-lubricant) | 13% |
| HPMC or equivalent "polymers" (Barrier coat) | 1% |
| "Polymers" (pH 7.2 to 7.5 sensitive coating) | 4% |
| Water/Solvents as required | 0% |

The above Uncoated Symbiotic and Dextrose Monohydrate Granules/Pellets intermediate formulations are blended in desired portions in V-type or similar blender with to aid in flow, disintegration and lubrication (for tableting machine). The blended powders are compressed into Tablets/Microtablets using tableting equipment. The tablets are further barrier coated in a coating pan or fluid bed dryer using aqueous or solvent coating solution of HPMC or equivalent "polymers" (Barrier coat). The barrier coated tablets are further enteric coated using aqueous or solvent coating solution of Polymers" (pH 7.2 to 7.5 sensitive coating) in coating pan or fluid bed coating equipment using optimized conditions.

Example: Final Product—Orally disintegrating Tablets (ODT)—Formulation/Manufacturing Process (at local CMO, controlled room and humidity conditions throughout the process):

| Ingredients | Amount (%) |
|---|---|
| pH 7.2 to 7.5 Enteric Coated (EC) Symbiotic Granules/Pellets | 1% |
| pH 7.2 to 7.5 Enteric Coated (EC) Dextrose Monohydrate Granules/Pellets | 85% |
| Excipients (Microcrystalline cellulose-filler, pregelatinized starch-disintegrant and silicon dioxide-flow aid, magnesium stearate-lubricant) | 14% |

The pH 7.2 to 7.5 Enteric Coated (EC) Symbiotic and Dextrose Monohydrate Granules/Pellets intermediate formulation are blended in desired portions in V-type or similar blender with additional excipients to aid in flow. The blended powders are compressed into soft tablets using tableting equipment.

Example: Final Product—Tablets Co-pack (2) (Hard Gelatin/HPMC capsules)—Formulation/Manufacturing Process (at local CMO, controlled room and humidity conditions throughout the process):

| Ingredients | Amount (%) |
|---|---|
| Uncoated Symbiotic Granules/Pellets | 1% |
| Uncoated Dextrose Monohydrate Granules/Pellets | 81% |
| Excipients (Microcrystalline cellulose - filler, Silicon dioxide - glidant/flow aid) | 14% |
| HPMC or equivalent "polymers" (Barrier coat) | 1% |
| "Polymers" (pH 7.2 to 7.5 sensitive coating) | 4% |
| Water/Solvents as required | 0% |

The above Uncoated Symbiotic Granules/Pellets intermediate formulation is blended in desired portions in V-type or similar blender with excipients. The blended powders are compressed into Tablets/Microtablets using tableting equipment. The tablets are further barrier coated in a coating pan or fluid bed dryer using aqueous or solvent coating solution of HPMC or equivalent "polymers" (Barrier coat). The barrier coated tablets are further enteric coated using aqueous or solvent coating solution of Polymers" (pH 7.2 to 7.5 sensitive coating) in coating pan or fluid bed coating equipment using optimized conditions. The above Uncoated Dextrose Monohydrate Granules/Pellets intermediate formulation is blended in desired portions in V-type or similar blender with excipients. The blended powders are compressed into Tablets/Microtablets using tableting equipment. The tablets are further barrier coated in a coating pan or fluid bed dryer using aqueous or solvent coating solution of HPMC or equivalent "polymers" (Barrier coat). The barrier coated tablets are further enteric coated using aqueous or solvent coating solution of Polymers" (pH 7.2 to 7.5 sensitive coating) in coating pan or fluid bed coating equipment using optimized conditions. The two tablet products are co-packed.

Final Product Packaging (at local CMO, dry low humidity and low oxygen (N2 purging) conditions throughout the process). The above granules are packaged in sachet, and the coated tablets, as well as capsules are packaged into bottles with induction sealing or blistered (co-packs) at low humidity (at or below 40% RH) and controlled room temperature conditions (at 20 to 25 degrees C.).

Quality Control Release Testing (Active Pharmaceutical Ingredient (API) and Final Drug Product)

Symbiotic—

| Test | Methods and Assessment |
|---|---|
| Description | Granules, pellets, tablets, capsules in blisters or bottles or sachets |
| Appearance | Visual inspection for color, shape, etc. |
| Identification | Genes, species, strains. Morphological appearance via Microscopic evaluation and/or multiplex PCR as well as other tests including biochemical methods such as fermentation profile or genotypic methods, e.g. ribotyping, restriction fragment length polymorphism (RFLP), or both. In addition, develop a specific identity assay for critical biological activity. Others test may include: DNA-DNA hybridization to specify strains in species; DNA sequence coding per WHO; Strain typing include Pulsed Field Gel electrophoresis (PFGE), etc. |
| Potency - Viable organisms | Microscopic testing, or Opacity to measure viable cells per unit or dose, i.e. colony forming units (CFU) |
| Potency Assay | Assessment of CFU (on solid medium) and tests to correlating with activity. M-viability plating. |

| Test | Methods and Assessment |
|---|---|
| Purity | Endotoxin content, residual antibiotics, and/or the quantification of residual toxic components or contaminants introduced during manufacture by Elisa or amino acid profile |
| Microbial bioburden or contaminants and limits | Extraneous materials including pathogens by using Elisa or amino acid profile or SDS page or ion exchange chromatography, etc. Microbial limits by US Pharmacopeia (USP 31 <61>). |
| Percent viable cells | Micro testing after regrown in appropriate media and tests, e.g., Dead/live assay by ATP. Also determination of non-viable units per g i.e., by electro-zone count of non-fluorescent cells (SDS PAGE) |
| Particulate matter | USP 31 <788> |
| Pyrogens | Rabbit pyrogencity test (USP 31 <151>) |
| pH Testing | pH meter |
| Residual moisture | Water content, USP 31 <921> |
| Content Uniformity | ATP |
| Package Integrity | Leaker test by vacuum |
| Stability | Potency, viable cell determination, microbial contamination, pH an residual moisture |
| In-vitro release testing (via dissolution testing equipment):USP paddle or basket | Medium: pH 1 buffer (simulated gastric), pH 6 buffer, pH 7.2 to 7.5 buffer (simulated intestinal fluid), followed by pH 5.5-6.2 buffer (simulated colonic fluid). Sample Times: pH 1 buffer - 1 hour pH 6 buffer - 1 hour pH 7.2 to 7.5 - 1, 2, 3 and 4 hours pH 7.2 to 7.5- 1, 2, 4 and 8 hours Symbiotic Assay: Microbiology testing for count (cfu/gram) for Symbiotic: |
| Stability testing (0, 6, 12, 18 and 24 months): | Identification, Potency, viable cell determination, microbial contamination, pH and residual moisture, etc. |

Example 3

Example 3 is directed toward the making and testing of a formulation according to the invention for the treatment of a Gastro intestinal reflux disease (GERD).

GERD is a chronic symptom of mucosal damage caused by stomach acid coming up from the stomach into the esophagus. GERD is usually caused by changes in the barrier between the stomach and the esophagus, including abnormal relaxation of the lower esophageal sphincter, which normally holds the top of the stomach closed, impaired expulsion of gastric reflux from the esophagus, or a hiatal hernia. These changes may be permanent or temporary.

Treatment is typically via lifestyle changes and medications such as proton pump inhibitors, H2 receptor blockers or antacids with or without alginic acid. Surgery may be an option in those who do not improve. In the Western world between 10 and 20% of the population is affected. Probiotics or Fecal Microbiota For Transplation (FMT) (subject on another patent application) may also help in balancing microbiota before and after usage of proton pump inhibitors.

Materials and Methods:

Described below are formulations that are being made and tested for the target delivery for testing in chemical and biological assays, the formulation having an proton pump inhibitor (e.g. Omeprazole magnesium, 22.4 mg equivalent to 20 mg base (range: 10-40 mg)) (millimeter range) for release at pH 7.2-7.5 in ileum and symbiotic (prebiotic: L-Leucine; probiotic: species of: *Lactobacillus* and *Bifidobacterium*) to FMT for release at pH 5.5-6.2 in right colon every 24 hours.

Active Pharmaceutical Ingredient (API): Proton pump inhibitor—For example, omeprazole supplied by local generic US/non-US suppliers, e.g., Manus Aktteva, etc. Prebiotics—proteins (casein, hydrolyzed protein, etc.), peptides, amino acids (L-Leucine), carbohydrates glucose, lactose, starches, inulin, etc. and certain bacterial strains: provided by Denisco, CHR Hansen, Institu Risell-Lallemand and other high quality global suppliers of prebiotics. Live probiotics Species of: *Lactobacillus* and *Bifidobacterium* provided by Denisco, CHR Hansen, Institu Risell-Lallemand and other high quality global suppliers or FMT from volunteers.

Inactive Ingredients (Excipients): Microcrystalline, starch, HPMC or equivalent "polymers", hard gelatin capsules, and other fillers, etc.—purchased from local US supplier such as FMC, Capsugel, Colorcon, as well as polyvinylpyrrolidone—binder, pregelatinized starch—disintegrant, silicon dioxide—flow aid, magnesium stearate—lubricant) from various reputable excipient suppliers.

Intermediate Formulation/Manufacturing Process (at local CMO): "Uncoated Proton pump inhibitor Granules/Pellets" (100 micron range):

| Ingredients | Amount (%) |
|---|---|
| Proton pump inhibitor | 13% |
| Excipients (Microcrystalline cellulose - filler, polyvinylpyrrolidone - binder, pregelatinized starch - disintegrant, silicon dioxide - flow aid, magnesium stearate - lubricant) | 87% |
| Water as required | 0% |

Prepare a dry granulation with proton pump inhibitor and excipients in a low or high shear mixer and/or perform wet granulations with water/solvent and further pelletize using extruder/spheronizer and then drying to remove excess water/solvent using optimized conditions.

"pH 7.2 to 7.5 Enteric Coated (EC) Proton pump inhibitor Granules/Pellets" (100 micron range):

| Ingredients | Amount (%) |
|---|---|
| Uncoated Proton pump inhibitor Granules/Pellets | 88% |
| HPMC or equivalent "polymers" (Barrier and Seal coats) | 2% |
| "Polymers" (pH 7.2 to 7.5 sensitive coating) | 10% |
| Water/Solvents as required | 0% |

The Uncoated Proton pump inhibitor Granules/Pellets are coated (the barrier coat) with aqueous or solvent coating solution of HPMC or equivalent "polymers" to coat in a coating pan or fluid bed drier/coater using optimized conditions. The barrier coated micropellets or granules are further coated with aqueous or solvent coating solution of pH 7.2 to 7.5, sensitive coating "Polymers" in a coating pan or fluid bed drier/coater using optimized conditions. The above pH 7.2 to 7.5, sensitive coated micropellets or granules are seal coated with aqueous or solvent coating solution of HPMC or equivalent "polymers" in a coating pan or fluid bed drier/coater using optimized conditions.

"Uncoated Symbiotic Granules/Pellets" (100 micron range):

| Ingredients | Amount (%) |
| --- | --- |
| L. Leucine (prebiotic) | 5% |
| Freeze dried bacteria (appropriate species and strains of lactobacillus and bifidobacterium probiotic) | 3% |
| Excipients (Microcrystalline cellulose - filler, polyvinyl-pyrrolidone - binder, pregelatinized starch - disintegrant, silicon dioxide - flow aid, magnesium stearate - lubricant) | 92% |

Prepare a dry blend with prebiotic, freeze dried bacteria and excipients in a low or high shear mixer.

"pH 5.5 to 6.2 Enteric Coated (EC) Symbiotic Granules/Pellets" (100 micron).

| Ingredients | Amount (%) |
| --- | --- |
| Uncoated Symbiotic Granules/Pellets | 88% |
| HPMC or equivalent "polymers" (Barrier and Seal coats) | 2% |
| "Polymers" (pH 5.5 to 6.2 sensitive coating) | 10% |
| Water/Solvents as required | 0% |

The Uncoated Symbiotic Granules/Pellets are coated (barrier coat) with aqueous or solvent coating solution of HPMC or equivalent "polymers" in a coating pan or fluid bed drier/coater using optimized conditions. The above barrier coated micropellets or granules are further coated with aqueous or solvent coating solution of "Polymers" (pH 5.5 to 6.2 sensitive coating) in a coating pan or fluid bed drier/coater using optimized conditions. The above pH 5.5 to 6.2 coated micropellets or granules are seal coated with aqueous or solvent coating solution of HPMC or equivalent "polymers" in a coating pan or fluid bed drier/coater using optimized conditions.

"pH 5.5 to 6.2/7.2 to 7.5 Enteric Coated (EC) Symbiotic Granules/Pellets" (100 micron).

| Ingredients | Amount (%) |
| --- | --- |
| pH 5.5 to 6.2 Enteric Coated (EC) Symbiotic Granules/Pellets | 88% |
| HPMC or equivalent "polymers" (Barrier and seal coats) | 2% |
| "Polymers" (pH 7.2 to 7.5 sensitive coating) | 10% |
| Water/Solvents as required | 0% |

The above pH 5.5 to 6.2 Enteric Coated (EC) Symbiotic Granules/Pellets are coated with aqueous or solvent coating solution of "Polymers" (pH 7.2 to 7.5 sensitive coating) in a coating pan or fluid bed drier/coater using optimized conditions. The above micropellets or granules are further coated with aqueous or solvent coating solution of HPMC or equivalent "polymers" (seal coat) in a coating pan or fluid bed drier/coater using optimized conditions.

Example: Final Product—Sachet—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Mannitol - filler, Silicon dioxide - glidant/flow aid) | 55% |

The above pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions in V-type or similar blender with excipients using optimized conditions. The blended powders are filled into sachets using powder filling equipment.

Example: Final Product—Powder for Reconstitution—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Mannitol - filler, Silicon dioxide - glidant/flow aid) | 55% |
| Diluent | 100 mL |

The above pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions in V-type or similar blender with excipients using optimized conditions. The blended powders are filled into bottles (induction sealed) or pouches (sealed) using powder filling equipment.

Example: Final Product—Fast Dispersible Tablets—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Mannitol - filler, Silicon dioxide - glidant/flow aid) | 55% |
| Diluent | 100 mL |

The above pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions in V-type or similar blender with excipients using optimized conditions. The blended powders are compressed to produce small tablets with scoring for ease of dosing for pediatric applications.

Example: Final Product—Capsules (Hard gelatin/HPMC)—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Microcrystalline cellulose - filler, Silicon dioxide - glidant/flow aid) | 45% |
| Hard Gelatin/HPMC Capsules | 10% |

The above pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions in V-type or similar blender with excipients. The blended powders are filled into capsules using encapsulating equipment.

Example: Final Product—Capsules (Liquid Filled Hard or Soft Gelatin)—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Vegetable oil (immiscible liquid) and other ingredients (paste) | 50% |
| Gelatin as powder and Hard Gelatin Capsules | 5% |

The above pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions with immiscible liquid in a blender. Filled into capsules using soft or hard gelatin encapsulating equipment using optimized conditions.

Example: Final Product—Capsule-in-Capsule (Hard gelatin) (1)—Formulation/Manufacturing Process (at local CMO, controlled room temperature, humidity and oxygen conditions throughout the process):

| Ingredients | Amount (%) |
| --- | --- |
| pH 5.5 to 6.2/7.2 to 7.5 Enteric Coated (EC) Symbiotic Granules/Pellets | 15% |
| pH 7.2 to 7.5 Enteric Coated (EC Proton pump inhibitor Granules/Pellets | 30% |
| Excipients (Microcrystalline cellulose - filler, Silicon dioxide - glidant/flow aid) | 47% |
| Small and Large Hard Gelatin/HPMC Capsules | 8% |

The pH 5.5 to 6.2/7.2 to 7.5 Enteric Coated (EC) Symbiotic Granules/Pellets is blended in with portion of excipients in V-type or similar blender and the blend. The blend is filled into smaller capsules using encapsulating equipment and optimized conditions. The above pH 7.2 to 7.5 Enteric Coated (EC) Proton pump inhibitor Granules/Pellets are blended together in desired portions in V-type or similar blender with excipients. The blended intermediate formulations along with the smaller filled capsules are further filled into larger capsules using specialized capsule filling equipment and optimized conditions.

Example: Final Product—Capsule-in-Capsule (Hard gelatin) (2)—Formulation/Manufacturing Process (at local CMO, controlled room temperature, humidity and oxygen conditions throughout the process):

| Ingredients | Amount (%) |
| --- | --- |
| pH 5.5 to 6.2 Enteric Coated (EC) Symbiotic Granules/Pellets | 15% |
| "Polymers" (pH 7.2 to 7.5 sensitive coating) | 10% |
| Excipients (Microcrystalline cellulose - filler, Silicon dioxide - glidant/flow aid) | 37% |
| pH 7.2 to 7.5 Enteric Coated (EC) Proton pump inhibitor Granules/Pellets | 30% |
| Small and Large Hard Gelatin/HPMC Capsules | 8% |
| Water/Solvents as required | 0% |

The pH 5.5 to 6.2 Enteric Coated (EC) Symbiotic Granules/Pellets is blended in desired portions in V-type or similar blender with excipients. The blend is filled into smaller capsules using encapsulating equipment. The smaller filled capsules are further coated with pH 7.2 to 7.5 sensitive coating using aqueous or solvent coating solution of "Polymers" in a coating pan or fluid bed drier/coater with optimized conditions. The above pH 7.2 to 7.5 Enteric Coated (EC) Proton pump inhibitor Granules/Pellets are blended in desired portions in V-type or similar blender with excipients. The smaller pH 7.2 to 7.5 coated capsules and the blends are further filled into larger capsules using specialized capsule filling equipment and optimized conditions.

Example: Final Product—Capsule-in-Capsule (Hard gelatin) (3)—Formulation/Manufacturing Process (at local CMO, controlled room temperature, humidity and oxygen conditions throughout the process):

| Ingredients | Amount (%) |
| --- | --- |
| pH 5.5 to 6.2/7.2 to 7.5 Enteric Coated (EC) Symbiotic Granules/Pellets | 15% |
| Uncoated Proton pump inhibitor Granules/Pellets Excipients (Microcrystalline cellulose - filler, Silicon dioxide - glidant/flow aid) | 25% 40% |
| "Polymers" (pH 7.2 to 7.5 sensitive coating) | 10% |
| Small and Large Hard Gelatin/HPMC Capsules | 10% |

The above uncoated Proton pump inhibitor Granules/Pellets and a portion of excipients are blended together in V-type or similar blender. The blend is filled into smaller capsules using encapsulating equipment and optimized conditions. The smaller filled capsules are further coated with pH 7.2 to 7.5 sensitive coating using aqueous or solvent coating solution of "Polymers" in a coating pan or fluid bed drier/coater with optimized conditions. The pH 5.5 to 6.2/7.2 to 7.5 Enteric Coated (EC) Symbiotic Granules/Pellets is blended in with portion of excipients in V-type or similar blender. The blended intermediate formulations along with the smaller pH 7.2 to 7.5 EC capsules are further filled into larger capsules using specialized capsule filling equipment and optimized conditions.

Example: Final Product—Capsule-in-Capsule (Hard gelatin) (4)—Formulation/Manufacturing Process (at local CMO, controlled room temperature, humidity and oxygen conditions throughout the process):

| Ingredients | Amount (%) |
| --- | --- |
| Uncoated Symbiotic Granules/Pellets | 12% |
| Uncoated Proton pump inhibitor Granules/Pellets Excipients (Microcrystalline cellulose - filler, Silicon dioxide - glidant/flow aid) | 30% 30% |
| "Polymers" (pH 5.6 to 6.2 sensitive coating) | 10% |

| Ingredients | Amount (%) |
|---|---|
| "Polymers" (pH 7.2 to 7.5 sensitive coating) | 10% |
| Small and Large Hard Gelatin/HPMC Capsules | 8% |

The Uncoated Symbiotic Granules/Pellets is blended in with portion of excipients in V-type or similar blender. The blend is filled into smaller capsules using encapsulating equipment and optimized conditions. The smaller filled capsules are further coated with pH 5.6 to 6.2 sensitive coating using aqueous or solvent coating solution of "Polymers" in a coating pan or fluid bed drier/coater with optimized conditions. The above uncoated Proton pump inhibitor Granules/Pellets are blended together in desired portions in V-type or similar blender with excipients. The blended intermediate formulations along with the smaller pH 5.6 to 6.2 EC capsules are further filled into larger capsules using specialized capsule filling equipment and optimized conditions. The larger capsules are further coated with pH 7.2 to 7.5 sensitive coating using aqueous or solvent coating solution of "Polymers" in a coating pan or fluid bed drier/coater with optimized conditions.

Example: Final Product—Orally disintegrating Tablets (ODT)—Formulation/Manufacturing Process (at local CMO, controlled room temperature, humidity and oxygen conditions throughout the process):

| Ingredients | Amount (%) |
|---|---|
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Mannitol - filler, polyvinylpyrrolidone - binder, pregelatinized starch - disintegrant and silicon dioxide - flow aid, magnesium stearate - lubricant) | 55% |

The Uncoated Proton pump inhibitor Granules/Pellets, pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets s are blended in desired portions in V-type or similar blender with excipients. The blended powders are compressed into soft tablets using tableting equipment.

Example: Final Product—Tablets/Microtablets—Formulation/Manufacturing Process (at local CMO, controlled room temperature, humidity and oxygen conditions throughout the process):

| Ingredients | Amount (%) |
|---|---|
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Microcrystalline cellulose - filler, polyvinylpyrrolidone -binder, pregelatinized starch - disintegrant and silicon dioxide - flow aid, magnesium stearate - lubricant) | 53% |
| HPMC or equivalent "polymers" (Film coat) | 2% |
| Water/Solvents as required | 0% |

The pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions in V-type or similar blender with excipients to aid in flow, disintegration and lubrication (for tableting machine). The blended powders are compressed into Tablets/Microtablets using tableting equipment. The tablets are further film coated using aqueous or solvent coating solution in a coating pan or fluid bed dryer using HPMC or equivalent "polymers" (Film coat).

Final Product—Tablet (2)—Formulation/Manufacturing Process (at local CMO, controlled room temperature, humidity and oxygen conditions throughout the process):

| Ingredients | Amount (%) |
|---|---|
| Uncoated Proton pump inhibitor Granules/Pellets | 30% |
| pH 5.5 to 6.2 Enteric Coated (EC) Symbiotic Granules/Pellets | 15% |
| Excipients (Microcrystalline cellulose - filler, polyvinylpyrrolidone - binder, pregelatinized starch - disintegrant and silicon dioxide - flow aid, magnesium stearate - lubricant) | 43% |
| "Polymers" (pH 7.2 to 7.5 sensitive coating) | 10% |
| HPMC or equivalent "polymers" (Film coat) | 2% |
| Water/Solvents as needed | 0% |

The above Uncoated Proton pump inhibitor Granules/Pellets and pH 5.5 to 6.2 Enteric Coated (EC) Symbiotic Granules/Pellets is blended in desired portions in V-type or similar blender with excipients to aid in flow, disintegration and lubrication (for tableting machine). The blended powders are compressed into tablets using tableting equipment. The compressed tablets are coated with pH 7.2 to 7.5 sensitive coating using aqueous or solvent coating solution of "Polymers" in a coating pan or fluid bed drier/coater with optimized conditions ("EC tablets"). The tablets are further film coated using aqueous or solvent coating solution in a coating pan or fluid bed dryer using HPMC or equivalent "polymers" (Film coat).

Example: Final Product—Tablet-in-Tablet (1)—Formulation/Manufacturing Process (at local CMO, controlled room temperature, humidity and oxygen conditions throughout the process):

| Ingredients | Amount (%) |
|---|---|
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Microcrystalline cellulose - filler, polyvinylpyrrolidone - binder, pregelatinized starch - disintegrant and silicon dioxide - flow aid, magnesium stearate - lubricant) | 53% |
| HPMC or equivalent "polymers" (Film coat) | 2% |
| Water/Solvents as required | 0% |

The pH 5.5 to 6.2/7.2 to 7.5 Enteric Coated (EC) Symbiotic Granules/Pellets is blended in desired portions in V-type or similar blender with excipients to aid in flow, disintegration and lubrication (for tableting machine). The blended powders are compressed into small tablets/Microtablets using tableting equipment. The above pH 7.2 to 7.5 Enteric Coated (EC) Proton pump inhibitor Granules/Pellets are blended in desired portions in V-type or similar blender with excipients to aid in flow, disintegration and lubrication (for tableting machine). The blended powder is compress coated over the small tablets/Microtablets using compress coat tableting machine. The tablets are further film coated using aqueous or solvent coating solution in a coating pan or fluid bed dryer using HPMC or equivalent "polymers" (Film coat).

Final Product—Tablet-in-Tablet (2)—Formulation/Manufacturing Process (at local CMO, controlled room temperature, humidity and oxygen conditions throughout the process):

| Ingredients | Amount (%) |
| --- | --- |
| Uncoated Proton pump inhibitor Granules/Pellets | 25% |
| pH 5.5 to 6.2 Enteric Coated (EC) Symbiotic Granules/Pellets | 15% |
| Excipients (Microcrystalline cellulose - filler, polyvinylpyrrolidone -binder, pregelatinized starch - disintegrant and silicon dioxide - flow aid, magnesium stearate - lubricant) | 48% |
| "Polymers" (pH 7.2 to 7.5 sensitive coating) | 10% |
| HPMC or equivalent "polymers" (Film coat) | 2% |
| Water/Solvents as needed | 0% |

The above Uncoated Proton pump inhibitor Granules/Pellets is blended in desired portions in V-type or similar blender with additional excipients to aid in flow, disintegration and lubrication (for tableting machine). The blended powders are compressed into small tablets/Microtablets using tableting equipment. The pH 5.5 to 6.2 Enteric Coated (EC) Symbiotic Granules/Pellets is blended in desired portions in V-type or similar blender with excipients to aid in flow, disintegration and lubrication (for tableting machine). The blended EC Symbiotic Granules/Pellets are compress coated over the small EC tablets/Microtablets using compress coat tableting machine. The compressed tablets are coated with pH 7.2 to 7.5 sensitive coating using aqueous or solvent coating solution of "Polymers" in a coating pan or fluid bed drier/coater with optimized conditions ("EC tablets"). The tablets are further film coated using aqueous or solvent coating solution in a coating pan or fluid bed dryer using HPMC or equivalent "polymers" (Film coat).

Example: Final Product—Tablet-in-Capsule (Hard gelatin) (1)—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Microcrystalline cellulose - filler, polyvinylpyrrolidone - binder, pregelatinized starch - disintegrant and silicon dioxide - flow aid, magnesium stearate - lubricant) | 45% |
| Hard Gelatin/HPMC Capsules | 10% |

The pH 7.2 to 7.5 Enteric Coated (EC) Proton pump inhibitor Granules/Pellets and pH 5.5 to 6.2/7.2 to 7.5 Enteric Coated (EC) Symbiotic Granules/Pellets are blended in desired portions in V-type or similar blender with excipients to aid in flow, disintegration and lubrication (for tableting machine). The blended powders are compressed into Tablets/Microtablets using tableting equipment. The excipients and the compressed tablets filled into hard gelatin capsules using specialized encapsulating equipment.

Example: Final Product—Tablet-in-Capsule (Hard gelatin) (2)—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2/7.2 to 7.5 Enteric Coated (EC) Symbiotic Granules/Pellets | 15% |
| Excipients (Microcrystalline cellulose - filler, polyvinylpyrrolidone - binder, pregelatinized starch - disintegrant and silicon dioxide - flow aid, magnesium stearate - lubricant) | 45% |
| Hard Gelatin /HPMC Capsules | 10% |

The pH 5.5 to 6.2/7.2 to 7.5 Enteric Coated (EC) Symbiotic Granules/Pellets are blended in desired portions in V-type or similar blender with excipients to aid in flow, disintegration and lubrication (for tableting machine). The blended powders are compressed into small tablets/Microtablets using tableting equipment. The above pH 7.2 to 7.5 Enteric Coated (EC) Proton pump inhibitor Granules/Pellets are blended in desired portions in V-type or similar blender with additional excipients to aid in flow, disintegration and lubrication (for tableting machine). The blended powder and compressed tablets are filled into large Hard Gelatin Capsules using encapsulating equipment.

Example: Final Product—Tablet-in-Capsule (Hard gelatin) (3)—Formulation/Manufacturing Process (at local CMO, controlled room temperature, humidity and oxygen conditions throughout the process):

| Ingredients | Amount (%) |
| --- | --- |
| pH 7.2 to 7.5 Enteric Coated (EC) Proton pump inhibitor Granules/Pellets | 30% |
| pH 5.5 to 6.2 Enteric Coated (EC) Symbiotic Granules/Pellets | 15% |
| Excipients (Microcrystalline cellulose - filler, polyvinylpyrrolidone - binder, pregelatinized starch - disintegrant and silicon dioxide - flow aid, magnesium stearate - lubricant) | 35% |
| "Polymers" (pH 7.2 to 7.5 sensitive coating) | 10% |
| Hard Gelatin/HPMC Capsules | 10% |
| Water/Solvents as required | 0% |

The pH 5.5 to 6.2 Enteric Coated (EC) Symbiotic Granules/Pellets are blended in desired portions in V-type or similar blender with excipients to aid in flow, disintegration and lubrication (for tableting machine). The blended powders are compressed into small tablets/Microtablets using tableting equipment. The compressed tablets are coated with pH 7.2 to 7.5 sensitive coating using aqueous or solvent coating solution of "Polymers" in a coating pan or fluid bed drier/coater with optimized conditions ("EC tablets"). The above pH 7.2 to 7.5 Enteric Coated (EC) Proton pump inhibitor Granules/Pellets are blended in desired portions in V-type or similar blender with excipients to aid in flow, disintegration and lubrication (for tableting machine). The blended powder and the EC tablets are filled into a larger capsule using encapsulating equipment.

Example: Final Product—Tablet-in-Capsule (Hard gelatin) (4)—Formulation/Manufacturing Process (at local CMO, controlled room temperature, humidity and oxygen conditions throughout the process):

| Ingredients | Amount (%) |
| --- | --- |
| Uncoated Proton pump inhibitor Granules/Pellets | 25% |
| pH 5.5 to 6.2/7.2 To 7.5 Enteric Coated (EC) Symbiotic Granules/Pellets | 15% |

-continued

| Ingredients | Amount (%) |
|---|---|
| Excipients (Microcrystalline cellulose - filler, polyvinylpyrrolidone - binder, pregelatinized starch - disintegrant and silicon dioxide - flow aid, magnesium stearate - lubricant) | 40% |
| "Polymers" (pH 7.2 to 7.5 sensitive coating) | 10% |
| Hard Gelatin/HPMC Capsules | 10% |
| Water/Solvents as required | 0% |

The above Uncoated Proton pump inhibitor Granules/Pellets formulation is blended in desired portions in V-type or similar blender with excipients to aid in flow, disintegration and lubrication (for tableting machine). The blended powders are compressed into small tablets/Microtablets using tableting equipment. The compressed tablets are coated with pH 7.2 to 7.5 sensitive coating using aqueous or solvent coating solution of "Polymers" in a coating pan or fluid bed drier/coater with optimized conditions ("EC tablets"). The pH 5.5 to 6.2 Enteric Coated (EC) Symbiotic Granules/Pellets are blended in desired portions in V-type or similar blender with excipients to aid in flow, disintegration and lubrication (for tableting machine). The blended powder and the small EC tablets are filled into a larger capsule using encapsulating equipment.

Final Product—Tablet-in-Capsule Hard Gelatin (5)—Formulation/Manufacturing Process (at local CMO, controlled room temperature, humidity and oxygen conditions throughout the process):

| Ingredients | Amount (%) |
|---|---|
| Uncoated Proton pump inhibitor Granules/Pellets | 25% |
| pH 5.5 to 6.2 Enteric Coated (EC) Symbiotic Granules/Pellets | 15% |
| Excipients (Microcrystalline cellulose - filler, polyvinylpyrrolidone - binder, pregelatinized starch - disintegrant and silicon dioxide - flow aid, magnesium stearate - lubricant) | 38% |
| "Polymers" (pH 7.2 to 7.5 sensitive coating) | 10% |
| Hard Gelatin/HPMC Capsules | 10% |
| HPMC or equivalent "polymers" (Film coat) | 2% |
| Water/Solvents as needed | 0% |

The above Uncoated Proton pump inhibitor Granules/Pellets is blended in desired portions in V-type or similar blender with additional excipients to aid in flow, disintegration and lubrication (for tableting machine). The blended powders are compressed into small tablets/Microtablets using tableting equipment. The pH 5.5 to 6.2 Enteric Coated (EC) Symbiotic Granules/Pellets is blended in desired portions in V-type or similar blender with excipients to aid in flow, disintegration and lubrication (for tableting machine). The blended EC Symbiotic Granules/Pellets along with the proton pump inhibitor small compressed tablets are filled into larger capsules using encapsulating machine. The large capsules are coated with pH 7.2 to 7.5 sensitive coating using aqueous or solvent coating solution of "Polymers" in a coating pan or fluid bed drier/coater with optimized conditions ("EC tablets"). The capsules are further film coated using aqueous or solvent coating solution in a coating pan or fluid bed dryer using HPMC or equivalent "polymers" (Film coat).

Example: Final Product—Bi-Layer Tablets—Formulation/Manufacturing Process (at local CMO, controlled room temperature, humidity and oxygen conditions throughout the process):

| Ingredients | Amount (%) |
|---|---|
| pH 7.2 to 7.5 Enteric Coated (EC) Proton pump inhibitor Granules/Pellets | 30% |
| Excipients (Microcrystalline cellulose - filler, polyvinylpyrrolidone - binder, pregelatinized starch - disintegrant and silicon dioxide - flow aid, magnesium stearate - lubricant) | 53% |
| pH 5.5 to 6.2/7.2 to 7.5 Enteric Coated (EC) Symbiotic Granules/Pellets | 15% |
| HPMC or equivalent "polymers" (Film coat) | 2% |
| Water/Solvents as required | 0% |

The above pH 7.2 to 7.5 Enteric Coated (EC) Proton pump inhibitor Granules/Pellets are blended in desired portions in V-type or similar blender with excipients to aid in flow, disintegration and lubrication (for tableting machine). The blended powders are compressed into tablets using bi-layer tableting equipment ("EC Tablets"). The pH 5.5 to 6.2/7.2 to 7.5 Enteric Coated (EC) Symbiotic Granules/Pellets are blended in desired portions in V-type or similar blender with excipients to aid in flow, disintegration and lubrication (for tableting machine). The blended powder is compressed over the EC tablets using bilayer tableting machine. The tablets are further film coated using aqueous or solvent coating solution in a coating pan or fluid bed dryer using HPMC or equivalent "polymers" (Film coat).

Final Product Packaging (at local CMO, dry low humidity and low oxygen (N2 purging) conditions throughout the process):

The above granules are packaged in sachet, and the coated tablets, capsules are packaged into bottles with induction sealing or blistered at low humidity (at or below 40% RH) and controlled room temperature conditions (at 20 to 25 degrees C.).

Quality Control Release Testing (Active Pharmaceutical Ingredient (API) and Final Drug Product) Symbiotic.

| Test | Methods and Assessment |
|---|---|
| Description | Granules, pellets, tablets, capsules in blisters or bottles or sachets |
| Appearance | Visual inspection for color, shape, etc. |
| Identification | Genes, species, strains. Morphological appearance via Microscopic evaluation and /or multiplex PCR as well as other tests including biochemical methods such as fermentation profile or genotypic methods, e.g. ribotyping, restriction fragment length polymorphism (RFLP), or both. In addition, develop a specific identity assay for critical biological activity. Others test may include: DNA-DNA hybridization to specify strains in species; DNA sequence coding per WHO; Strain typing include Pulsed Field Gel electrophoresis (PFGE), etc. |
| Potency - Viable organisms | Microscopic testing, or Opacity to measure viable cells per unit or dose, i.e. colony forming units (CFU) |
| Potency Assay | Assessment of CFU (on solid medium) and tests to correlating with activity. M-viability plating. |
| Purity | Endotoxin content, antibiotic residue and/or the quantification of residual toxic components or contaminants introduced during manufacture by Elisa or amino acid profile |
| Microbial bioburden or contaminants and limits (related substances) | Extraneous materials including pathogens by using Elisa or amino acid profile or SDS page or ion exchange chromatography, etc. Microbial limits by US Pharmacopeia (USP 31 <61>). |
| Percent viable cells | Micro testing after regrown in appropriate media and test, e.g., Dead/live assay by ATP. Also determination of non-viable units per g i.e., by electro-zone count of non-fluorescent cells (SDS PAGE) |

-continued

| Test | Methods and Assessment |
|---|---|
| Particulate matter | USP 31 <788> |
| Pyrogens | TBD |
| pH Testing | pH meter |
| Residual moisture | Water content, USP 31 <921> |
| Content Uniformity | ATP |
| Live/Dead Assay | ATP |
| Heavy metals | Inductively Coupled Plasma-Atomic Emission Spectrophotometry (ICP-AES); Inductively Coupled Plasma-Mass Spectroscopy (ICP-MS); Atomic Emission Spectrophotometry (AES); or Atomic Absorption Spectrophotometry (AAS). |
| Water content | Karl Fischer |
| Package Integrity | Leaker test by vacuum |
| Stability | Potency, viable cell determination, microbial contamination, pH an residual moisture |

Proton Pump Inhibitor(s)

| Test | Methods and Assessment |
|---|---|
| Identification | HPLC and other |
| Assay | HPLC and other |
| Impurities and Related sub | HPLC and other |
| Content uniformity | HPLC and other |
| Microbial limits | US Pharmacopeia (USP 31 <61>). |

Symbiotic and Proton Pump Inhibitor

| Test | Methods and Assessment |
|---|---|
| In-vitro release testing (via dissolution testing equipment): | USP paddle or basket<br>Medium: pH 1 buffer (simulated gastric), pH 6 buffer, pH 7.2 to 7.5 buffer (simulated intestinal fluid), followed by pH 5.5 - buffer (simulated colonic fluid).<br>Sample Times:<br>pH 1 buffer - 1 hour<br>pH 6 buffer - 1 hour<br>pH 7.2 to 7.5 - 1, 2, 3 and 4 hours<br>pH 5.5 to 6.2 - 1, 2, 4 and 8 hours<br>Symbiotic Assay:<br>Microbiology testing for count (cfu/gram) for<br>Proton pump inhibitor Assay:<br>HPLC |
| Stability testing (0, 6, 12, 18 and 24 months): | Symbiotic:<br>Identification, Appearance, Potency, viable cell determination, microbial contamination, pH and residual moisture, related substance, water content, Live/dead Assay, etc.<br>Proton pump inhibitor:<br>Identification, Assay, Impurities, Related Substances, microbial contamination, pH and residual moisture, IVRT, etc. |

Example 4

Oral delivery of biologic and non-biologic drugs to distal ileum and/or colon.

The pill-in-pill dosage form (e.g., tablet-in-tablet or capsule-in-capsule, etc.) would pass through the GI tract from stomach (pH 1 to 4), to duodenum (pH 5.5 to 6.2) and deliver to distal ileum (pH 7.3 to 8.0) and/or proximal colon (pH 5.5 to 6.2), depending on the design. The release from this pill-in-pill dosage form would not require any other aid (e.g. sugars, starches etc.) or external conditions or energy source such as presence or absence of enzymes or bacterial flora in the distal ileum or proximal colon. Another advantage of the pill-in-pill dosage form would be that the drug release is possible in various disease conditions (e.g. IBD, etc.) when the pH of the distal ileum and proximal colon may have significantly different from the normal values of above pH 7.4 and below pH 6.5, respectively. In order to demonstrate the concept, the tablet was initially developed and followed by the capsule-in-capsule dosage form (See Table 1 below) to deliver a small molecule or biologic directly to the proximal colon, within a 2 hour delivery target window, bypassing the stomach (2 hours) and duodenum (1 hour) and the ileum (2 hours).

TABLE 1

Capsule-in-Capsules Design

| | Inner Capsule | Outer Capsule |
|---|---|---|
| Material and Size of Capsule | Gelatin or HPMC or other, smaller size, e.g. smaller than #3, etc. Band sealed for coating (with or without seal coat) | Gelatin or HPMC or other, larger size, e.g. larger than #1, etc. Band sealed for coating (with or without seal coat) |
| API (biologic and non-biologic drugs) | Small molecules, prokaryotes cells (e.g. archaea, bacteria), eukaryote cells (e.g. fungus, plants), virus particles, proteins,, peptides, parasites, vaccine antigens, etc., or nothing | Small molecules, prokaryotes cells (e.g. archaea, bacteria), eukaryote cells (e.g. fungus, plants) virus particles, proteins, cells, peptides, parasites, vaccine antigens, etc. or nothing |
| Excipients | Prebiotics, solids, liquids, semi-solids, growth promoters | Prebiotics, solids, liquids, semi-solids, growth promoters |
| Dosage forms | Formulated tablets, soft and hard capsules, pellets, powders, etc. | Formulated tablets, soft and hard capsules, pellets, powders, etc. |
| Coatings | Reverse enteric with or without fillers | Regular enteric with or without fillers |
| Target release | At pH 6.5 (or below) within 2 hours delivery target window (goal: proximal colon delivery) | At pH 7.0 (or above) within 2 hours delivery target window (goal: distal ileum delivery) |
| Testing | Standard USP dissolution testing in various multiple media | |

The target release for drugs in dissolution media was pH 6.5 in 2 hours, representing the proximal colon and with no release at pH 1.2 (gastric) for 2 hours, pH 5.5 (duodenal) for 1 hour, pH 7.0 (ileum) for 1 hour and pH 7.4 (distal ileum) for 1 hour. Probiotic and acetaminophen were used as representative biologic agent (lyophilized bacteria) and small molecule, respectively. Acetaminophen was also used as a marker for probiotic during release testing. The small molecule and the probiotic mixes were prepared separately with and without additional excipients. Hydroxypropylmethyl cellulose (HPMC) capsules were used as the reservoir for carrying these drugs. HPMC capsules have several advantages as they are made from non-animal materials, chemically stable, have low moisture content (protect lyophilized bacteria), less brittle even at low humidity (survive the GI transit), fast dissolution, biodegradable, no crosslinking and suitable to automatic capsules filling machines. These capsules can be band sealed, which has the following advantages: avoid the need for additional steps of seal coating with polymers; avoid the need for excess moisture and heat required for processing, especially important for maintenance of the viability of the biologicals; and minimize the impact on release of drug from the capsules.

The polymers evaluated were aqueous based methacrylic acid copolymers and were designated as either reverse enteric (e.g. EUDRAGIT® EPO) or regular enteric (e.g. EUDRAGIT® FS 30D, EUDRAGIT® S100, EUDRAGIT®

L100, EUDRAGIT® L30D-55) alone or in combinations. EUDRAGIT® EPO is designed to solubilize at pH 6.5 or below and also possess good moisture barrier properties which protected lyophilized bacteria and further improved stability. EUDRAGIT® FS 30D, EUDRAGIT® S100, EUDRAGIT® L100, EUDRAGIT® L30D-55 are designed to solubilize above pH 7.0, 6.5, 6.0, 5.5, respectively. These polymers can be applied on the tablets and capsules with heat and moisture below, 30° C. and 40% RH, respectively, which is important for the maintenance of the viability of biological drugs. The tablet dosage form was initiated and then followed by the capsule-in-capsule dosage form. These capsules were subject to standard USP dissolution testing. Notably, these similar principles apply for delivery to distal ileum alone and in combination with proximal colon. Applications of this technology would broadly include the delivery of Microbiome Ecology Therapy (MET); Small molecule drugs and Vaccines, etc.

Figure 8:
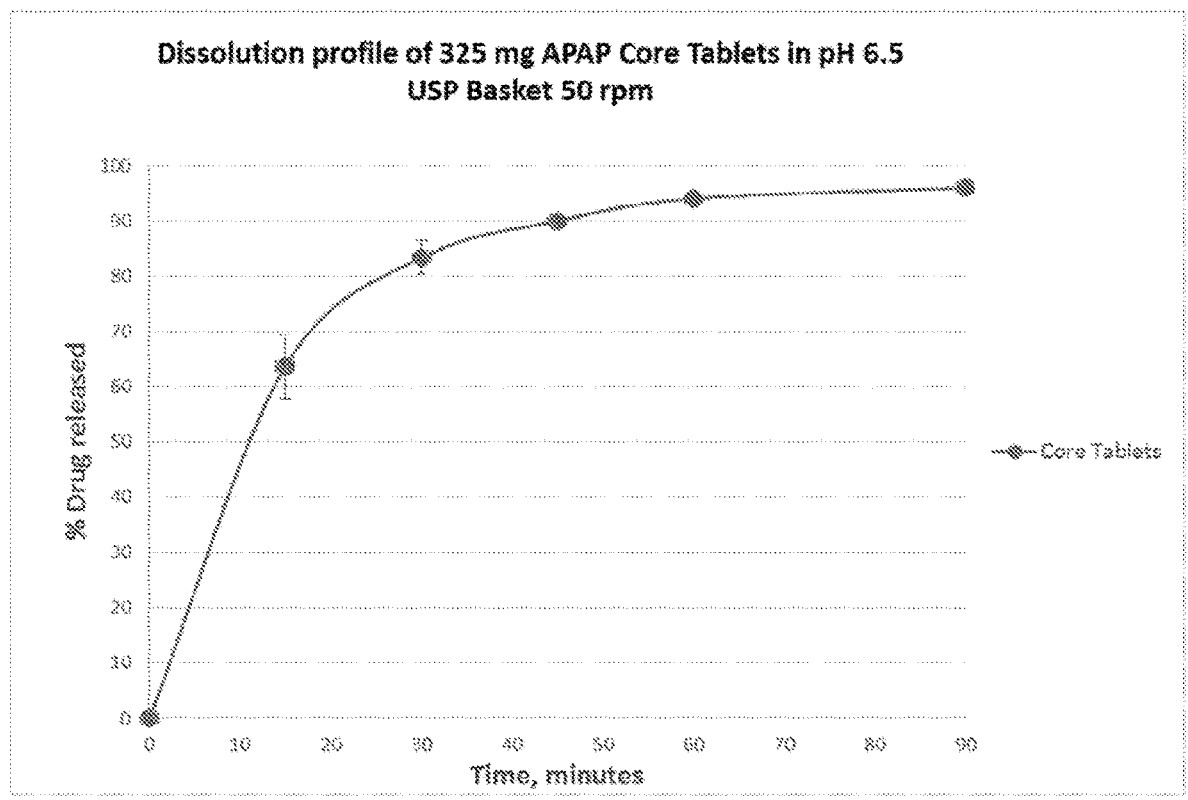
FIG. 8 shows the dissolution of Acetaminophen (APAP) 325 mg core tablets in pH 6.5 (USP dissolution apparatus: Basket at 50 rpm; n=3).
Figure 9:
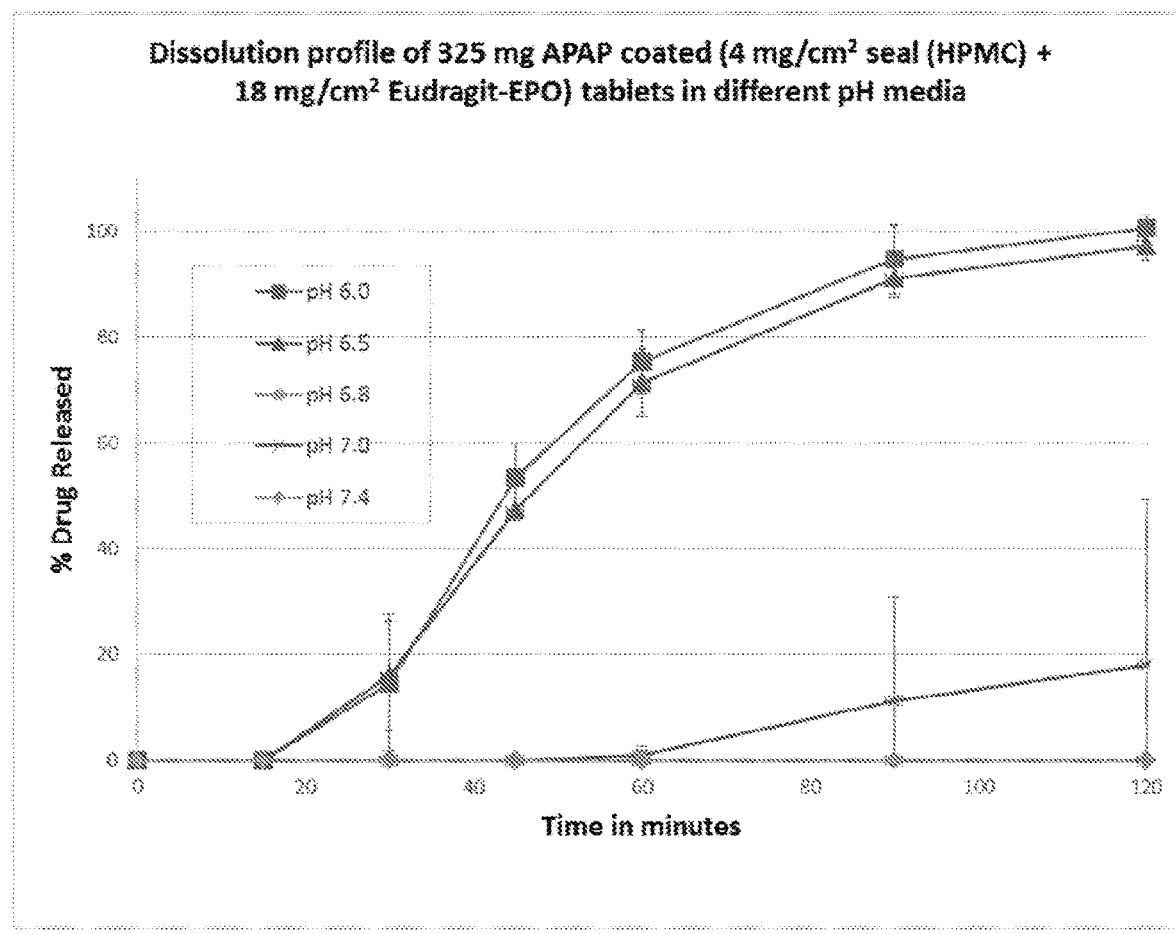
FIG. 9 shows the dissolution profile of 325 mg APAP tablets sealed with 4 mg/cm$^2$ seal (HPMC) and coated with EUDRAGIT®-EPO 18 cm$^2$) in pH 6.0, pH 6.5, pH 6.8, pH 7.0 and pH 7.4. (USP dissolution apparatus: Basket at 50 rpm; n=3).

Initial development focused on coating of the acetaminophen (APAP) core tablets using APAP as the marker for monitoring the release of biologic and non-biologic small molecule drugs from the dosage form. The 325 mg uncoated tablet cores dissolved fairly rapidly, greater than 85% in 45 minutes in USP dissolution apparatus with basket at 50 rpm in pH 6.5 phosphate buffer (Formulation 1, FIG. 8). When these APAP tablets were coated with reverse enteric material (Evonik EPO) at up to 18 mg/cm$^2$ level and performed the dissolution testing under the same conditions, 100% of the APAP was released at target pH 6.5 within 2 hours, simulating the release of the drug in the proximal colon (Formulation 2, FIG. 9). Since this coating normally was designed to dissolve below pH 6.5, the rate of release from the tablet formulation was more rapid at pH 6.0, as expected. Also as expected, no release of APAP was observed from the tablets at pH 6.8, pH 7.0 and pH 7.4.

Figure 10:
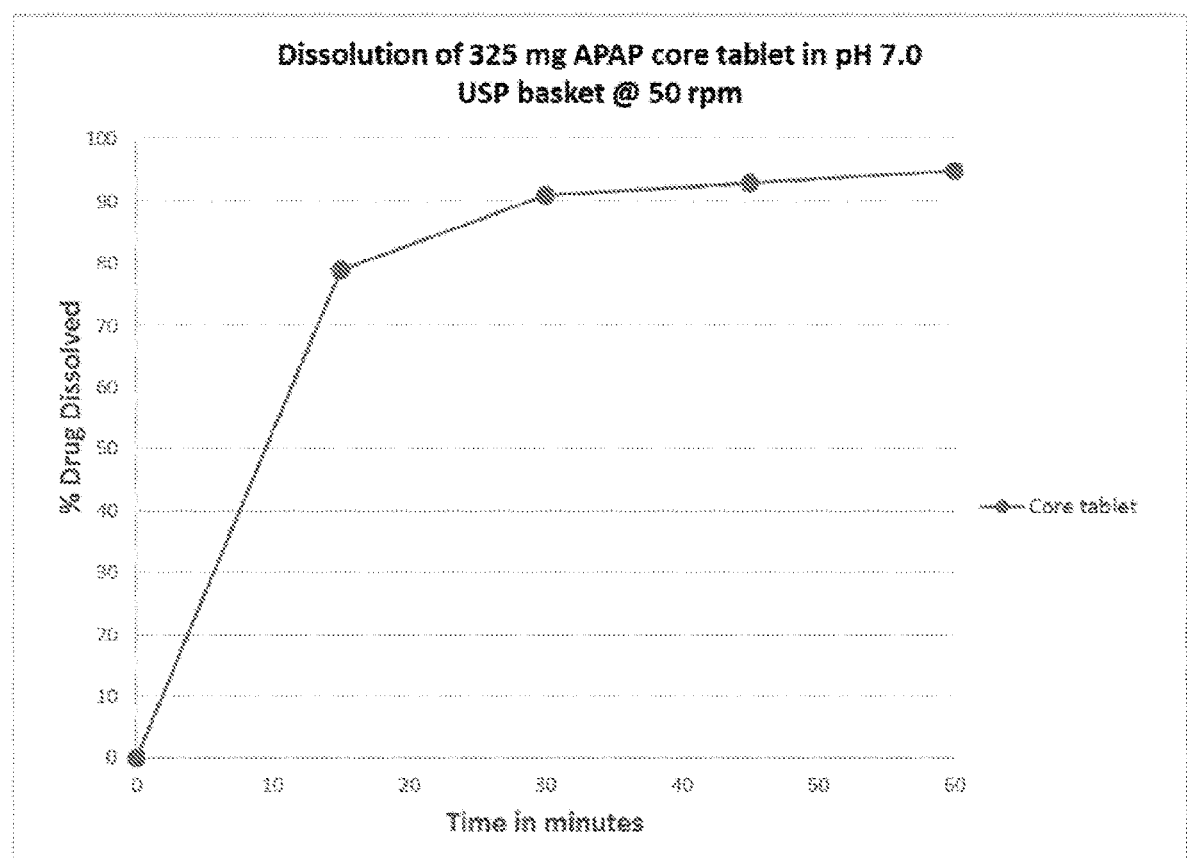
FIG. 10 shows the dissolution of 325 mg APAP core tablet in pH 7.0 (USP dissolution apparatus: Basket at 50 rpm; n=3).
Figure 11:
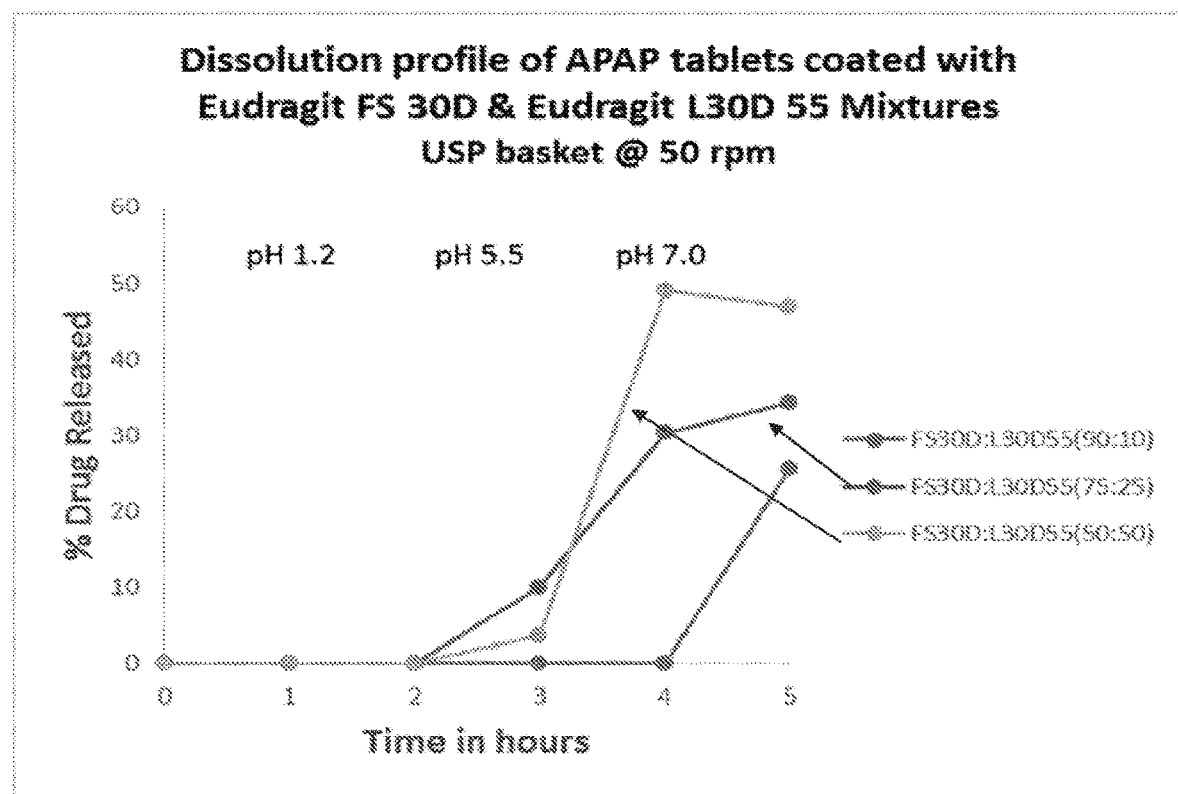
FIG. 11 shows the dissolution profile of 325 mg coated APAP tablets coated with different ratios of FS30 D & L30D55 in pH 1.2, pH 5.5 & pH 7.0. (USP dissolution apparatus: Basket at 50 rpm; n=3).

The 325 mg uncoated tablet cores dissolved fairly rapidly, greater than 85% in 45 minutes in USP dissolution apparatus with basket at 50 rpm in pH 7.0 phosphate buffer (Formulation 1, FIG. 10). These APAP tablets were coated with regular enteric material (Evonik FS30D/L30 Mixtures) at up to 15 mg/cm$^2$ level, and subject to dissolution in pH 1.2 for 2 hours, pH 5.5 for 1 hour and pH 7.0 for 2 hours using the same apparatus and speed. The formulation passed the performance test in pH 1.2 for 2 hours and 1 hour at pH 5.5. The release rate at pH 7 was slower and did not pass the 2 hour test. However, the release rate increased as expected with lower ratio of Evonik FS30D/L30, e.g. 50/50 (Formulations 3 (a-c), FIG. 11). Based on these results, it was concluded that more permeable coatings would be required to obtain the desired release profiles in pH 7.0. Additional optimization would also be required for the tablet dosage form including consideration of other formulation factors, such as coating thickness, total polymer applied, physicochemical properties of the drug, loading dose, size and shape of the tablets, etc.

As indicated earlier, the aim was to develop a capsule-in-capsule dosage form which would deliver a small molecule or a biologic to the proximal colon, within a 2 hour delivery target window, without the need for additional compression and also for ease of demonstrating the applications of colonic drug delivery technology. The principles developed here can be easily adapted to other dosage forms, such as compressed tablets, pellets, oral disintegrating tablets, liquid filled capsules, etc.

Figure 12:
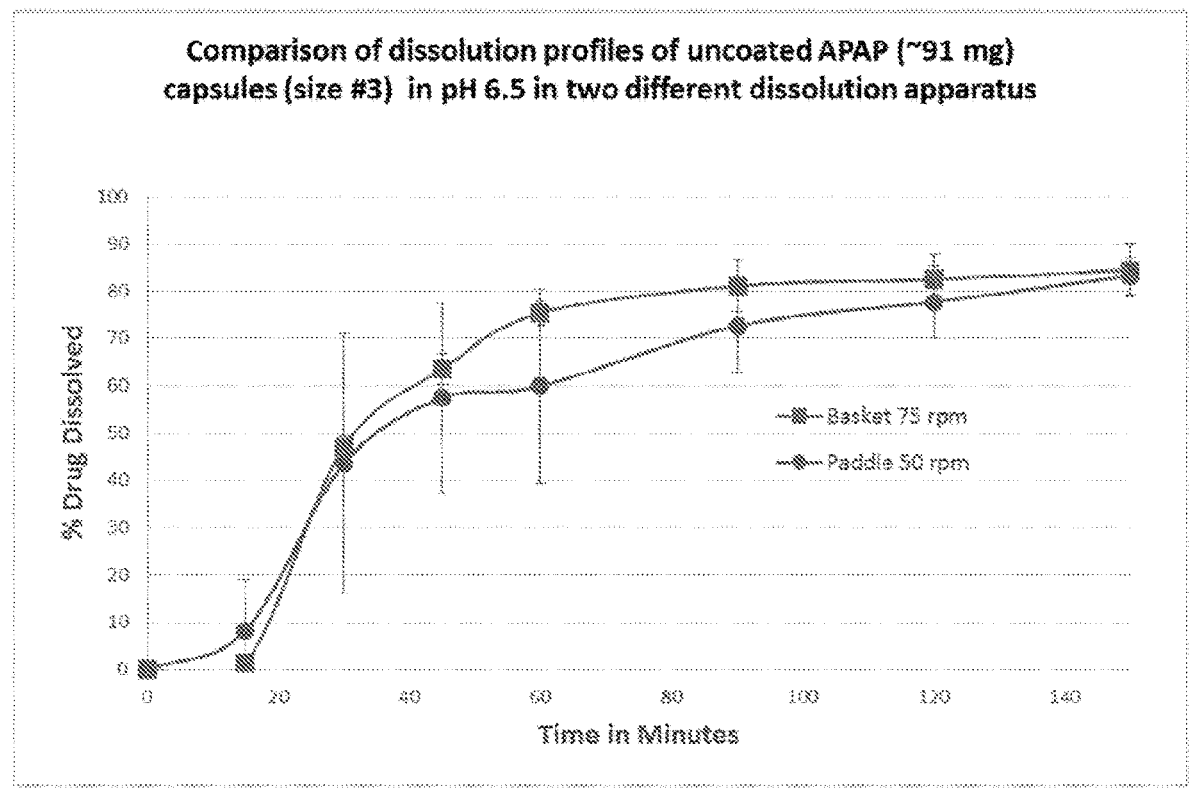
FIG. 12 shows the comparison of dissolution profiles of uncoated APAP (~91 mg) capsules (size #3) in pH 6.5 (using two USP dissolution apparatus: basket @ 75 rpm and Paddle @ 50 rpm; n=3).
Figure 13:
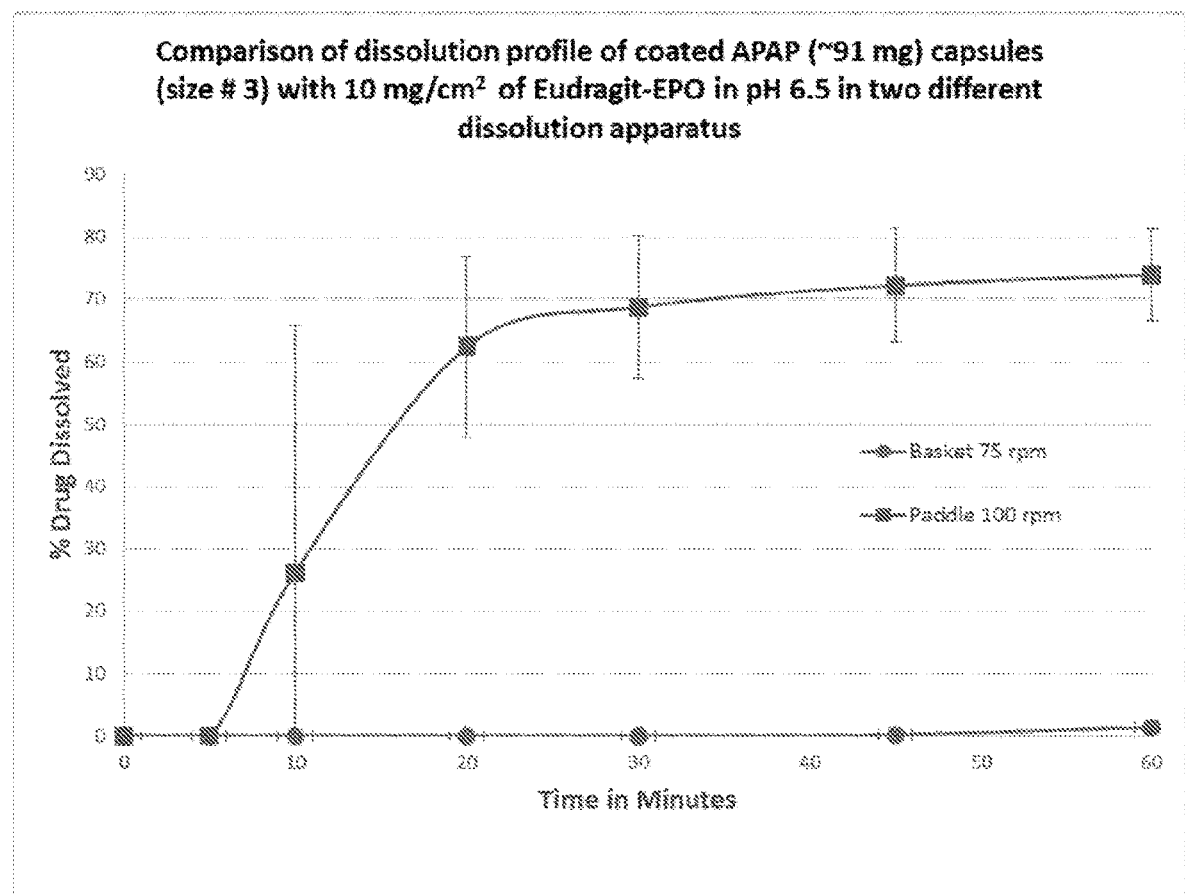
FIG. 13 shows the comparison of dissolution profiles of coated APAP (~91 mg) capsules (size #3) coated with 10 mg/cm$^2$ EUDRAGIT®-EPO in pH 6.5 (using two USP dissolution apparatus: basket @ 75 rpm and Paddle @ 50 rpm; n=3).
Figure 14:
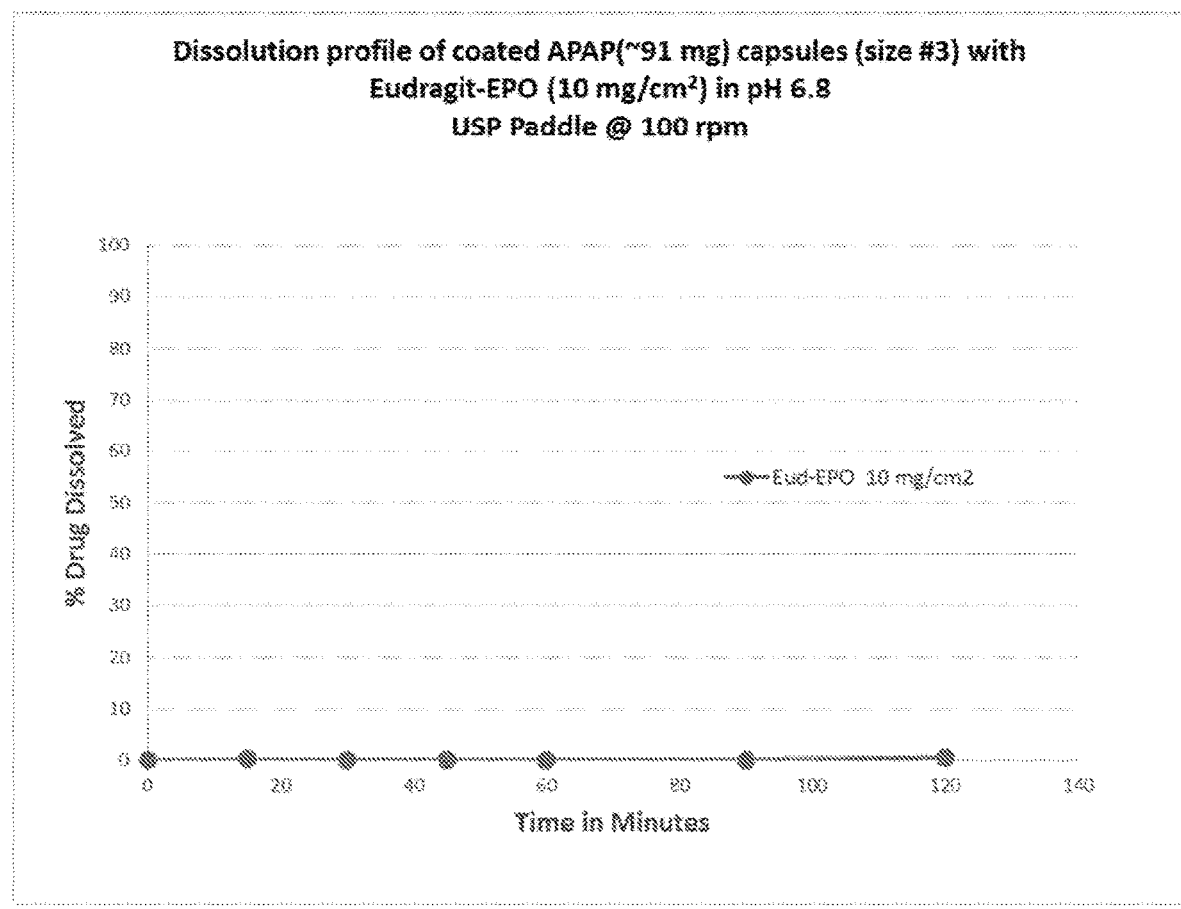
FIG. 14 shows the dissolution profile of coated APAP (~91 mg) capsules (size #3) coated with EUDRAGIT®-EPO (10 mg/cm$^2$) in pH 6.8 (USP dissolution apparatus: Paddle at 100 rpm; n=3).

The uncoated inner smaller capsule containing APAP was subjected to USP dissolution tests with basket at 75 rpm and paddle at 50 rpm in pH 6.5 dissolution media. The release from the capsules was much slower (Formulation 4, FIG. 12) as compared to the tablets and higher speeds would be required to disintegrate the capsules in the basket. However, there was almost no difference between the release profiles for the capsules either in the basket or paddle. Based on physical appearance of the capsules in the paddle method, the capsules appear to break down more easily as compared to the basket method, but were still not completely disintegrated. The smaller inner APAP capsules were coated with reverse enteric coat, EUDRAGIT® EPO at 10 mg/cm$^2$. The coated capsules were subjected to USP dissolution tests with basket at 75 rpm and paddle at 100 rpm in pH 6.5 dissolution media. The capsules met the release requirement at pH 6.5 in 2 hours when using the paddle method at 100 rpm (Formulation 5, FIG. 13). Physically all the capsules had broken down and completely disintegrated. Note there was no release from the capsules in the basket at 75 rpm and also the capsules were physically intact (not broken down or disintegrated) in the basket even after 2 hours. The coated capsules were also subject to pH 6.8 dissolution media for 2 hours at 10 mg/cm$^2$ coating level using the paddle at 100 rpm. As expected there was no release from the capsules (Formulation 5, FIG. 14). Also, physically, the capsules had not disintegrated. The paddle speed of 100 rpm for dissolution testing was justified since the release in vivo is generally associated with a significant gut agitation and compression, something that may not been seen with the in vitro dissolution test. Also, typically for enteric coated capsules, disintegration apparatus (similar to USP dissolution apparatus III) with high turbulence are typically used for evaluation of release.

Figure 15:
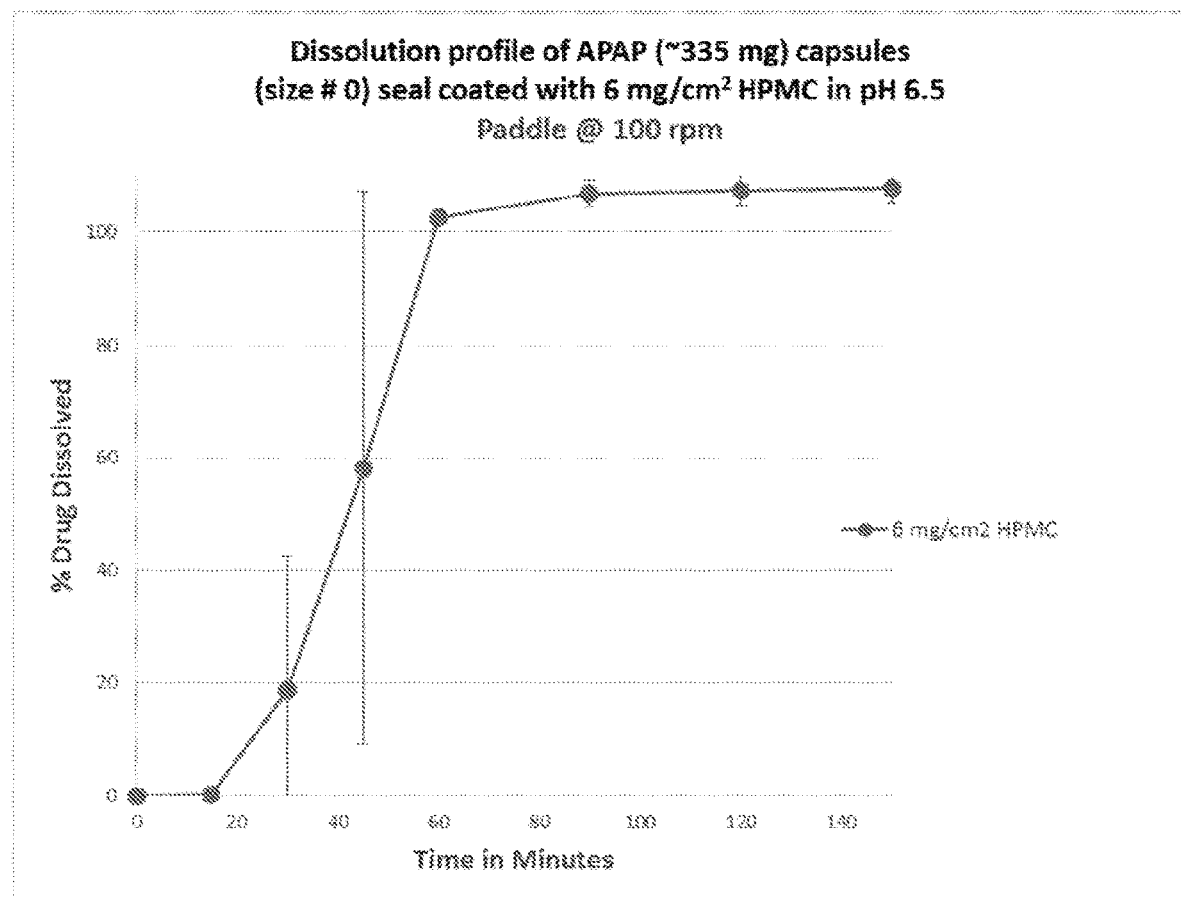
FIG. 15 shows the dissolution profile of uncoated APAP (~335 mg) capsules (size #0) sealed with 6 mg/cm$^2$ HPMC in pH 6.5 (USP dissolution apparatus: Paddle at 100 rpm; n=3).
Figure 16:
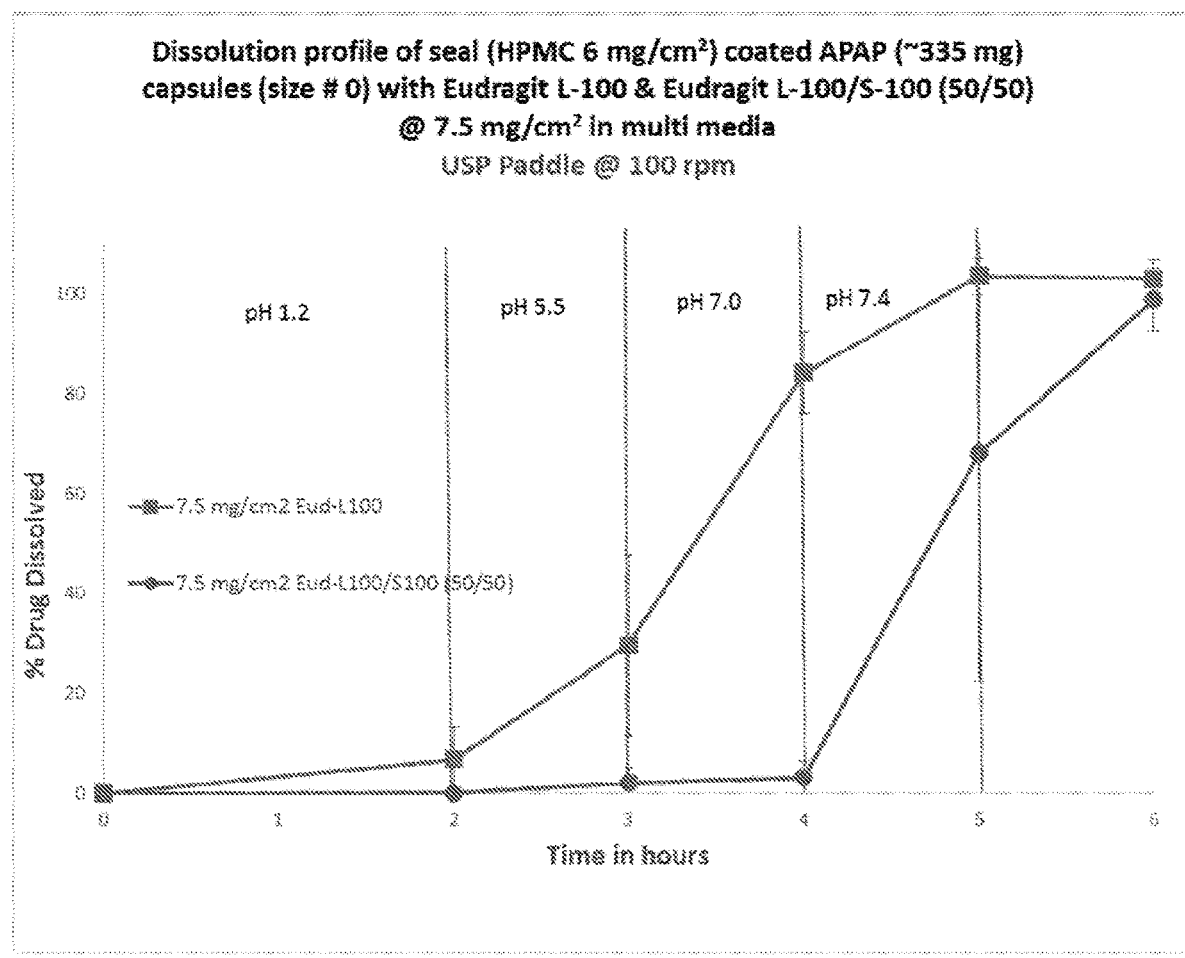
FIG. 16 shows the dissolution profile of APAP (~335 mg) capsules (size #0), sealed with HPMC-6 mg/cm2 and coated with EUDRAGIT® L100 & EUDRAGIT®-L100/S100 (50/50)—7.5 mg/cm$^2$ in multi-media (USP dissolution apparatus: Paddle at 100 rpm).
Figure 17:
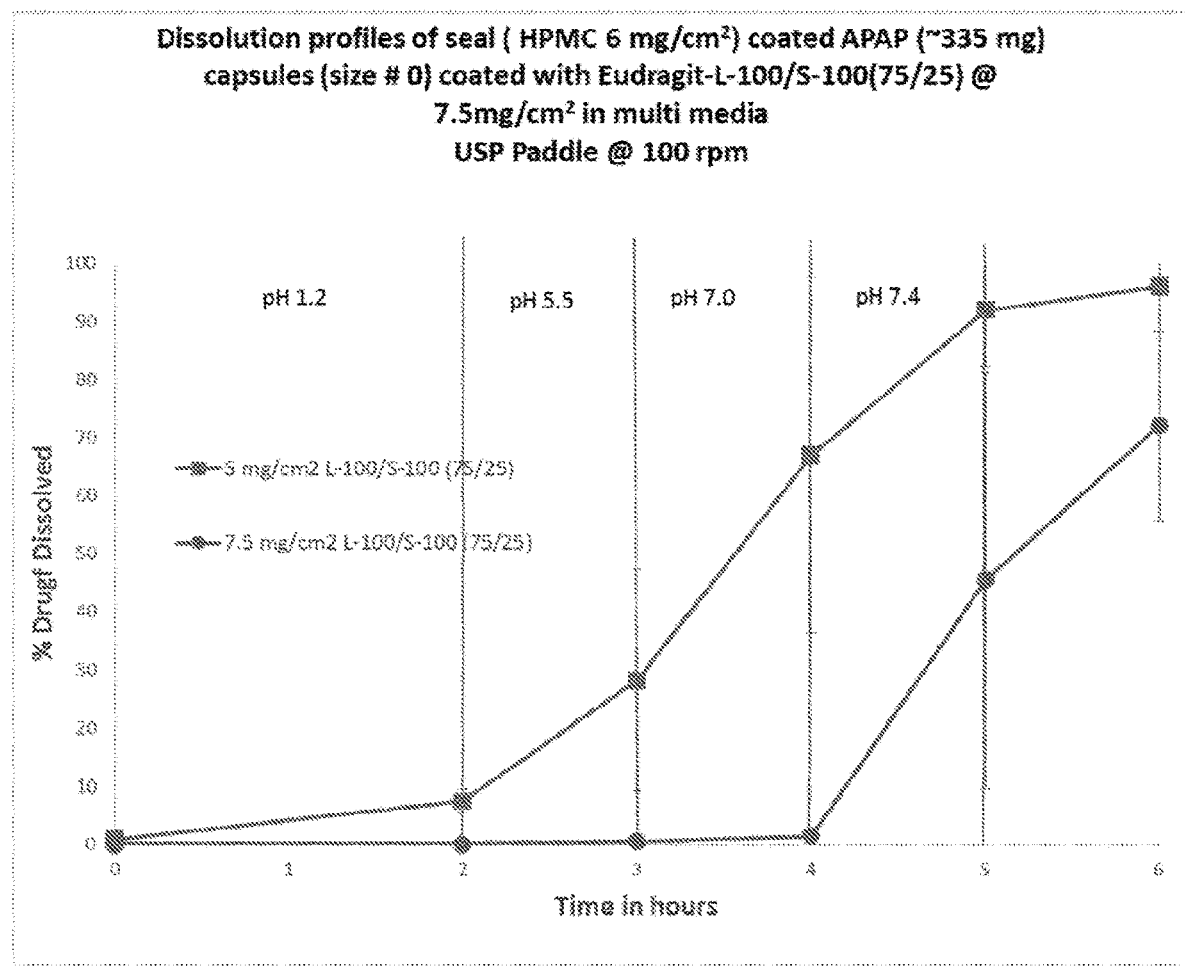
FIG. 17 shows the dissolution profile APAP (~335 mg) capsules (size #0), sealed with HPMC-6 mg/cm2) and coated with EUDRAGIT®-L100/S100 (75/25) 5 mg/cm$^2$ and 7.5 mg/cm$^2$ in multi-media. (USP dissolution apparatus: paddle at 100 rpm).

The larger outer seal coated (no enteric) capsule containing APAP was subjected to USP dissolution tests with paddle at 100 rpm in pH 6.5 dissolution media. The release from these capsules was rapid and all capsules released the drug within 1 hour (Formulation 6, FIG. 15). Also physically all capsules had disintegrated. The larger outer APAP containing capsules were coated with regular enteric coat, EUDRAGIT® L100 and L100/S100, 50/50 mix at 7.5 mg/cm$^2$. These coated capsules were subjected to USP dissolution tests with paddle at 100 rpm in pH 1.2 (2 hours), pH 5.5 (1 hour), pH 7.0 (1 hour) and pH 7.4 (1 hour) dissolution medias. The coated capsules containing L100 alone had slight release due to drug permeation at pH 5.5 in 1 hour, but otherwise acceptable. The coated capsules containing L100/S100 50/50 mix did not pass the release test at pH 7.0/7.4 in 2 hours (Formulation 7 (a-b) FIG. 16). Hence the lager outer APAP containing capsules were coated with regular enteric coat, EUDRAGIT® L100/S100, 75/25 mix at 5 and 7.5 mg/cm$^2$. These coated capsules were subjected to USP dissolution tests with paddle at 100 rpm in pH 1.2 (2 hours), pH 5.5 (1 hour), pH 7.0 (1 hour) and pH 7.4 (1 hour) dissolution medias. All the capsules passed the dissolution at pH 1.2 for 2 hours. However, the coated capsules containing 7.5 mg/cm$^2$ did not pass the release test at pH 7.0/pH 7.4 over 2 hours. The coated capsules containing 5 mg/cm$^2$ L100/S100 75/25 mix did pass the release test at all the pH conditions (Formulation 8 (a-b), FIG. 17), except for slight permeation of drug at pH 5.5. Hence, applying a slightly higher coating thickness would eliminate this problem for drug release targeted to the distal ileum.

Figure 18:
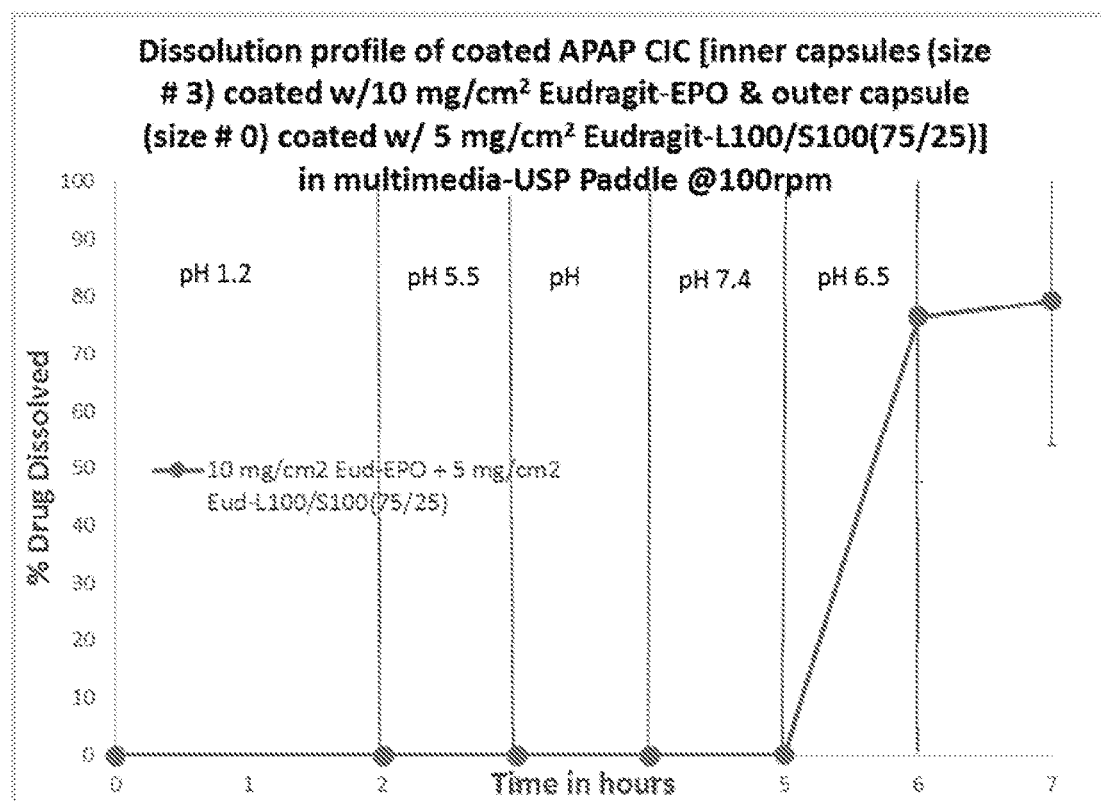
FIG. 18 shows the dissolution profile of APAP Capsule-in-capsule (CIC) [Inner capsule (size #3) band sealed and coated with 10 mg/cm$^2$ EUDRAGIT®-EPO & Outer capsule (size #0), band sealed and coated with 5 mg/cm$^2$ EUDRAGIT®-L100/S100 (75/25)] in multimedia. (USP dissolution apparatus—paddle at 100 rpm; n=6).

Based on the above results, with the goal of release in the proximal colon, the smaller capsules containing APAP, band sealed and enteric coated with EUDRAGIT® EPO 10 mg/cm$^2$ were filled into larger capsules, band sealed and further coated with EUDRAGIT® L100/S100, 75/25 mix, 5 mg/cm$^2$ on the outside. These capsule-in-capsules were subject to in-vitro USP dissolution testing, paddle at 100 rpm, for APAP release in pH 1.2 media for 2 hours, pH 5.5 for 1 hour, pH 7.0 for 1 hour, pH 7.4 for 1 hour, pH 6.5 (phosphate) for 2 hours. The results confirm full APAP release specifically at pH 6.5 within 2 hours from the inner capsule, and with no release at pH 1.2 for 2 hours, pH 5.5 for 1 hour, pH 7.0 for 1 hour and pH 7.4 for 1 hour. (Formulation 9, FIG. 18) Physically the outer capsules remained intact with no disintegration at pH 1.2 for 2 hours and pH 5.5 for 1 hour. Then the outer capsules completely disintegrated after exposure to pH 7.0 for 1 hour and pH 7.4 for 1 hour, and the inner capsule was observed and it had physically remained intact. The inner capsules then completely disintegrated when exposed to the pH 6.5 media within 2 hours. The physical observations are very consistent with the drug release data reported in FIG. 18.

Similar to the APAP capsule-in-capsules, the smaller probiotic containing capsules, were band sealed and enteric coated with EUDRAGIT® EPO 10 mg/cm$^2$ and were filled into larger capsules, band sealed and further coated with EUDRAGIT® L100/S100, 75/25 mix at 5 mg/cm$^2$ on the outside. These capsule-in-capsules were subject to USP dissolution testing, paddle at 100 rpm, for probiotic bacteria release in pH 1.2 media for 2 hours, pH 5.5 for 1 hour, pH 7.0 for 1 hour, pH 7.4 for 1 hour, pH 6.5 for 2 hours (saline phosphate buffer). Saline buffer was used to maintain isotonicity of the dissolution medium and ensure viability of the lyophilized bacteria once they are exposed to the aqueous solution. Physically, these probiotic capsules behaved exactly in the same manner as the APAP capsules. It could be surmised inferred the bacteria would be released from probiotic capsules exactly in the same manner as the APAP from the APAP capsules, i.e. full release at pH 6.5 within 2 hours from the inner capsule, and no release at pH 1.2 for 2 hours, pH 5.5 for 1 hour, pH 7.0 for 1 hour and pH 7.4 for 1 hour.

Based on SEM evaluations of reverse and regular coatings, the a preferable coating level thickness is:
First capsule (inner pill)—EUDRAGIT® EPO, 5 mg/cm$^2$-10 mg/cm$^2$:
60-180 microns (rpm) for size #3 capsule
Second capsule (outer pill)—EUDRAGIT® L100/S100 (75/25)—5 mg/cm$^2$-10 mg/cm$^2$
60-180 microns (μm) for size #0 capsule The uncoated and coated CIC capsules were analyzed to determine the level of degradation due to processing. The data suggested, and shown in Table 2, that the total strain count as measured by total CFU per capsules did not change significantly. Hence the process of handling, banding and coating applications, storage and shipment did not have any significant effect on viability of the 3 bacteria strains tested in the formulations, including the aerobic strains of *S. thermophilus* and *L. acidophilus* and anaerobic strains of *B. longum*

Materials and Methods
Acetaminophen (APAP):
(Receiving #RCA31252; Guardian Drugs) Malinckrondt Inc.-lot #784513B054-3% PVP granulated powder for tableting.
Aacetaminophen (Paracetamol, USP-APC-150)-ALP Co. (China)-Lot #0908302.
Acetaminophen (APAP) 325 mg core tablets (Lot #L0577-215-Guardian Drugs, NJ)
Probiotic Capsule: Azodyl (size #3) (Batch #023042-20; Lot #5241113; Kibow Biotech; Newtown Square, Pa. 19073)

HPMC Capsules:
Qualicaps Size #3/S-LOK-Lot #E1305982-Clear VAA (cap & body)
Qualicaps Size #3/S-LOK-Lot #E1205667-Op. White XAK (cap & body)
Qualicaps Size #3/S-LOK-Lot #E1106719-Op. Brown 15 XJX (cap & body)
Qualicaps Size #0/S-LOK-Lot #E1101410-Op. White XAK (cap & body)
Qualicaps Size #0/S-LOK-Lot #E1106476-Op. Brown 15 XJX (cap & body)
Methacrylic Acid Co-Polymers for Coating:
EPO-Ready Mix-Evonik-lot #H131181012
EUDRAGIT®-L30D 55-Evonik-Lot #B130514207
EUDRAGIT®-FS 30D Evonik-Lot #B130365004
EUDRAGIT®-S100-Evonik-Lot #B100405198
EUDRAGIT®-L100-Evonik-Lot #B120603009
Plasacryl T20-Evonik-Lot #PT130705
Coating Polymers:
HPMC E5-Dow-Lot #YG040124L1
Plasticizers:
Triethyl Citrate (TEC)-Vertellus-Lot 3 132530
Surfactants:
Polyethylene Glycol 4000-AlfaAesar-Lot #10167045
Polysorbate 80(Tween 80)-BASF-Lot #3158092
Other Excipients:
Talc-Brenntag-Lot #410052-43
Microcrystalling cellulose (MCC)-MC-102-Blanver-Lot3 135002006
Lactose Monohydrate (Supertab 11SD)-DFE Pharma-Lot #10677724
Pre-gelatinized Starch-DFE Pharma-Lot #-10601223
Crospovidone-QJNI Co.-Btch #20130115
DiCalcium Phosphate-Innophos-Lot #0701047
Coloidal silicon dioxide (Aerosil-200)-Evonik-Btch #1012082200
Silicon dioxide (Aerosil R972)-Degussa-Lot #3158092923
Magnesium Stearate-FACI Asia-Batch #MGSP0216
Magnesium Stearate-Mallinkrodt-Lot #-071226.
Hydroxy-propyl Methyl Cellulose-Shinogi-Lot #90936C
Chemicals:
Ammonium Hydroxide-AlfaAesar-Lot #E302012
Ethyl Alcohol-Fischer-Lot #M02539
Potassium Dihydrogen Phosphate-Alfa Aesar-Lot #1013774
Sodium Hydroxide-Macron Chemicals-Batch 98 #0000039706
Method for Prepare Core Tablets and Compression
The required amount as shown in the formula A of APAP, MCC, Pre-Gelatinized Starch, Crospovidone & Colloidal Silicon di-oxide was passed thru #20 sieve and was loaded in a suitable belnder and mixed for 25 minutes. At the end of the process the Magnesium stearate was added and blend was mixed for additional 5 minutes. At the end of the process the material was unloaded into clean poly-lined containers. The blend (100 kg) was compressed on a Korsch XL-100 10 station press. A modified-oval shaped, standard concave tooling (16.5 mm×7.5 mm) having plain surfaces (no logo) on both sides was used. This was design was chosen based on providing suitable substrate for functional coating. Tablets were compressed to a target weight of 600 mg (containing 325 mg APAP) with Friability of NMT 1% and Hardness of >24 kP. The tablet weight, thickness, hardness and friability was monitored as in-process test throughout the batch manufacturing. Tablet samples were taken to ensure disintegration time was <5 min.

Encapsulation and Banding

Encapsulation of Formulation B:

All the ingredients were passed thru a MMC Co-mill to ensure no agglomerates were present in the blend. A 8 Qt V-Blender was used to mix all the ingredients except Magnesium stearate. After mixing all the ingredients Magnesium stearate was added. The blend was mixed for 2 additional minutes before discharge into a double-poly lined container. The index K120i (S/N 0963-27) was set-up to run the capsules (size #3) from Qualicaps. The capsule polisher (Model TG-20) and weight scales (Mettler Toledo Scale) were set-up appropriately for the run. The processing room temperature and humidity log was documented for the run. In-process weight samples were collected during the run to ensure the target weight is achieved. The capsules were polished and collected in a double-lined poly-bags in container.

Encapsulation of Formulation D:

A FastLock K200F with vibration table was used for filling the size #0 capsules from formulation D. Size #0 Quali V capsules were used to fill the 3% granulated APAP powder. Approximate 100 capsules were filled each time. The weights for capsules were recorded.

Banding of Capsules:

Banding of capsules was performed on the IMA Bander (BD 1723) Typically banding of capsules results in a weight gain of 1-1.5 mg which is within the weight variation of the capsules so it is typically considered a part of the capsule weights and the associated variations.

Preparation of Spraying Dispersions

Preparation of EUDRAGIT®-EPO ready mix:

The Ready mix is a standard coating system from Evonik which has 51% EPO polymer. About 150 g of this dry mix is added to about 850 g of water to give approximately 1 kg of spray suspension. The material is mixed using a high shear mixer for approx. 30 minutes. The entire suspension is then passed through a 0.5 mm sieve. The suspension is next ready for spraying to the substrate using typical standard processing parameters.

Preparation of L-30D 55:

For 1 kg of spray suspension approx. 570 g of EUDRAGIT® L30D 55 dispersion is added in a larger mixer vessel. Approx. 145.5 g of Plasacryl HTP20 (anti-tacking/plasticizer system) is added to the mix. The suspension is diluted with required amount of water to get 1 kg of spray dispersion. The PlasAcryl need to be shaken before transfer to any vessel. The entire suspension is stirred for 10 minutes using a propeller stirrer.

The entire suspension is passed through a 0.5 mm sieve. The suspension is next ready for spraying to the substrate using typical standard processing parameters.

Preparation of FS 30 D:

For 1 kg of spray suspension approx. 606.1 g of EUDRAGIT® FS30D dispersion is added in a larger mixer vessel. Approx. 90.9 g of Plasacryl HTP20 (anti-tacking/plasticizer system) is added to the mix. The suspension is diluted with required amount of water to get 1 kg of spray dispersion. The PlasAcryl need to be shaken before transfer to any vessel. The entire suspension is stirred for 10 minutes using a propeller stirrer. The entire suspension is passed through a 0.5 mm sieve. The suspension is next ready for spraying to the substrate using typical standard processing parameters.

Preparation of L100 Dispersion:

For 1 kg of spray suspension approx. 99.5 g of EUDRAGIT® L100 was added into ⅔rd of the water and stir for approximately 5 minutes and making sure the powder is all wetted. Add 1N $NH_3$ (56 g) slowly into the EUDRAGIT® suspension and stir for approximately 60 minutes. Add 49.8 g of Triethyl citrate (TEC) and stir for additional 60 minutes. Separately, homogenize 49.8 g of Talc with the remaining amount (⅓ rd) of water for 10 minutes using a high shear mixer. Pour the talc suspension into the EUDRAGIT® dispersion while stirring with a conventional stirrer. The entire suspension is passed through a 0.5 mm sieve. The suspension is next ready for spraying to the substrate using typical standard processing parameters.

Preparation of S100 dispersion:

For 1 kg of spray suspension approximately 99.4 g of EUDRAGIT® S100 is added into ⅔ rd of the water and stirred for approximately 5 minutes and making sure the powder is all wetted. Add 1N $NH_3$ (67.5 g) slowly into the EUDRAGIT® suspension and stir for approximately 60 minutes. Add 49.7 g of Triethyl citrate (TEC) and stir for additional 60 minutes. Separately, homogenize 49.7 g of Talc with the remaining amount (⅓ rd) of water for 10 minutes using a high shear mixer. Pour the talc suspension into the EUDRAGIT® dispersion while stirring with a conventional stirrer. The entire suspension is passed through a 0.5 mm sieve. The suspension is next ready for spraying to the substrate using typical standard processing parameters.

For mixtures of two components prepare them separately and then add as per the desired ratios.

Coating of the Tablets and Capsules

All coatings of tablets and capsules were performed on the Thomas Engineering Accela Cota Compu-Lab-24-190. The formulations were coated in a 12" pan with two baffles. A minimum batch size of 400 g was used for the coatings. For some formulations a larger batch size of 700-1500 g was processed. A single Schlick gun (970/7-1 75S) with a nozzle size from 0.8-1.2 mm depending on the batch size and the flow rate of the suspension was used. The processing conditions were varied depending on the batch size and the coating material used. For each type of coating specific processing conditions were followed. For the safety of the product, the product temperature was always maintained below 30° C.

The general processing parameters used broadly is as follows:

Inlet air temp: 30-40° C.
Exhaust Temperature—25-30° C.
Product Temperature: 24-29° C.
Inlet air flow: 100-300 CFM
Pump speeds: 2.5-20 rpm
Atomization air pressure: 10-30 psi
ID of the tubing used: 3.2 mm,
Pan speed: 4-15 rpm.

Dissolutions testing:

Disintegration apparatus, dissolution apparatus, baskets, paddles and speeds, temperature and dissolution media, Assay, HPLC, CFU for probiotics, sampling scheme. The inner capsules were subject to dissolution testing at pH 6.5 or pH 6.8 phosphate buffers for up to 2 hours. The outer capsules were subject to dissolution media at pH 1.2 for 2 hours, pH 5.5 for 1 hour, pH 7.0 for 1 hour and pH 7.4 for 1 hour. The combined capsules were subject to dissolution media at pH 1.2 for 2 hours, pH 5.5 for 1 hour, pH 7.0 for 1 hour, pH 7.4 for 1 hour, pH 6.5 for 2 hours (with saline as isotonic agent for probiotic.

Analysis of Probiotic Capsules Before and after Coating

The contents of capsules were aseptically transferred into a sterile bottle. The two capsule contents were dissolved in saline. A sample was drawn for enumeration and incubated at 37° C. After 3 days of incubation at 37° C. (aerobically for *S. thermophilus* and *L. acidophilus*, anaerobically for *B. longum*) the colonies were counted in triplicate.

TABLE 2

Strain count (CFUs in billions), pre and post coating of capsules

| Strains | Average (range) Strain Count (CFU in billions), n = 3 | |
|---|---|---|
| | Uncoated capsules | Coated capsules |
| *S. thermophiles*\* | 13.5 (12.5-15.5) | 14.2 (13.5-14.5) |
| *L. acidophilus*\* | 2.6 (2.2-3.3) | 1.8 (1.25-2.1) |
| *B. longum*\*\* | 2.6 (2.0-3.1) | 1.9 (1.65-2.15) |
| Total Count | 18.7 | 17.9 |

\*Aerobic
\*\*Anaerbic

Formulations:
Formulation 1: 325 mg APAP tablets Core

| Ingredients | Amount mg | % |
|---|---|---|
| Acetaminophen (APAP)-3% PVP granulated form for tableting | 335 | 56 |
| Microcrystalline Cellulose, USP | 225 | 37 |
| Pre-gelatinized Starch | 18 | 3 |
| Crosspovidone | 18 | 3 |
| Colloidal silicon dioxide | 3 | <1 |
| Magnesium stearate | 1 | <1 |
| Total | 600 | 100 |

Formulation 2: APAP tablets 325 mg—sealed with 4 mg/cm$^2$ seal (HPMC) coated with EUDRAGIT® EPO 18 cm$^2$

| Ingredients | Amount mg | % |
|---|---|---|
| Core Tablet: | | |
| Acetaminophen 325 mg tablet (Formulation 1) above | 606 | 78 |
| 4% w/w Seal Coating: | | |
| HPMC E5 | 20 | 3 |
| PEG 6000, USP | 3 | <1 |
| Water, qs (removed from formulation) | — | — |
| Functional coating (18 mg/cm$^2$): | | |
| EUDRAGIT® EPO Readymix | 147 | 19 |
| Water, qs (removed from formulation) | — | — |
| Total | 776 | 100 |

Formulation 3a: APAP tablets 325 mg, seal coated with 4% HPMC & enteric coated with FS30:L30D55 (90:10), 7.5 mg/cm$^2$

| Ingredients | Amount mg | % |
|---|---|---|
| Core Tablet: | | |
| Acetaminophen 325 mg tablet (Formulation 1) above | 606 | 89 |
| Seal Coating (4%): | | |
| HPMC E5 | 20 | 3 |
| PEG 6000, USP | 4 | <1 |
| Water, qs (removed from formulation) | — | |
| Functional coating (90:10) 7.5 mg/cm$^2$ | | |
| EUDRAGIT® FS30D | 44 | 6 |
| EUDRAGIT® L30D55 | 4 | <1 |
| Plasacryl | 5 | <1 |
| Water, qs (removed from formulation) | — | |
| Total | 684 | 100 |

Formulation 3b: APAP tablets 325 mg, seal coated with 4% HPMC & enteric coated with FS30:L30D55 (75:25), 7.5 mg/cm$^2$

| Ingredients | Amount mg | % |
|---|---|---|
| Core Tablet: | | |
| Acetaminophen 325 mg tablet (Formulation 1) above | 606 | 89 |
| Seal Coating (4%): | | |
| HPMC E5 | 20 | 3 |
| PEG 6000, USP | 4 | <1 |
| Water, qs (removed from formulation) | — | |
| Functional coating (75:25) 7.5 mg/cm$^2$ | | |
| EUDRAGIT® FS30D | 37 | 5 |
| EUDRAGIT® L30D55 | 12 | 2 |
| Plasacryl | 5 | <1 |
| TEC | 1 | <1 |
| Water, qs (removed from formulation) | — | |
| Total | 685 | 100 |

Formulation 3c: APAP tablets 325 mg, seal coated with 4% HPMC & enteric coated with FS30:L30D55 (50:50), 7.5 mg/cm$^2$

| Ingredients | Amount mg | % |
|---|---|---|
| Core Tablet: | | |
| Acetaminophen 325 mg tablet (Formulation 1) above | 606 | 87 |
| Seal Coating (4%): | | |
| HPMC E5 | 19 | 3 |
| PEG 6000, USP | 4 | <1 |
| Water, qs (removed from formulation) | — | |
| Functional coating (50:50) 7.5 mg/cm$^2$ | | |
| EUDRAGIT® FS30D | 25 | 4 |
| EUDRAGIT® L30D55 | 25 | 4 |
| Plasacryl | 5 | 1 |
| TEC | 1 | <1 |
| Water, qs (removed from formulation) | — | |
| Total | 685 | 100 |

Formulation 4: Composition of Uncoated APAP capsules (size #3)

| Ingredients | Amount mg | % |
|---|---|---|
| Acetaminophen (APAP) powder* | 91 | 52 |
| Lactose, USP | 72 | 41 |
| DiCalcium Phosphate | 2 | 1 |
| Colloidla silicon dioxide | 5 | 3 |
| Magnesium stearate | 5 | 3 |
| Av. Wt. of Size # 3 HPMC Quali V capsules | 51 | |
| Total | 226 | 100 |

Formulation 5: Composition APAP capsules coated with EUDRAGIT® EPO, 10 mg/cm²

| Ingredients | Amount mg | % |
|---|---|---|
| Uncoated 91 mg APAP capsule (Formulation 4) | 226 | 86 |
| Functional coating (10 mg/cm²): | | |
| EUDRAGIT ® EPO Readymix | 37 | 14 |
| Water, qs (removed from formulation) | — | |
| Total | 263 | 100 |

Formulation 6: APAP capsules (size #0) seal coated with HPMC, 6 mg/cm²

| Ingredients | Amount mg | % |
|---|---|---|
| Acetaminophen (3% PVP granulation) APAP powder | 346 | 72 |
| Av. Wt. of Size # 0 HPMC capsules | 105 | 22 |
| Total wt. of uncoated size # 0 APAP capsules | 451 | |
| Seal Coating (6 mg/cm²): | | |
| HPMC E5 | 25 | 5 |
| PEG 6000 | 4 | <1 |
| Water q.s. (removed from the formulation) | — | |
| Total | 480 | 100 |

Formulation 7 (a): APAP capsules (size #0) seal coated with HPMC, 6 mg/cm² and enteric coated with EUDRAGIT® L100, 7.5 mg/cm²

| Ingredients | mg | Amount (%) |
|---|---|---|
| APAP capsule (size # 0), seal coated (Formulation 6) | 480 | 86 |
| Functional coating (7.5 mg/cm²): | | |
| EUDRAGIT ® L100 | 39 | 8 |
| TEC | 19 | 3 |
| Talc | 19 | 3 |
| Total | 557 | 100% |

Formulation 7 (b): APAP capsules (size #0) seal coated with HPMC, 6 mg/cm² and enteric coated with EUDRAGIT® L100/EUDRAGIT® S100 (50/50) 7.5 mg/cm²

| Ingredients | mg | Amount (%) |
|---|---|---|
| APAP capsule (size # 0), seal coated (Formulation 6) | 480 | 87 |
| Functional coating (7.5 mg/cm²): | | |
| EUDRAGIT ® S100 | 18 | 4 |
| EUDRAGIT ® L100 | 18 | 4 |
| TEC | 18 | 3 |
| Talc | 17 | 2 |
| Total | 551 | 100 |

Formulation 8 (a). APAP capsules (size #0) seal coated with HPMC, 6 mg/cm² and enteric coated with EUDRAGIT® L100/EUDRAGIT® S100 (75/25) 5 mg/cm²

| Ingredients | mg | Amount (%) |
|---|---|---|
| APAP capsule (size # 0), seal coated (Formulation 6) | 480 | 87 |
| Functional coating (5 mg/cm²) (75:25) | | |
| EUDRAGIT ® L100 | 18 | 4 |
| EUDRAGIT ® S100 | 6 | 1 |
| TEC | 13 | 4 |
| Talc | 12 | 4 |
| Total | 529 | 100 |

Formulation 8 (b). APAP capsules (size #0) seal coated with HPMC, 6 mg/cm² and enteric coated with EUDRAGIT® L100/EUDRAGIT® S100 (75/25) 7.5 mg/cm²

| Ingredients | mg | Amount (%) |
|---|---|---|
| APAP capsule (size # 0), seal coated (Formulation 6) | 480 | 87 |
| Functional coating (7.5 mg/cm²) (75:25) | | |
| EUDRAGIT ® L100 | 27 | 5 |
| EUDRAGIT ® S100 | 9 | 2 |
| TEC | 17 | 3 |
| Talc | 18 | 3 |
| Total | 551 | 100 |

Formulation 9: APAP capsule-in-capsule (CIC) [inner capsule (size #3) enteric coated with EUDRAGIT® EPO, 10 mg/cm²; and outer capsule (size #0) enteric coated EUDRAGIT® L100/S100 75/25, 5 mg/cm²

| Ingredients | mg | Amount (%) |
|---|---|---|
| Acetaminophen (3% PVP granulation) APAP powder | 155 | 38 |
| Av. Wt. of Size # 3 HPMC capsules | 51 | 13 |
| Total wt. of banded uncoated size # 3 APAP capsules | 206 | |
| Inner coating (10 mg/cm²): | | |
| EUDRAGIT ® EPO ready mix | 53 | 13 |
| Water qs. (removed from formulation) | — | |
| Total wt. of coated size # 3 APAP capsule | 259 | |
| Wt. of size # 0 capsule & banding | 99 | 25 |
| Wt. of banded uncoated CIC (size # 0) filled with size # 3 coated APAP (~151 mg) capsule | 358 | |

-continued

| Ingredients | mg | Amount (%) |
|---|---|---|
| Outer coating (5 mg/cm$^2$): | | |
| EUDRAGIT ® L100 | 18 | 4 |
| EUDRAGIT ® S100 | 6 | 1 |
| TEC | 12 | 3 |
| Talc | 12 | 3 |
| Total | 406 | 100 |

From the foregoing, it will be appreciated that, although specific embodiments of the invention have been described herein for the purpose of illustration, various modifications may be made without deviating from the spirit and scope of the invention. Accordingly, the present invention is not limited except as by the appended claims.

All patents, patent applications, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Additionally, all claims in this application, and all priority applications, including but not limited to original claims, are hereby incorporated in their entirety into, and form a part of, the written description of the invention. Applicants reserve the right to physically incorporate into this specification any and all materials and information from any such patents, applications, publications, scientific articles, web sites, electronically available information, and other referenced materials or documents. Applicants reserve the right to physically incorporate into any part of this document, including any part of the written description, the claims referred to above including but not limited to any original claims.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features reported and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

REFERENCES

The contents of all references cited herein are incorporated by reference herein for all purposes.

1. Hajishengallis G, Darveau R P, Curtis M A. The keystone-pathogen hypothesis. Nat Rev Microbiol. 2012; 10(10): 717-25.
2. Furet J P, Kong L C, Tap J, Poitou C, Basdevant A, Bouillot J L, et al. Differential adaptation of human gut microbiota to bariatric surgery-induced weight loss: links with metabolic and low-grade inflammation markers. Diabetes. 2010; 59(12):3049-57.
3. Monte S V, Caruana J A, Ghanim H, Sia C L, Korzeniewski K, Schentag J J, et al. Reduction in endotoxemia, oxidative and inflammatory stress, and insulin resistance after Roux-en-Y gastric bypass surgery in patients with morbid obesity and type 2 diabetes mellitus. Surgery. 2011.
4. O'Mahony L, McCarthy J, Kelly P, Hurley G, Luo F, Chen K, et al. *Lactobacillus* and *Bifidobacterium* in irritable bowel syndrome: symptom responses and relationship to cytokine profiles. Gastroenterology. 2005; 128(3):541-51.
5. Hajishengallis G, Chavakis T. Endogenous modulators of inflammatory cell recruitment. Trends Immunol. 2012.
6. Larsen N, Vogensen F K, van den Berg F W, Nielsen D S, Andreasen A S, Pedersen B K, et al. Gut microbiota in human adults with type 2 diabetes differs from non-diabetic adults. PLoS One. 2010; 5(2):e9085.
7. Vrieze A, Holleman F, Zoetendal E G, de Vos W M, Hoekstra J B, Nieuwdorp M. The environment within: how gut microbiota may influence metabolism and body composition. Diabetologia. 2010; 53(4):606-13.

8. Maqbool S, Parkman H P, Friedenberg F K. Wireless capsule motility: comparison of the SmartPill GI monitoring system with scintigraphy for measuring whole gut transit. Dig Dis Sci. 2009; 54(10):2167-74.
9. Gao X W, Mubasher M, Fang C Y, Reifer C, Miller L E. Dose-response efficacy of a proprietary probiotic formula of *Lactobacillus acidophilus* CL1285 and *Lactobacillus casei* LBC80R for antibiotic-associated diarrhea and *Clostridium difficile*-associated diarrhea prophylaxis in adult patients. Am J Gastroenterol. 2010; 105(7): 1636-41.
10. Johnson S, Maziade P J, McFarland L V, Trick W, Donskey C, Currie B, et al. Is primary prevention of *Clostridium difficile* infection possible with specific probiotics? Int J Infect Dis. 2012.
11. Brenner D M, Moeller M J, Chey W D, Schoenfeld P S. The utility of probiotics in the treatment of irritable bowel syndrome: a systematic review. Am J Gastroenterol. 2009; 104(4): 1033-49; quiz 50.
12. Marik P E. Colonic flora, Probiotics, Obesity and Diabetes. Front Endocrinol (Lausanne). 2012; 3:87.

What is claimed is:

1. An oral delivery system for delivering a therapeutic agent to both the ileum and colon of a subject, the system comprising:
   a biodegradable first capsule comprising a formulation of a first therapeutic agent targeted to the colon,
      wherein the biodegradable first capsule comprises a reverse enteric coating that solubilizes in the colon of the subject at a pH below 6.9,
      wherein the reverse enteric coating comprises 5 mg/cm$^2$ to 10 mg/cm$^2$ of dimethylaminoethyl methacrylate-butyl methacrylate-methyl methacrylate copolymer (2:1:1) copolymer; and
   a biodegradable second capsule that includes the biodegradable first capsule and a formulation of a second therapeutic agent targeted to the ileum,
      wherein the biodegradable second capsule comprises an enteric coating that solubilizes in the ileum of the subject at a pH of about 7 to about 8,
      wherein the enteric coating comprises 5 mg/cm$^2$ to 10 mg/cm$^2$ of poly(methacrylic acid-co-methyl-methacrylate) 1:1 copolymer and poly(methacrylic acid-co-methyl-methacrylate) 1:2 copolymer in a 75/25 ratio,
      wherein the second capsule releases the biodegradable first capsule and the formulation of the second therapeutic agent targeted to the ileum and once released, the biodegradable first capsule is solubilized in the colon of the subject and releases the formulation of the first therapeutic agent targeted to the colon,
      wherein the second therapeutic agent in the biodegradable second capsule is delivered to the ileum without leakage of the first therapeutic agent in the proximal area of the colon, and
      wherein each of the first therapeutic agent and the second therapeutic agent comprise a probiotic comprising a species from at least one of a *Lactobacillus* genus and a *Bifidobacterium* genus and at least one additional agent that is selected from the group consisting of: acetaminophen, metformin, linaclotide, lipids, nutritional agents, statins, diabetogenic foods, nutrients, vitamins, prebiotics, pH encapsulated glucose, anti-inflammatory agents, an ileal brake hormone releasing substance, an antibiotic, a tumor Necrosis Factor (TNF) antagonist, human bacterial fecal flora, and osmotic agents.

2. The oral delivery system of claim 1, wherein the biodegradable first capsule and the biodegradable second capsule are each fabricated of hydroxypropylmethyl cellulose.

3. A capsule-in-capsule oral delivery system comprising:
   an inner biodegradable capsule contained within an outer biodegradable capsule,
      wherein the inner capsule comprises a first therapeutic agent, and
      wherein the inner capsule is coated with a reverse enteric coating comprising 5 mg/cm$^2$ to 10 mg/cm$^2$ of dimethylaminoethyl methacrylate-butyl methacrylate-methyl methacrylate copolymer (2:1:1) that solubilizes in the proximal colon of a subject at a pH below 6.9 to deliver the first therapeutic agent in the proximal colon; and
   the outer biodegradable capsule containing the inner biodegradable capsule and a second therapeutic agent,
      wherein the outer biodegradable capsule is coated with an enteric coating comprising poly(methacrylic acid-co-methyl-methacrylate) 1:1 copolymer and poly(methacrylic acid-co-methyl-methacrylate) 1:2 copolymer that solubilizes in the ileum of the subject at a pH of about 7 to about 8 to deliver the second therapeutic agent to the ileum,
      wherein the enteric coating comprises 5 mg/cm$^2$ to 10 mg/cm$^2$ of poly(methacrylic acid-co-methyl-methacrylate) 1:1 copolymer and poly(methacrylic acid-co-methyl-methacrylate) 1:2 copolymer in a 75/25 ratio,
      wherein the second therapeutic agent in the outer biodegradable capsule is delivered to the ileum without leakage of the first therapeutic agent in the proximal area of the colon, and
      wherein each of the first therapeutic agent and the second therapeutic agent comprise a probiotic comprising a species from at least one of a *Lactobacillus* genus and a *Bifidobacterium* genus and at least one additional agent that is selected from the group consisting of: acetaminophen, metformin, linaclotide, lipids, nutritional agents, statins, diabetogenic foods, nutrients, vitamins, prebiotics, pH encapsulated glucose, anti-inflammatory agents, an ileal brake hormone releasing substance, an antibiotic, a tumor Necrosis Factor (TNF) antagonist, human bacterial fecal flora, and osmotic agents.

4. The capsule-in-capsule oral delivery system of claim 3, wherein the reverse enteric coating has a thickness of 60 μm to 180 μm.

5. The capsule-in-capsule oral delivery system of claim 3, wherein the enteric coating has a thickness of 60 μm to 180 μm.

6. The capsule-in-capsule oral delivery system of claim 3, wherein the inner biodegradable capsule is a size no. 3 hydroxypropylmethyl cellulose capsule.

7. The capsule-in-capsule oral delivery system of claim 3, wherein the outer biodegradable capsule is a size no. 0 hydroxypropylmethyl cellulose capsule.

8. The oral delivery system of claim 1, wherein each of the biodegradable first capsule and the biodegradable second capsule comprise hydroxypropylmethyl cellulose.

9. The oral delivery system of claim 1, wherein the biodegradable first capsule is band sealed.

10. The oral delivery system of claim 1, wherein the biodegradable second capsule is band sealed.

11. A capsule-in-capsule oral delivery system comprising:
an inner biodegradable capsule contained within an outer biodegradable capsule,
   wherein the inner biodegradable capsule contains an inner therapeutic agent,
   wherein the inner biodegradable capsule comprises hydroxypropylmethyl cellulose and is coated with a reverse enteric coating that solubilizes in the proximal colon of a subject at a pH below 6.9, and
   wherein the reverse enteric coating comprises 5 mg/cm$^2$ to 10 mg/cm$^2$ of dimethylaminoethyl methacrylate-butyl methacrylate-methyl methacrylate copolymer (2:1:1) copolymer; and
the outer biodegradable capsule contains the inner biodegradable capsule and an outer therapeutic agent, and is coated with an enteric coating that solubilizes in the ileum of the subject at a pH of about 7 to about 8,
   wherein the enteric coating comprises 5 mg/cm$^2$ to 10 mg/cm$^2$ of poly(methacrylic acid-co-methyl-methacrylate) 1:1 copolymer and poly(methacrylic acid-co-methyl-methacrylate) 1:2 copolymer in a 75/25 ratio,
   wherein the outer therapeutic agent in the outer biodegradable capsule is delivered to the ileum without leakage of the inner therapeutic agent in the proximal area of the colon, and
   wherein each of the inner therapeutic agent and the outer therapeutic agent comprise a probiotic comprising a species from at least one of a *Lactobacillus* genus and a *Bifidobacterium* genus and at least one additional agent that is selected from the group consisting of: acetaminophen, metformin, linaclotide, lipids, nutritional agents, statins, diabetogenic foods, nutrients, vitamins, prebiotics, pH encapsulated glucose, anti-inflammatory agents, an ileal brake hormone releasing substance, an antibiotic, a tumor Necrosis Factor (TNF) antagonist, human bacterial fecal flora, and osmotic agents.

12. The capsule-in-capsule delivery system of claim 11, wherein each of the inner biodegradable capsule and the outer biodegradable capsule are band sealed.

13. The capsule-in-capsule delivery system of claim 11, wherein each of the inner biodegradable capsule and the outer biodegradable capsule comprise hydroxypropylmethyl cellulose.

14. The oral delivery system according to claim 1, wherein the formulation of each of the first therapeutic agent and the second therapeutic agent are formulated as tablets, microtablets, granules, microgranules, powders, liquids, pellets or micropellets.

* * * * *